US012630801B2

(12) United States Patent
Studer et al.

(10) Patent No.: US 12,630,801 B2
(45) Date of Patent: May 19, 2026

(54) STEM CELL-DERIVED SCHWANN CELLS

(71) Applicant: MEMORIAL SLOAN-KETTERING CANCER CENTER, New York, NY (US)

(72) Inventors: Lorenz Studer, New York, NY (US); Faranak Fattahi, New York, NY (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 524 days.

(21) Appl. No.: 16/410,686

(22) Filed: May 13, 2019

(65) Prior Publication Data

US 2019/0264173 A1 Aug. 29, 2019

Related U.S. Application Data

(63) Continuation of application No. PCT/US2017/061541, filed on Nov. 14, 2017.

(60) Provisional application No. 62/421,816, filed on Nov. 14, 2016.

(51) Int. Cl.

| | |
|---|---|
| ***C12N 5/079*** | (2010.01) |
| ***A61K 35/28*** | (2015.01) |
| ***A61K 35/30*** | (2015.01) |
| ***A61P 19/00*** | (2006.01) |
| ***C12N 5/00*** | (2006.01) |
| ***G01N 33/50*** | (2006.01) |

(52) U.S. Cl.

CPC ............ *C12N 5/0622* (2013.01); *A61K 35/28* (2013.01); *A61K 35/30* (2013.01); *A61P 19/00* (2018.01); *C12N 5/0062* (2013.01); *G01N 33/5038* (2013.01); *G01N 33/5058* (2013.01); *C12N 2501/01* (2013.01); *C12N 2501/113* (2013.01); *C12N 2501/115* (2013.01); *C12N 2501/117* (2013.01); *C12N 2501/119* (2013.01); *C12N 2501/15* (2013.01); *C12N 2501/415* (2013.01); *C12N 2501/999* (2013.01); *C12N 2506/02* (2013.01); *C12N 2506/08* (2013.01); *C12N 2513/00* (2013.01)

(58) Field of Classification Search

CPC .......................... C12N 5/0622; C12N 5/0062; C12N 2501/01; C12N 2501/113; C12N 2501/115; C12N 2501/117; C12N 2501/119; C12N 2501/15; C12N 2501/415; C12N 2501/999; C12N 2506/02; C12N 2513/00; C12N 2506/08; A61P 19/00; A61K 35/28; A61K 35/30; G01N 33/5038

USPC .......................................................... 435/377

See application file for complete search history.

(56) References Cited

U.S. PATENT DOCUMENTS

| | | | |
|---|---|---|---|
| 2013/0183674 | A1 | 7/2013 | Studer et al. |
| 2014/0028949 | A1 | 1/2014 | Kuo et al. |
| 2014/0038949 | A1 | 2/2014 | Schultz et al. |
| 2014/0105861 | A1 | 4/2014 | March et al. |
| 2015/0010515 | A1 | 1/2015 | Schoeler et al. |
| 2019/0331666 | A1 | 10/2019 | Studer et al. |

FOREIGN PATENT DOCUMENTS

| | | | |
|---|---|---|---|
| JP | 2011-050379 | A | 3/2011 |
| KR | 10-2014-0116063 | | 10/2014 |
| WO | WO 2000/19993 | A2 | 4/2000 |
| WO | WO 2011/046189 | A1 | 4/2011 |
| WO | WO 2015/011031 | A1 | 1/2015 |
| WO | WO 2016/039462 | A1 | 3/2016 |
| WO | WO 2016/187135 | A1 | 11/2016 |
| WO | WO 2018/135907 | A1 | 7/2018 |

OTHER PUBLICATIONS

Stuhlmiller et al ("Current perspectives of the signaling pathways directing neural crest induction," Cell. Mol. Life Sci. (2012) 69: 3715-3737) (Year: 2012).*

Chen, 2013, Journal of Neuroscience Research 91:30-41.*

Lee, 2013, PLoS ONE, 8:e68931.*

Hussain, BBA—Molecular Basis of Disease 1863 (2017) 3226-3242.*

Katoh, Cancer Biology and Therapy, 2006, 5:1059-1064.*

Gordon, 2006, Journal of Biological Chemistry, 281:22429-22433.*

Willert, CSH Perspectives in Biology, 2012, 4:1-13.*

MacDonald (2009, Developmental Cell, 17:9-26).*

U.S. Appl. No. 16/410,763, Aug. 3, 2021 Final Office Action.

Al-Zer et al., "Enrichment and Schwann Cell Differentiation of Neural Crest-derived Dental Pulp Stem Cells," In Vivo. 29:319-326 (2015).

Martens et al., "Human dental pulp stem cells can differentiate into Schwann cells and promote and guide neurite outgrowth in an aligned tissue-engineered collagen construct in vitro," FASEB J. 28:1634-1643 (2014).

(Continued)

*Primary Examiner* — Valarie E Bertoglio

(74) *Attorney, Agent, or Firm* — Baker Botts L.L.P.

(57) ABSTRACT

The presently disclosed subject matter provides for in vitro methods of inducing differentiation of stem cells into Schwann cell precursors and Schwann cells, and Schwann cell precursors and Schwann cells generated by such methods. The presently disclosed subject matter also provides for uses of such Schwann cell precursors and Schwann cells for regeneration of PNS and/or CNS, for prevention and/or repair of myelin damages, and/or for prevention and/or treatment of Schwann cell related disorders (e.g., peripheral neuropathy, e.g., Diabetic Peripheral Neuropathy).

13 Claims, 10 Drawing Sheets

(56) References Cited

OTHER PUBLICATIONS

Tomita et al., "Glial Differentiation of Human Adipose-Derived Stem Cells Implications for Cell-Based Transplantation Therapy," Neuroscience 236:55-65 (2013).
Xiao et al., "Differentiation of Schwann-like cells from human umbilical cord blood mesenchymal stem cells in vitro," Mol. Med. Rep. 11:1146-1152 (2015).
U.S. Appl. No. 16/410,763, Jul. 21, 2020 Response to Restriction Requirement.
U.S. Appl. No. 16/410,763, Oct. 14, 2020 Non-Final Office Action.
Askwith et al., "Oxidative stress and dysregulation of the taurine transporter in high-glucose-exposed human Schwann cells: implications for pathogenesis of diabetic neuropathy," Am J Physiol Endocrinol Metab 297:E620-E628 (2009).
Judge et al., "Potassium channel blockers in multiple sclerosis: Neuronal Kv channels and effects of symptomatic treatment," Pharmacology and Therapeutics 111:224-259 (2006).
Shi et al., "Potassium channel blockers as an effective treatment to restore impulse conduction in injured axons," Neuroscience Bulletin, 27(1):36-44 (2011).
Siniscalchi et al., "Open, Uncontrolled, Nonrandomized, 9-month, Off-Label Use of Bupropion to Treat Fatigue in a Single Patient with Multiple Sclerosis," Clinical Therapeutics 32(12):2030-2034 (2010).
Sun et al., "Protective Effects by Salvianolic Acid B on Schwann Cells Apoptosis Induced by Hugh Glucose," Neurochem Res. 37:996-1010 (2012).
U.S. Appl. No. 16/410,763 (US 2019/0331666), filed May 13, 2019 (Oct. 31, 2019).
U.S. Appl. No. 16/410,763, Jan. 27, 2020 Restriction Requirement.
Aquino et al., "In Vitro and in Vivo Differentiation of Boundary Cap Neural Crest Stem Cells Into Mature Schwann Cells," Exp Neurol., 198, 438-449 (2005).
Chambers et al., "Highly efficient neural conversion of human ES and iPS cells by dual inhibition of SMAD signaling," Nat Biotechnol., 27, 275-280 (2009).
Delaney et al., "Insulin-Like Growth Factor-I and Over-Expression of Bcl-xL Prevent Glucose Mediated Apoptosis in Schwann Cells," Journal of Neuropathology & Experimental Neurology, vol. 60, Iss. 2, 147-160.
Denham et al., "Multipotent Caudal Neural Progenitors Derived from Human Pluripotent Stem Cells That Give Rise to Lineages of the Central and Peripheral Nervous System," Stem Cells, vol. 33, No. 6, 1759-1770.
Dupin et al., "Neural crest progenitors and stem cells," C R Biologies, 330, 521-529 (2007).
Ekins et al., "A brief review of recent Charcot-Marie-Tooth research and priorities [version 1; referees: 2 approved]," F1000Research, 4, 14 pages (2016).
Hao et al., "Hyperglycemia Promotes Schwann Cell De-differentiation and De-myelination via Sorbitol Accumulation and Igf1 Protein Down-regulation," Journal of Biological Chemistry, 17106-17115 (2015).
International Search Report mailed Feb. 7, 2018 in International Application No. PCT/US2017/061541.
International Search Report mailed Feb. 7, 2018 in International Application No. PCT/US2017/061549.
Karihaloo et al., "Effect of Sorbinil and Ascorbic Acid on myo-Inositol Transport in Cultured Rat Schwann Cells Exposed to Elevated Extracellular Glucose," Journal of Neurochemistry, 69, 2011-2018 (1997).
Lee et al., "Isolation and Directed Differentiation of Neural Crest Stem Cells Derived from Human Embryonic Stem Cells," Nature Biotechnology, vol. 25, No. 12, 1468-1475.
Liu et al., "Specific Marker Expression and Cell State of Schwann Cells during Culture In Vitro," PLOS ONE, 1-17 (2015).
Liu et al., "Effects of High Glucose on Cell Viability and Differentiation in Primary Cultures Schwann Cells: Potential Role of ERK Signaling Pathway," Neurochem Res , 41, 1281-1290 (2016).
Liu et al., "Human Neural Crest Stem Cells Derived from Human ESCs and Induced Pluripotent Stem Cells: Induction, Maintenance, and Differentiation into Functional Schwann Cells," Stem Cells Translation Medicine, 1, 266-278 (2015).
Ma et al., "Pluripotent Stem Cells for Schwann Cell Engineering," Stem Cell Rev and Rep, 11, 205-218 (2014).
Melli et al., "Dorsal Root Ganglia Sensory Neuronal Cultures: a tool for drug discovery for peripheral neuropathies," Expert Opin Drug Discov., 4, 1035-1045 (2009).
Mica et al., "Modeling Neural Crest Induction, Melanocyte Specification, and Disease-Related Pigmentation Defects in hESCs and Patient-Specific iPSCs," Cell Reports, 3, 1140-1152 (2013).
Nat R. "Chapter 15: From Human Pluripotent Stem Cells to Peripheral Neurons," in Pluripotent Stem-Cells-From the Bench to the Clinic, Ed. Minoru Tomizawa, 307-329.
Ostrow et al., "Immortalized Human Schwann Cell Lines Derived From Tumors of Schwannomatosis Patients, " PLOS ONE, pp. 1-15, (2015).
Sakaue et al., "Human epidermal neural crest stem cells as a source of Schwann cells," Development, 142, 3188-3197 (2015).
Semenchuk et al., "Double-blind, randomized trial of bupropion SR for the treatment of neuropathic pain," Neurology 57, 1583-1588 (2001).
Supplementary European Search Report and Search Opinion for EP Patent Application No. 17870215.5.
Supplementary European Search Report and Search Opinion for EP Patent Application No. 17870058.9.
Thoma et al., "Chemical Conversion of Human Fibroblasts into Functional Schwann Cells," Stem Cell Reports, 3, 539-547 (2014).
Zeltner et al., "Feeder-free Derivation of Neural Crest Progenitor Cells from Human Pluripotent Stem Cells," J Vis Exp, 87, e51309, pp. 1-9 (2014).
European Examination Report dated Mar. 14, 2022 for EP Patent Application No. 17870215.5.
European Examination Report dated Mar. 1, 2022 for EP Patent Application No. 17870058.9.
U.S. Appl. No. 16/410,763, Dec. 28, 2022 Non-Final Office Action.
Kuruvilla et al., "Depletion of Phospholipid Arachidonoyl-Containing Molecular Species in a Human Schwann Cell Line Grown in Elevated Glucose and Their Restoration by an Aldose Reductase Inhibitor," J Neurochem, 71:775-783 (1998).
Ziegler et al., "Efficient Generation of Schwann Cells from Human Embryonic Stem Cell-Derived Neurospheres," Stem Cell Rev and Rep 7:394-403 (2011).
U.S. Appl. No. 16/410,763, Mar. 27, 2024 Non-Final Office Action.
Huang et al., "Generating trunk neural crest from human pluripotent stem cells," Scientific Reports 6:19727 (2016) [9 pgs.].
Lee et al., "Derivation of neural crest cells from human pluripotent stem cells," Nature Protocols 5(4):688-701 (2010).
U.S. Appl. No. 16/410,763, Sep. 30, 2024 Final Office Action.
Grigoryan et al., "Molecular signaling mechanisms of axon-glia communication in the peripheral nervous system," Article in BioEssays—(Feb. 2015), 13 pgs. [Figure 1 only].
Mirsky et al., "Novel signals controlling embryonic Schwann cell development, myelination and dedifferentiation," Journal of the Peripheral Nervous System 13:122-135 (2008).

* cited by examiner

Schwann cell grafting

Sciatic nerve crush injury

SC-101 NFH DAPI

200 μm

EF1::RFP NFH DAPI

20 μm    10 μm

5 μm

EF1::RFP MAG DAPI

EF1::RFP PO DAPI

EF1::RFP CASPR DAPI

20 μm

EF1::RFP K$^V$1.2 DAPI

EF1::RFP PanNa$^+$ DAPI

STEM CELL-DERIVED SCHWANN CELLS

CROSS REFERENCE TO RELATED APPLICATIONS

This application is a Continuation of International Patent Application No. PCT/US17/61541 filed Nov. 14, 2017, which claims priority to U.S. Provisional Patent Application No. 62/421,816 filed Nov. 14, 2016, and the contents of each of which are hereby incorporated by reference in their entireties herein, and to each of which priority is claimed.

INTRODUCTION

The presently disclosed subject matter relates to Schwann cell precursors and Schwann cells derived from stem cells (e.g., human stem cells) and uses thereof for cell-based treatment in regeneration of peripheral nervous system (PNS) and/or central nervous system ("CNS"), prevention and/or repair of myelin damages, and/or prevention and/or treatment of peripheral neuropathy (e.g., diabetic peripheral neuropathy).

BACKGROUND

Schwann cells (SCs) are the glia of the peripheral nervous system (PNS) and essential for PNS function. They develop from the neural crest (NC) via a Schwann cell precursor (SCP) intermediate. SCs play crucial roles in functional regulation, maintenance and repair of the PNS and exhibit a remarkable ability to promote neural repair following injury (Jessen et al., 2015; Lavdas et al., 2008). SC defects are involved in a broad range of human disorders such as Schwannomatosis, Charcot Marie Tooth Disease, Guillain Barre Syndrome and various other peripheral neuropathies including Diabetic Peripheral Neuropathy (DPN).

Diabetes Mellitus is the leading cause of peripheral neuropathy, affecting 30% (Callaghan et al., 2012) to 60% (Zochodne, 2007) of diabetic patients. It represents a major health problem causing reduced quality of life and increased morbidity and mortality (La Fontaine et al., 2014). Medical costs related to DPN in the US were estimated at $4.6-$13.7 billion per year in 2001 and continue to increase (Gordois et al., 2003) The symptoms of DPN are diverse but include sensory dysfunction and pain as well as autonomic and ENS complications.

There are currently no effective treatments for DPN other than pursuing the primary goal of preventing further damage by carefully monitoring and adjusting glucose levels. Symptomatic treatments include the use of antidepressants, anticonvulsants as well as opioids to cope with the neuropathic pain.

The pathogenesis of DPN likely involves several complex contributing factors that lead to cytotoxicity and degeneration in peripheral nerves (Simmons and Feldman, 2002). There is evidence that hyperglycemia, hypoxia and oxidative stress in diabetes lead to degeneration of SCs particularly in the sensory nerves (Eckersley, 2002). While the ultimate symptoms arise from dysfunction of the neurons, it is unclear whether sensory neurons or glia play a key role in the pathogenesis of DPN. Dissecting such mechanisms is very challenging in current animal models given the complex contribution of non-cell autonomous factors to the disease phenotype.

Previously established hPSC differentiation protocols enable systematic access to sensory neurons, but there are no robust methods for induction of SCs from hPSC. Furthermore, the subsequent SC-like cells do not exhibit a robust expression of key lineage markers and generally fail to produce myelin structures. Therefore, there remains a need for an in vitro method and protocol of generating SC precursors and SCs from human stem cells.

SUMMARY OF THE INVENTION

The presently disclosed subject matter relates to Schwann cell precursors and Schwann cells derived from stem cells (e.g., human stem cells), e.g., by in vitro differentiation, and to methods of making and using said cells.

In certain embodiments, the presently disclosed subject matter provides in vitro methods for inducing differentiation of neural crest lineage cells. In certain embodiments, the method comprises contacting a population of cells that express one or more neural crest lineage marker with one or more activator of wingless (Wnt) signaling (referred to as "Wnt activator"), and one or more activator of Fibroblast Growth Factor (FGF) signaling (referred to as "FGF activator") to produce a population of cells that express one or more Schwann cell precursor marker. In certain embodiments, the method comprises contacting the population of cells that express one or more neural crest lineage marker with the one or more Wnt activator, and one or more FGF activator for at least about 3 days. In certain embodiments, the method comprises contacting the population of cells that express one or more neural crest lineage marker with the one or more Wnt activator, and one or more FGF activator for up to about 30 days. In certain embodiments, the method comprises contacting the population of cells that express one or more neural crest lineage marker with the one or more Wnt activator, and one or more FGF activator for between about 5 days and about 15 days or between about 10 days and 15 days.

In certain embodiments, the cells that express one or more neural crest lineage marker are neural crest cells. In certain embodiments, the neural crest lineage marker is selected from the group consisting of SOX10, p75, HNK1, CD49D, ERBB3, TFAP2, SNAIL and SLUG.

In certain embodiments, the method further comprises contacting the population of cells that express one or more neural crest lineage marker with one or more molecule that induces Schwann cell differentiation (referred to as "SC differentiation inducer"). In certain embodiments, the method comprises contacting the population of cells that express one or more neural crest lineage marker with the SC differentiation inducer for at least about 3 days. In certain embodiments, the method comprises contacting the population of cells that express one or more neural crest lineage marker with the SC differentiation inducer for up to about 30 days. In certain embodiments, the method comprises contacting the population of cells that express one or more neural crest lineage marker with the SC differentiation inducer for between about 5 days and about 15 days or between about 10 days and 15 days. In certain embodiments, the method comprises contacting the population of cells that express one or more neural crest lineage marker with the one or more Wnt activator, one or more FGF activator, and the SC differentiation inducer simultaneously and/or concurrently.

In certain embodiments, the presently disclosed subject matter provides in vitro methods for inducing differentiation of stem cells.

In certain embodiments, the in vitro method for inducing differentiation of stem cells comprises: in vitro differentiating a population of stem cells (referred to as "stem cell population") to a population of cells that express one or more neural crest lineage marker, and contacting the differentiated cells with one or more Wnt activator, and one or more FGF activator to produce a population of cells that express one or more Schwann cell precursor marker. In certain embodiments, the method comprises contacting the population of cells that express one or more neural crest lineage marker with the one or more Wnt activator, and one or more FGF activator for at least about 3 days. In certain embodiments, the method comprises contacting the population of cells that express one or more neural crest lineage marker with the one or more Wnt activator, and one or more FGF activator for up to about 30 days. In certain embodiments, the method comprises contacting the differentiated cells with the one or more Wnt activator, and one or more FGF activator for between about 5 days and about 15 days or between about 10 days and 15 days.

In certain embodiments, the method further comprises contacting the population of cells that express one or more neural crest lineage marker with one or more SC differentiation inducer. In certain embodiments, the method comprises contacting the population of cells that express one or more neural crest lineage marker with the SC differentiation inducer for at least about 3 days. In certain embodiments, the method comprises contacting the population of cells that express one or more neural crest lineage marker with the SC differentiation inducer for up to about 30 days. In certain embodiments, the method comprises contacting the population of cells that express one or more neural crest lineage marker with the SC differentiation inducer for between about 5 days and about 15 days or between about 10 days and 15 days. In certain embodiments, the method comprises contacting the population of cells that express one or more neural crest lineage marker with the one or more Wnt activator, one or more FGF activator, and SC differentiation inducer simultaneously.

In certain embodiments, the in vitro differentiation of the stem cell population to a population of cells that express one or more neural crest lineage marker comprises inhibiting SMAD signaling and activation of Wnt signaling. In certain embodiments, the in vitro differentiating a stem cell population to a population of cells that express one or more neural crest lineage marker comprises contacting the stem cell population with one or more inhibitor of transforming growth factor beta (TGFβ)/Activin-Nodal signaling, and one or more Wnt activator.

In certain embodiments, the in vitro method for inducing differentiation of stem cells, comprising contacting a population of stem cells with one or more inhibitor of TGFβ/Activin-Nodal signaling, further contacting the cells with one or more Wnt activator, and one or more FGF activator. In certain embodiments, the method further comprises contacting the cells with one or more SC differentiation inducer. In certain embodiments, the method comprises contacting the cells with the one or more Wnt activator, one or more FGF activator, and the SC differentiation inducer simultaneously and/or concurrently.

In certain embodiments, the method comprises contacting the cells with the one or more FGF activator for at least about 3 days, for at least about 4 days, for at least about 5 days, for at least about 6 days, for at least about 7 days, for at least about 8 days, for at least about 9 days, for at least about 10 days, for at least about 11 days, at least about 12 days, at least about 13 days, at least about 14 days, at least about 15 days, at least about 16 days, at least about 17 days, at least about 18 days, at least about 19 days, or at least about 20 days, to produce a population of differentiated cells that express one or more Schwann cell precursor marker. In certain embodiments, the method comprises contacting the cells with the one or more FGF activator for between about 10 days and about 20 days or between about 10 days and about 15 days, to produce a population of differentiated cells that express one or more Schwann cell precursor marker. In certain embodiments, the method comprises contacting the cells with and the one or more FGF activator for 14 days to produce a population of differentiated cells that express one or more Schwann cell precursor marker. In certain embodiments, the method comprises contacting the cells with the one or more FGF activator for about 15 days to produce a population of differentiated cells that express one or more Schwann cell precursor marker.

In certain embodiments, the initial contact of the one or more FGF activator with the cells is at least about 5 days (e.g., no later than about 20 days) from the initial contact of the stem cells with the one or more inhibitor of TGFβ/Activin-Nodal signaling. In certain embodiments, the initial contact of the one or more FGF activator with the cells is between about 5 days and about 20 days (e.g., about 5 days, about 6 days, about 7 days, about 8 days, about 9 days, about 10 days, about 11 days, about 12, days, about 13 days, about 14 days, about 15 days, about 16 days, about 17 days, about 18 days, about 19 days, or about 20 days) after the initial contact of the stem cell population with the one or more inhibitor of TGFβ/Activin-Nodal signaling.

In certain embodiments, the method further comprises contacting the cells with the one or more SC differentiation inducer for at least about 3 days, for at least about 4 days, for at least about 5 days, for at least about 6 days, for at least about 7 days, for at least about 8 days, for at least about 9 days, for at least about 10 days, for at least about 11 days, at least about 12 days, at least about 13 days, at least about 14 days, at least about 15 days, at least about 16 days, at least about 17 days, at least about 18 days, at least about 19 days, or at least about 20 days, to produce a population of differentiated cells that express one or more Schwann cell precursor marker. In certain embodiments, the method comprises contacting the about with the one or more SC differentiation inducer for between about 10 days and about 20 days or between about 10 days and about 15 days, to produce a population of differentiated cells that express one or more Schwann cell precursor marker. In certain embodiments, the method comprises contacting the cells with and the one or more SC differentiation inducer for about 14 days to produce a population of differentiated cells that express one or more Schwann cell precursor marker. In certain embodiments, the method comprises contacting the cells with the one or more SC differentiation inducer for about 15 days to produce a population of differentiated cells that express one or more Schwann cell precursor marker.

In certain embodiments, the initial contact of the one or more SC differentiation inducer with the cells is at least about 5 days (e.g., no later than about 20 days) after the initial contact of the stem cells with the one or more inhibitor of TGFβ/Activin-Nodal signaling. In certain embodiments, the initial contact of the one or more SC differentiation inducer with the cells is between about 5 days and about 20 days (e.g., about 5 days, about 6 days, about 7 days, about 8 days, about 9 days, about 10 days, about 11 days, about 12, days, about 13 days, about 14 days, about 15 days, about 16 days, about 17 days, about 18 days, about 19 days, or about 20 days) after the initial contact of the stem cells with the one or more inhibitor of TGFβ/Activin-Nodal signaling.

In certain embodiments, the presently disclosed subject matter provides for in vitro methods for inducing differentiation of stem cells. In certain embodiments, the in vitro method for inducing differentiation of a population of stem cells comprises contacting the stem cell population with one or more inhibitor of TGFβ/Activin-Nodal signaling, and one or more activator of Wnt activator, and further contacting the cells with and one or more FGF activator, wherein the initial contact of the one or more FGF activator with the cells is no later than about 20 days from the initial contact of the stem cell population with the one or more inhibitor of TGFβ/Activin-Nodal signaling.

In certain embodiments, the initial contact of the one or more FGF activator with the cells is about 10 days from the initial contact of the stem cells with the one or more inhibitor of TGFβ/Activin-Nodal signaling. In certain embodiments, the initial contact of the one or more FGF activator with the cells is about 11 days from the initial contact of the stem cells with the one or more inhibitor of TGFβ/Activin-Nodal signaling.

In certain embodiments, the method further comprises contacting the cells with one or more SC differentiation inducer, wherein the initial contact of the one or more SC differentiation inducer with the cells is no later than about 20 days from the initial contact of the stem cells with the one or more inhibitor of TGFβ/Activin-Nodal signaling.

In certain embodiments, the initial contact of the one or more SC differentiation inducer with the cells is about 10 days from the initial contact of the stem cells with the one or more inhibitor of TGFβ/Activin-Nodal signaling. In certain embodiments, the initial contact of the one or more SC differentiation inducer with the cells is about 11 days from the initial contact of the stem cells with the one or more inhibitor of TGFβ/Activin-Nodal signaling. In certain embodiments, the method comprises contacting the cells with the one or more FGF activator and the one or more SC differentiation inducer simultaneously and/or concurrently.

In certain embodiments, the initial contact of the one or more Wnt activator with the cells is no later than about 4 days from the initial contact of the stem cells with the one or more inhibitor of TGFβ/Activin-Nodal signaling. In certain embodiments, the initial contact of the one or more Wnt activator with the cells is about 2 days from the initial contact of the stem cells with the one or more inhibitor of TGFβ/Activin-Nodal signaling. In certain embodiments, the initial contact of the one or more Wnt activator with the cells occurs on the same as the initial contact of the stem cells with the one or more inhibitor of TGFβ/Activin-Nodal signaling.

In certain embodiments, the one or more Schwann cell precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4. In certain embodiments, the one or more Schwann cell precursor marker is selected from the genes listed in Tables 1-4. In certain embodiments, the one or more Schwann cell precursor marker is selected from the genes listed in Table 1. In certain embodiments, the one or more Schwann cell precursor marker is selected from the group consisting of CALCB, GRP116, TSPYL5, ITPKA, SLC17A6, SYPL2, LOC100128252, ANGPTL7, LOC728978, and ZNF502.

In certain embodiments, the method comprises further contacting the stem cells with one or more inhibitor of Small Mothers Against Decapentaplegic (SMAD) signaling "referred to as "SMAD inhibitor"). In certain embodiments, the method comprises contacting the stem cells with the one or more inhibitor of TGFβ/Activin-Nodal signaling and the SMAD inhibitor concurrently.

In certain embodiments, the method further comprises subjecting the population of differentiated cells expressing one or more SC precursor marker to conditions favoring maturation of the differentiated cells into a population of Schwann cells that express one or more Schwann cell marker. The Schwann cells can become myelinating Schwann cells or non-myelinating Schwann cells.

In certain embodiments, the conditions favoring maturation of the differentiated SC precursor cells into a population of Schwann cells comprise contacting the population of differentiated cells with the one or more FGF activator and the one or more Schwann cell differentiation inducer. In certain embodiments, the conditions further comprise contacting the population of differentiated cells with one or more molecule that enhances Schwann cell differentiation (referred to as "SC differentiation enhancer). In certain embodiments, the conditions favoring maturation of the differentiated SC precursor cells into a population of Schwann cells further comprise contacting the population of differentiated cells with the one or more FGF activator, the one or more Schwann cell differentiation inducer, and the one or more SC differentiation enhancer simultaneously and/or concurrently. In certain embodiments, the one or more SC differentiation enhancer is selected from the group consisting of cyclic adenosine monophosphate (cAMP), Forskolin, LIF, and CNTF.

In certain embodiments, the conditions favoring maturation of the differentiated SC precursor cells into a population of Schwann cells comprise contacting the population of differentiated SC precursor cells with the one or more FGF activator and the one or more Schwann cell differentiation inducer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days. In certain embodiments, the conditions favoring maturation of the differentiated SC precursor cells into a population of Schwann cells comprise contacting the population of differentiated SC precursor cells with the one or more FGF activator and the one or more Schwann cell differentiation inducer for about 10 days. In certain embodiments, the conditions favoring maturation of the differentiated SC precursor cells into a population of Schwann cells comprise contacting the population of differentiated SC precursor cells with the one or more FGF activator and the one or more Schwann cell differentiation inducer for about 11 days. In certain embodiments, the conditions favoring maturation of the differentiated SC precursor cells into a population of Schwann cells comprise contacting the population of differentiated SC precursor cells with the one or more FGF activator and the one or more Schwann cell differentiation inducer for about 35 days.

In certain embodiments, the conditions further comprise contacting the population of differentiated SC precursor cells with the one or more SC differentiation enhancer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days. In certain embodiments, the conditions favoring maturation of the differentiated SC precursor cells into a population of Schwann cells comprise contacting the population of differentiated SC precursor cells with the one or more SC differentiation enhancer for about 10 days. In certain embodiments, the conditions favoring maturation of the differentiated SC precursor cells into a population of Schwann cells comprise contacting the population of differentiated SC precursor cells with the one or more SC differentiation enhancer for about 11 days. In certain embodiments, the conditions favoring maturation of the differentiated SC precursor cells into a population of Schwann cells comprise contacting the population of differentiated SC precursor cells with the one or more SC differentiation enhancer for about 35 days.

In certain embodiments, the method comprises contacting the cells with the one or more FGF activator, the one or more SC differentiation inducer, and the one or more SC differentiation enhancer simultaneously and/or concurrently.

In certain embodiments, the conditions favoring maturation of the differentiated SC precursor cells into a population of Schwann cells further comprise aggregating the population of differentiated SC precursor cells into 3D spheroids; and contacting the 3D spheroids with the one or more FGF activator and the one or more Schwann cell differentiation inducer. In certain embodiments, the conditions further comprise contacting the 3D spheroids with one or more SC differentiation enhancer. In certain embodiments, the conditions comprise contacting the 3D spheroids with the one or more FGF activator, the one or more Schwann cell differentiation inducer, and the one or more SC differentiation enhancer simultaneously and/or concurrently. In certain embodiments, the method further comprises culturing the 3D spheroids in a suspension culture.

In certain embodiments, the one or more Schwann cell marker is selected from the group consisting of LRRTM4, CDH1, FABP7, BDNF, UNCB5, SOSTDC1, OLIG1, PLAT, KCNJ10, SHH, NTN1, GDNF, ERBB3, GAP43, SOX10, S100, GFAP, POU3F1, PMP22, MBP, AQP4, MPZ, NGFR, NFATC4, MOG, IFNG, MAL, NTF3, TGFB1, CD9, CD81, CD44, CD98, CD49E, CD49D, TYRP1, ENTHD1, NT5E, HTR2B, NOV, IL8, SLC16A6, CDKN2A, PLP2, S100A6, AQP9, and CDH19. In certain embodiments, the one or more SC marker is slected from the genes listed in Tables 1-4. In certain embodiments, the one or more SC marker is slected from the genes listed in Tables 2-4. In certain embodiments, the one or more SC marker is selected from the group consisting of TYRP1, CD44, ENTHD1, NT5E, HTR2B, NOV, IL8, SLC16A6, and CDKN2A.

The presently disclosed subject matter also provides for a population of in vitro differentiated cells expressing one or more Schwann cell precursor marker. In certain embodiments, the population of differentiated cells expressing one or more Schwann cell precursor marker is derived from a stem cell population by the in vitro differentiation method described herein.

In certain embodiments, the population of differentiated cells expressing one or more Schwann cell precursor marker is derived from a stem cell population after: contacting a stem cell population with one or more inhibitor of TGFβ/Activin-Nodal signaling, and one or more Wnt activator, and further contacting the cells with one or more FGF activator for at least about 3 days (e.g., at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days; between about 10 days and about 20 days or between about 10 days and about 15 days).

In certain embodiments, the population of differentiated cells expressing one or more Schwann cell precursor marker is derived from a stem cell population after further contacting the cells with one or more SC differentiation inducer for at least about 3 days (e.g., at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days; between about 10 days and about 20 days or between about 10 days and about 15 days).

In certain embodiments, the population of differentiated cells expressing one or more Schwann cell precursor marker is derived from a stem cell population after: contacting a stem cell population with one or more inhibitor of TGFβ/Activin-Nodal signaling, and one or more Wnt activator, and further contacting the cells with one or more FGF activator, wherein the initial contact of the one or more FGF activator with the cells is no later than about 20 days (e.g., between about 10 days and about 15 days, e.g., 10 days or 11 days) from the initial contact of the stem cells with the one or more inhibitor of TGFβ/Activin-Nodal signaling.

In certain embodiments, the population of differentiated cells expressing one or more Schwann cell precursor marker is derived from a stem cell population after: further contacting the cells with one or more SC differentiation inducer, wherein the initial contact of the one or more SC differentiation inducer with the cells is no later than about 20 days (e.g., between about 10 days and about 15 days, e.g., 10 days or 11 days) from the initial contact of the stem cells with the one or more inhibitor of TGFβ/Activin-Nodal signaling.

In certain embodiments, the population of differentiated cells expressing one or more Schwann cell precursor marker is derived from a stem cell population after contacting a stem cell population with one or more inhibitor of TGFβ/Activin-Nodal signaling, and one or more Wnt activator, and further contacting the cells with one or more FGF activator and one or more SC differentiation inducer simultaneously and/or concurrently.

The presently disclosed subject matter further provides for compositions comprising such differentiated cells expressing one or more Schwann cell precursor marker.

The presently disclosed subject matter also provides for a population of in vitro differentiated cells expressing one or more Schwann cell marker. In certain embodiments, the differentiated cell population is derived from the population of differentiated cells expressing one or more Schwann cell precursor marker by the in vitro differentiation method described herein.

In certain embodiments, the differentiated cell population expressing one or more Schwann cell marker is derived from the population of differentiated cells expressing one or more Schwann cell precursor marker after: contacting the population of differentiated cells expressing one or more Schwann cell precursor marker with one or more FGF activator and one or more Schwann cell differentiation inducer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days.

In certain embodiments, the differentiated cell population expressing one or more Schwann cell marker is derived from the population of differentiated cells expressing one or more Schwann cell precursor marker after further contacting the population of differentiated cells expressing one or more Schwann cell precursor marker with one or more SC differentiation enhancer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days.

In certain embodiments, the differentiated cell population expressing one or more Schwann cell marker is derived from the population of differentiated cells expressing one or more Schwann cell precursor marker after further contacting the population of differentiated cells expressing one or more Schwann cell precursor marker with one or more FGF activator, one or more SC differentiation inducer, and one or more SC differentiation enhancer simultaneously for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days.

The presently disclosed subject matter further provides for compositions comprising such population of differentiated cells expressing one or more Schwann cell marker.

Furthermore, the presently disclosed subject matter provides for kits for inducing differentiation of stem cells. In certain embodiments, the kit comprises one or more inhibitor of TGFβ/Activin-Nodal signaling, one or more Wnt activator, and one or more FGF activator. In certain embodiments, the kit comprises instructions for inducing differentiation of the stem cells into a population of differentiated cells that express one or more Schwann cell precursor marker. In certain embodiments, the instructions comprise contacting the cells with the one or more FGF activator for at least about 3 days (e.g., at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days; between about 10 days and about 20 days or between about 10 days and about 15 days).

In certain embodiments, the instructions comprise initially contacting the one or more FGF activator with the cells no later than about 20 days (e.g., 10 days or 11 days) from the initial contact of the stem cells with the one or more inhibitor of TGFβ/Activin-Nodal signaling.

In certain embodiments, the kit further comprises one or more SC differentiation inducer. In certain embodiments, the instructions further comprise contacting the cells with the one or more SC differentiation inducer for at least about 3 days (e.g., at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days; between about 10 days and about 20 days or between about 10 days and about 15 days). In certain embodiments, the instructions comprise contacting the cells with the one or more FGF activator and one or more SC differentiation inducer simultaneously and/or concurrently.

In certain embodiments, the kit further comprises one or more SMAD inhibitor. In certain embodiments, the instructions further comprise contacting the stem cells with the one or more inhibitor of TGFβ/Activin-Nodal signaling and the SMAD inhibitor concurrently.

In certain embodiments, the kit further comprises instructions for inducing maturation of the population of differentiated Schwann cell precursors into a population of cells that express one or more Schwann cell marker. In certain embodiments, the instructions comprise contacting the population of differentiated Schwann cell precursors with the one or more FGF activator and the one or more Schwann cell differentiation inducer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days. In certain embodiments, the instructions comprise contacting the population of differentiated Schwann cell precursors with the one or more FGF activator and the one or more Schwann cell differentiation inducer for about 10 days. In certain embodiments, the instructions comprise contacting the population of differentiated Schwann cell precursors with the one or more FGF activator and the one or more Schwann cell differentiation inducer for about 11 days. In certain embodiments, the instructions comprise contacting the population of differentiated Schwann cell precursors with the one or more FGF activator and the one or more Schwann cell differentiation inducer for 35 days.

In certain embodiments, the kit for inducing maturation of the population of differentiated Schwann cell precursors into a population of cells that express one or more Schwann cell marker further comprises one or more SC differentiation enhancer. In certain embodiments, the instructions for inducing maturation of the population of differentiated Schwann cell precursors into a population of cells that express one or more Schwann cell marker comprise further contacting the population of differentiated Schwann cell precursors with the one or more SC differentiation enhancer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days. In certain embodiments, the instructions comprise contacting the population of differentiated Schwann cell precursors with the one or more SC differentiation enhancer for about 10 days. In certain embodiments, the instructions for inducing maturation of the population of differentiated Schwann cell precursors into a population of cells that express one or more Schwann cell marker comprise contacting the population of differentiated Schwann cell precursors with the one or more SC differentiation enhancer for about 11 days. In certain embodiments, the instructions for inducing maturation of the population of differentiated Schwann cell precursors into a population of cells that express one or more Schwann cell marker comprise contacting the population of differentiated Schwann cell precursors with the one or more SC differentiation enhancer for about 35 days. In certain embodiments, the instructions for inducing maturation of the population of differentiated Schwann cell precursors into a population of cells that express one or more Schwann cell marker comprise contacting the population of differentiated Schwann cell precursors with the one or more FGF activator, the one or more Schwann cell differentiation inducer, and the one or more SC differentiation enhancer simultaneously and/or concurrently.

In certain embodiments, the stem cell population is differentiated into a population of differentiated cells that express one or more Schwann cell precursor marker on or after about 25 days from the initial contact of the stem cells with the one or more inhibitor of TGFβ/Activin-Nodal signaling.

In certain embodiments, the stem cell population is differentiated into a population of Schwann cells on or after about 35 days from the initial contact of the stem cells with the one or more inhibitor of TGFβ/Activin-Nodal signaling.

In certain embodiments, the population of differentiated Schwann cell precursors is differentiated into a population of Schwann cells on or after about 10 days from the initial contact of the differentiated cells that express one or more Schwann cell marker with one or both of the one or more FGF activator and the one or more Schwann cell differentiation inducer.

In certain embodiments, the one or more inhibitor of TGFβ/Activin-Nodal signaling is a small molecule selected from the group consisting of SB431542, derivatives thereof, and mixtures thereof. In certain embodiments, the one or more inhibitor of TGFβ/Activin-Nodal signaling is SB431542.

In certain embodiments, the one or more SMAD inhibitor is a small molecule selected from the group consisting of LDN193189, derivatives thereof, and mixtures thereof. In certain embodiments, the one or more SMAD inhibitor is LDN193189.

In certain embodiments, the one or more Wnt activator lowers glycogen synthase kinase 3β(GSK3β) for activation of Wnt signaling. In certain embodiments, the one or more Wnt activator is a small molecule selected from the group consisting of CHIR99021 and WNT3A, derivatives thereof, and mixtures thereof. In certain embodiments, the one or more Wnt activator is CHIR99021.

In certain embodiments, the one or more Schwann cell differentiation inducer is selected from the group consisting of neuregulins, LIF, CNTF, Forskolin, TGFβ, FBS and a combination thereof. In certain embodiments, the one Schwann cell differentiation inducer is Neuregulin 1 (NRG1).

In certain embodiments, the SC differentiation enhancer is selected from the group consisting of neuregulins cyclic adenosine monophosphate (cAMP), Forskolin, LIF, and CNTF.

In certain embodiments, the one or more FGF activator is selected from the group consisting of FGF1, FGF2, FGF3, FGF4, FGF7, FGF8, FGF10, FGF18, derivatives, and mixtures thereof. In certain embodiments, the one or more FGF activator is FGF2.

In certain embodiments, the stem cell is a human stem cell. In certain embodiments, the human stem cells are human pluripotent stem cells. In certain embodiments, the human pluripotent stem cells are selected from the group consisting of human embryonic stem cells, and human induced pluripotent stem cells. In certain embodiments, the stem cells are non-human stem cells, for example, but not limited to, mammalian stem cells, primate stem cells, or stem cells from a rodent, a mouse, a rat, a dog, a cat, a horse, a pig, a cow, a sheep, etc.

The presently disclosed subject matter further provides methods of preventing and/or treating A Schwann cell related disorder is peripheral neuropathy. In certain embodiments, the peripheral neuropathy is Diabetic Peripheral Neuropathy. In certain embodiments, the method comprises administering an effective amount of the differentiated Schwann cell precursors or a composition comprising thereof described herein to a subject suffering from peripheral neuropathy. In certain embodiments, the method comprises administering an effective amount of the differentiated Schwann cells or a composition comprising thereof described herein to a subject suffering from peripheral neuropathy.

The presently disclosed subject matter further provides the differentiated Schwann cell precursors or a composition comprising thereof described herein for treating peripheral neuropathy in a subject. In addition, the presently disclosed subject matter provides the differentiated Schwann cells or a composition comprising thereof described herein for treating peripheral neuropathy in a subject.

The presently disclosed subject matter further provides uses of the differentiated Schwann cell precursors or a composition comprising thereof described herein in the manufacture of a medicament for treating peripheral neuropathy. In addition, the presently disclosed subject matter provides uses of the differentiated Schwann cells or a composition comprising thereof described herein in the manufacture of a medicament for treating peripheral neuropathy.

A. In certain non-limiting embodiments, the presently disclosed subject matter provides an in vitro method for inducing differentiation of stem cells, comprising contacting a population of stem cells with one or more inhibitor of TGFβ/Activin-Nodal signaling and one or more Wnt activator, and further contacting said cells with one or more FGF activator for at least about 3 days to produce a population of differentiated cells that express one or more Schwann cell precursor marker.

A1. The foregoing method of A, comprising contacting said cells with said one or more FGF activator for about 14 days.

A2. The foregoing method of A, wherein initial contact of said cells with said one or more FGF activator is no later than about 20 days from the initial contact of said stem cells with said one or more inhibitor of TGFβ/Activin-Nodal signaling.

A3. The foregoing method of A, wherein the initial contact of said cells with said one or more FGF activator is between about 10 days and about 15 days from the initial contact of said stem cells with said one or more one or more inhibitor of TGFβ/Activin-Nodal signaling.

A4. The foregoing method of A, wherein the initial contact of said cells with said one or more FGF activator is about 11 days from the initial contact of said stem cells with said one or more one or more inhibitor of TGFβ/Activin-Nodal signaling.

A5. The foregoing method of A, further comprising contacting said cells with one or more SC differentiation inducer.

A6. The foregoing method of A, comprising contacting said cells with said one or more SC differentiation inducer for at least about 3 days to produce a population of differentiated cells that express one or more Schwann cell precursor marker.

A7. The foregoing method of A, comprising contacting said cells with said one or more SC differentiation inducer for about 14 days.

A8. The foregoing method of A, wherein the initial contact of said cells with said one or more SC differentiation inducer is between about 10 days and about 15 days from the initial contact of said stem cells with said one or more one or more inhibitor of TGFβ/Activin-Nodal signaling.

A9. The foregoing method of A, comprising contacting said cells with said one or more FGF activator and said one or more SC differentiation inducer concurrently.

A10. The foregoing method of A, wherein said population of stem cells are differentiated into a population of differentiated cells that express one or more said Schwann cell precursor marker on or after about 25 days from the initial contact of said stem cells with said one or more inhibitor of TGFβ/Activin-Nodal signaling.

A11. The foregoing method of A, further comprising contacting said stem cells with one or more SMAD inhibitor.

A12. The foregoing method of A, comprising contacting said stem cells with said one or more inhibitor of TGFβ/Activin-Nodal signaling and said one or more SMAD inhibitor concurrently.

A13. The foregoing method of A, wherein the initial contact of said cells with said one or more Wnt activator is no later than about 4 days from the initial contact of said stem cells with said one or more inhibitor of TGFβ/Activin-Nodal signaling.

A14. The foregoing method of A, wherein the initial contact of said cells with said one or more activator of Wnt signaling is about 2 days from the initial contact of said stem cells with said one or more inhibitor of TGFβ/Activin-Nodal signaling.

A15. The foregoing method of A, wherein the initial contact of said cells with said one or more activator of Wnt signaling is the same day as the initial contact of said stem cells with said one or more inhibitor of TGFβ/Activin-Nodal signaling.

A16. The foregoing method of A, wherein said one or more inhibitor of TGFβ/Activin-Nodal signaling is a small molecule selected from the group consisting of SB431542, derivatives thereof, and mixtures thereof.

A17. The foregoing method of A, wherein said one or more inhibitor of TGFβ/Activin-Nodal signaling is SB431542.

A18. The foregoing method of A, wherein said one or more SMAD inhibitor is a small molecule selected from the group consisting of LDN193189, derivatives thereof, and mixtures thereof.

A19. The foregoing method of A, wherein said one or more SMAD inhibitor is a LDN193189.

A20. The foregoing method of A, wherein said one or more Wnt activator lowers glycogen synthase kinase 3β (GSK3β) for activation of Wnt signaling.

A21. The foregoing method of A, wherein said one or more Wnt activator is a small molecule selected from the group consisting of CHIR99021, derivatives thereof, and mixtures thereof.

A22. The foregoing method of A, wherein said one or more Wnt activator is CHIR99021.

A23. The foregoing method of A, wherein said one or more SC differentiation inducer is selected from the group consisting of neuregulins, LIF, CNTF, Forskolin, TGFβ and FBS.

A24. The foregoing method of A, wherein said one or more SC differentiation inducer is NRG1.

A25. The foregoing method of A, wherein said one or more FGF activator is selected from the group consisting of FGF1, FGF2, FGF3, FGF4, FGF7, FGF8, FGF10, FGF18, derivatives, and mixtures thereof.

A26. The foregoing method of A, wherein said one or more FGF activator is FGF2.

A27. The foregoing method of A, wherein said one or more Schwann cell precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

A28. The foregoing method of A, wherein said stem cells are human stem cells.

A29. The foregoing method of A, wherein said human stem cells are selected from the group consisting of human embryonic stem cells, human induced pluripotent stem cells, human parthenogenetic stem cells, primordial germ cell-like pluripotent stem cells, epiblast stem cells, F-class pluripotent stem cells.

A30. The foregoing method of A, comprising subjecting said population of differentiated cells to conditions favoring maturation of said differentiated cells into a population of Schwann cells.

A31. The foregoing method of A, wherein said conditions favoring maturation of said differentiated cells into said population of Schwann cells comprise: contacting said differentiated cells with one or more FGF activator, and one or more Schwann cell differentiation inducer.

A32. The foregoing method of A, comprising contacting the population of differentiated SC precursor cells with the one or more FGF activator and the one or more Schwann cell differentiation inducer for at least about 3 days.

A33. The foregoing method of A, comprising contacting the population of differentiated SC precursor cells with the one or more FGF activator and the one or more Schwann cell differentiation inducer for 10 days.

A34. The foregoing method of A, comprising contacting the population of differentiated SC precursor cells with the one or more FGF activator and the one or more Schwann cell differentiation inducer for 35 days.

A35. The foregoing method of A, further comprising contacting the population of differentiated SC precursor cells with one or more SC differentiation enhancer.

A36. The foregoing method of A, comprising contacting the population of differentiated SC precursor cells with the one or more SC differentiation enhancer for at least about 3 days.

A37. The foregoing method of A, comprising contacting the population of differentiated SC precursor cells with the one or more SC differentiation enhancer for about 10 days.

A38. The foregoing method of A, comprising contacting the population of differentiated SC precursor cells with the one or more SC differentiation enhancer for about 35 days.

A39. The foregoing method of A, comprising contacting the population of differentiated SC precursor cells with the one or more FGF activator, the one or more Schwann cell differentiation inducer, and the one or more SC differentiation enhancer concurrently.

A40. The foregoing method of A, wherein said conditions favoring maturation of said differentiated cells into said population of Schwann cells comprise: further contacting said differentiated cells with one or more SC differentiation enhancer.

A41. The foregoing method of A, wherein said one or more SC differentiation enhancer is selected from the group consisting of neuregulins, cyclic adenosine monophosphate (cAMP), Forskolin, LIF, and CNTF.

A42. The foregoing method of A, wherein said one or more SC differentiation enhancer is cAMP.

A43. The foregoing method of A, comprising aggregating said population of differentiated cells into 3D spheroids; and contacting said 3D spheroids with said one or more FGF activator, and said one or more Schwann cell differentiation inducer.

A44. The foregoing method of A, further comprising culturing said 3D spheroids in adherent culture.

A45. The foregoing method of A, wherein said population of Schwann cells express one or more Schwann cell marker.

A46. The foregoing method of A, wherein said one or more Schwann cell marker is selected from the group consisting of Schwann cell marker is selected from the group consisting of LRRTM4, CDH1, FABP7, BDNF, UNCB5, SOSTDC1, OLIG1, PLAT, KCNJ10, SHH, NTN1, GDNF, ERBB3, GAP43, SOX10, S100, GFAP, POU3F1, PMP22, MBP, AQP4, MPZ, NGFR, NFATC4, MOG, IFNG, MAL, NTF3, TGFB1, CD9, CD81, CD44, CD98, CD49E, CD49D, TYRP1, ENTHD1, NT5E, HTR2B, NOV, IL8, SLC16A6, CDKN2A, PLP2, S100A6, AQP9, and CDH19.

B. In certain embodiments, the presently disclosed subject matter provides a population of in vitro differentiated cells expressing one or more Schwann cell precursor marker, wherein said differentiated cell population is derived from a population of stem cells after:

contacting a population of stem cells with one or more inhibitor of TGFβ/Activin-Nodal signaling and one or more Wnt activator, and further contacting said cells with one or more FGF activator for at least about 3 days.

B1. The foregoing differentiated cell population of B, wherein said cells are contacted with said one or more FGF activator for 14 days.

B2. The foregoing differentiated cell population of B, wherein the initial contact of said cells with said one or more FGF activator is no later than about 20 days from the initial contact of said stem cells with said one or more one or more inhibitor of TGFβ/Activin-Nodal signaling.

B3. The foregoing differentiated cell population of B, wherein the initial contact of said cells with said one or more FGF activator is between about 10 days and about 15 days from the initial contact of said stem cells with said one or more one or more inhibitor of TGFβ/Activin-Nodal signaling.

B4. The foregoing differentiated cell population of B, wherein the initial contact of said cells with said one or more FGF activator is about 11 days from the initial contact of said stem cells with said one or more one or more inhibitor of TGFβ/Activin-Nodal signaling.

B5. The foregoing differentiated cell population of B, wherein said cells are further contacted with one or more SC differentiation inducer.

B6. The foregoing differentiated cell population of B, wherein said cells are further contacted with said one or more SC differentiation inducer for at least about 3 days.

B7. The foregoing differentiated cell population of B, wherein the initial contact of said cells with said with said one or more SC differentiation inducer is between about 10 days and about 15 days from the initial contact of said stem cells with said one or more one or more inhibitor of TGFβ/Activin-Nodal signaling.

B8. The foregoing differentiated cell population of B, wherein said cells are further contacted with said one or more Wnt activator, said one or more FGF activator, and said one or more SC differentiation inducer concurrently.

B9. The foregoing differentiated cell population of B, wherein said population of stem cells are differentiated into a population of differentiated cells that express one or more said Schwann cell precursor marker on or after about 25 days from the initial contact of said stem cells with said one or more inhibitor of TGFβ/Activin-Nodal signaling.

B10. The foregoing differentiated cell population of B, wherein said stem cells are further contacted with one or more SMAD inhibitor.

B11. The foregoing differentiated cell population of B, wherein said stem cells are contacted with said one or more inhibitor of TGFβ/Activin-Nodal signaling and said one or more SMAD inhibitor concurrently.

B12. The foregoing differentiated cell population of B, wherein the initial contact of said cells with said one or more Wnt activator of signaling is no later than about 4 days from the initial contact of said population of stem cells with said one or more inhibitor of TGFβ/Activin-Nodal signaling.

B13. The foregoing differentiated cell population of B, wherein the initial contact of said cells with said one or more Wnt activator of signaling is about 2 days from the initial contact of said population of stem cells with said one or more inhibitor of TGFβ/Activin-Nodal signaling.

B14. The foregoing differentiated cell population of B, wherein the initial contact of said population of stem cells with said one or more Wnt activator of signaling is the same day as the initial contact of said stem cells with said one or more inhibitor of TGFβ/Activin-Nodal signaling.

B15. The foregoing differentiated cell population of B, wherein said one or more inhibitor of TGFβ/Activin-Nodal signaling is a small molecule selected from the group consisting of SB431542, derivatives thereof, and mixtures thereof.

B16. The foregoing differentiated cell population of B, wherein said one or more inhibitor of TGFβ/Activin-Nodal signaling is SB431542.

B17. The foregoing differentiated cell population of B, wherein said one or more SMAD inhibitor is a small molecule selected from the group consisting of LDN193189, derivatives thereof, and mixtures thereof.

B18. The foregoing differentiated cell population of B, wherein said one or more SMAD inhibitor is LDN193189.

B19. The foregoing differentiated cell population of B, wherein said one or more Wnt activator lowers glycogen synthase kinase 3β (GSK3β) for activation of Wnt signaling.

B20. The foregoing differentiated cell population of B, wherein said one or more Wnt activator is a small molecule selected from the group consisting of CHIR99021, derivatives thereof, and mixtures thereof.

B21. The foregoing differentiated cell population of B, wherein said one or more Wnt activator is CHIR99021.

B22. The foregoing differentiated cell population of B, wherein said one or more SC differentiation inducer is selected from the group consisting of neuregulins, LIF, CNTF, Forskolin, TGFβ and FBS.

B23. The foregoing differentiated cell population of B, wherein said one or more SC differentiation inducer is NRG1.

B24. The foregoing differentiated cell population of B, wherein said one or more FGF activator is selected from the group consisting of FGF1, FGF2, FGF3, FGF4, FGF7, FGF8, FGF10, FGF18, derivatives, and mixtures thereof.

B25. The foregoing differentiated cell population of B, wherein said one FGF activator is FGF2.

B26. The foregoing differentiated cell population of B, wherein said one or more Schwann cell precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

B27. The foregoing differentiated cell population of B, wherein said stem cells are human stem cells.

B28. The foregoing differentiated cell population of B, wherein said human stem cells are selected from the group consisting of human embryonic stem cells, human induced pluripotent stem cells, human parthenogenetic stem cells, primordial germ cell-like pluripotent stem cells, epiblast stem cells, and F-class pluripotent stem cells.

C. In certain embodiments, the presently disclosed subject matter provides a population of in vitro differentiated cells expressing one or more Schwann cell marker, wherein said differentiated cell population is derived from the foregoing population of cells expressing one or more Schwann cell precursor marker after:

- contacting the foregoing population of cells expressing one or more Schwann cell precursor marker with one or more FGF activator, and one or more Schwann cell differentiation inducer.

C1. The foregoing differentiated cell population of C, wherein said differentiated cell population is derived from the foregoing population of cells expressing one or more Schwann cell precursor marker after further contacting the foregoing population of cells expressing one or more Schwann cell precursor marker with one or more SC differentiation enhancer.

C2. The foregoing differentiated cell population of C, wherein said one or more SC differentiation enhancer is selected from the group consisting of neuregulins, cyclic adenosine monophosphate (cAMP), Forskolin, LIF, and CNTF.

C3. The foregoing differentiated cell population of C, wherein said one or more SC differentiation enhancer is cAMP.

C4. The foregoing differentiated cell population of C, said foregoing population of cells expressing one or more Schwann cell precursor marker are contacted with the one or more FGF activator and the one or more Schwann cell differentiation inducer for at least about 3 days.

C5. The foregoing differentiated cell population of C, said foregoing population of cells expressing one or more Schwann cell precursor marker are contacted with the one or more FGF activator and the one or more Schwann cell differentiation inducer for about 10 days.

C6. The foregoing differentiated cell population of C, said foregoing population of cells expressing one or more Schwann cell precursor marker are contacted with the one or more FGF activator and the one or more Schwann cell differentiation inducer for about 35 days.

C7. The foregoing differentiated cell population of C, said foregoing population of cells expressing one or more Schwann cell precursor marker are contacted with the one or more SC differentiation enhancer for at least about 3 days.

C8. The foregoing differentiated cell population of C, said foregoing population of cells expressing one or more Schwann cell precursor marker are contacted with the one or more SC differentiation enhancer for about 10 days.

C9. The foregoing differentiated cell population of C, said foregoing population of cells expressing one or more Schwann cell precursor marker are contacted with the one or more SC differentiation enhancer for about 35 days.

C10. The foregoing differentiated cell population of C, wherein said one or more Schwann cell marker is selected from the group consisting of Schwann cell marker is selected from the group consisting of LRRTM4, CDH1, FABP7, BDNF, UNCB5, SOSTDC1, OLIG1, PLAT, KCNJ10, SHH, NTN1, GDNF, ERBB3, GAP43, SOX10, S100, GFAP, POU3F1, PMP22, MBP, AQP4, MPZ, NGFR, NFATC4, MOG, IFNG, MAL, NTF3, TGFB1, CD9, CD81, CD44, CD98, CD49E, CD49D, TYRP1, ENTHD1, NT5E, HTR2B, NOV, IL8, SLC16A6, CDKN2A, PLP2, S100A6, AQP9, and CDH19.

D. In certain embodiments, the presently disclosed subject matter provides a composition comprising the foregoing population of differentiated Schwann cell precursors.

E. In certain embodiments, the presently disclosed subject matter provides a composition comprising the foregoing population of Schwann cells.

F. In certain embodiments, the presently disclosed subject matter provides a method of preventing and/or treating a Schwann cell related disorder in a subject, comprising administering to a subject suffering from a Schwann cell related disorder an effective amount of one of the followings:

(a) the foregoing population of differentiated Schwann cell precursors;
(b) a composition comprising the foregoing population of differentiated Schwann cell precursors;
(c) the foregoing population of Schwann cells; and
(d) a composition comprising the foregoing population of Schwann cells.

F1. The foregoing method of F, wherein the Schwann cell related disorder is peripheral neuropathy.

F2. The foregoing method of F, wherein the peripheral neuropathy is diabetic peripheral neuropathy.

G. In certain embodiments, the presently disclosed subject matter provides the foregoing population of differentiated Schwann cell precursors for preventing and/or treating a Schwann cell related disorder in a subject.

G1. The foregoing population of differentiated Schwann cell precursors of G, wherein the Schwann cell related disorder is peripheral neuropathy.

G2. The foregoing population of differentiated Schwann cell precursors of G, wherein the peripheral neuropathy is diabetic peripheral neuropathy.

H. In certain embodiments, the presently disclosed subject matter provides a composition comprising the foregoing population of differentiated Schwann cell precursors for preventing and/or treating a Schwann cell related disorder in a subject.

H1. The foregoing composition of H, wherein the Schwann cell related disorder is peripheral neuropathy.

H2. The foregoing composition of H, wherein the peripheral neuropathy is diabetic peripheral neuropathy.

I. In certain embodiments, the presently disclosed subject matter provides the foregoing population of Schwann cells for preventing and/or treating a Schwann cell related disorder in a subj ect.

I1. The foregoing population of Schwann cell of I, wherein the Schwann cell related disorder is peripheral neuropathy.

I2. The foregoing population of Schwann cell of I, wherein the peripheral neuropathy is diabetic peripheral neuropathy.

J. In certain embodiments, the presently disclosed subject matter provides a composition comprising the foregoing population of Schwann cells for preventing and/or treating a Schwann cell related disorder in a subject.

J1. The foregoing composition of J, wherein the Schwann cell related disorder is peripheral neuropathy.

J2. The foregoing composition of J, wherein the peripheral neuropathy is diabetic peripheral neuropathy.

K. In certain embodiments, the presently disclosed subject matter provides use of the foregoing population of differentiated Schwann cell precursors in the manufacture of a medicament for preventing and/or treating a Schwann cell related disorder.

K1. The foregoing use of K, wherein the Schwann cell related disorder is peripheral neuropathy.

K2. The foregoing use of K, wherein the peripheral neuropathy is diabetic peripheral neuropathy.

L. In certain embodiments, the presently disclosed subject matter provides use of a composition the foregoing population of differentiated Schwann cell precursors in the manufacture of a medicament for preventing and/or treating a Schwann cell related disorder.

L1. The foregoing use of L, wherein the Schwann cell related disorder is peripheral neuropathy.

L2. The foregoing use of L, wherein the peripheral neuropathy is diabetic peripheral neuropathy.

M. In certain embodiments, the presently disclosed subject matter provides use of the foregoing population of Schwann cells in the manufacture of a medicament for preventing and/or treating a Schwann cell related disorder.

M1. The foregoing use of M, wherein the Schwann cell related disorder is peripheral neuropathy.

M2. The foregoing use of M, wherein the peripheral neuropathy is diabetic peripheral neuropathy.

N. In certain embodiments, the presently disclosed subject matter provides use of a composition the foregoing population of Schwann cells in the manufacture of a medicament for preventing and/or treating a Schwann cell related disorder.

N1. The foregoing use of N, wherein the Schwann cell related disorder is peripheral neuropathy.

N2. The foregoing use of N, wherein the peripheral neuropathy is diabetic peripheral neuropathy.

P. In certain embodiments, the presently disclosed subject matter provides a kit for inducing differentiation of stem cells, comprising:

one or more inhibitor of TGFβ/Activin-Nodal signaling,
one or more Wnt activator, and
one or more FGF activator.

P1. The foregoing kit of P, comprising instructions for inducing differentiation of the stem cells into a population of differentiated cells that express one or more Schwann cell precursor marker, wherein said instructions comprise contacting said cells with said one or more FGF activator for at least about 3 days.

P2. The foregoing kit of P, wherein said instructions comprise contacting said cells with said one or more FGF activator for 14 days.

P3. The foregoing kit of P, wherein the initial contact of said cells with said one or more one or more FGF activator is no later than about 20 days from the initial contact of said stem cells with said one or more Wnt activator.

P4. The foregoing kit of P, wherein initial contact of said cells with said one or more one or more FGF activator is between about 10 days and about 15 days from the initial contact of said cells with said one or more Wnt activator.

P5. The foregoing kit of P, wherein the initial contact of said cells with said one or more one or more FGF activator is about 11 days from the initial contact of said cells with said one or more Wnt activator.

P6. The foregoing kit of P, further comprising the one or more SC differentiation inducer.

P7. The foregoing kit of P, wherein said instructions comprise further contacting said cells with said one or more SC differentiation inducer for at least about 3 days.

P8. The foregoing kit of P, wherein said instructions comprise further contacting said cells with said one or more SC differentiation inducer for about 14 days.

P9. The foregoing kit of P, wherein the initial contact of said cells with said one or more one or more SC differentiation inducer is between about 10 days and about 15 days from the initial contact of said cells with said one or more Wnt activator.

P10. The foregoing kit of P, wherein said instructions comprise contacting said cells with said one or more FGF activator and said one or more SC differentiation inducer concurrently.

P11. The foregoing kit of P, further comprising one or more SMAD inhibitor.

P12. The foregoing kit of P, wherein said instructions further comprise contacting said stem cells with said one or more inhibitor of TGFβ/Activin-Nodal signaling and said one or more SMAD inhibitor.

P13. The foregoing kit of P, wherein said instructions comprise contacting said stem cells with said one or more inhibitor of TGFβ/Activin-Nodal signaling and said one or more SMAD inhibitor concurrently.

P14. The foregoing kit of P, wherein said instructions comprise initially contacting said cells with said one or more Wnt activator no later than about 4 days from the initial contact of said stem cells with said one or more inhibitor of TGFβ/Activin-Nodal signaling.

P15. The foregoing kit of P, wherein said instructions comprise initially contacting said cells with said one or more Wnt activator about 2 days from the initial contact of said stem cells with said one or more inhibitor of TGFβ/Activin-Nodal signaling.

P16. The foregoing kit of P, wherein said instructions comprise initially contacting said stem cells with said one or more inhibitor of TGFβ/Activin-Nodal signaling on the same day as the initial contact of said cells with said one or more Wnt activator.

P17. The foregoing kit of P, wherein said one or more inhibitor of TGFβ/Activin-Nodal signaling is a small molecule selected from the group consisting of SB431542, derivatives thereof, and mixtures thereof.

P18. The foregoing kit of P, wherein said one or more inhibitor of TGFβ/Activin-Nodal signaling is SB431542.

P19. The foregoing kit of P, wherein said one or more SMAD inhibitor is a small molecule selected from the group consisting of LDN193189, derivatives thereof, and mixtures thereof.

P20. The foregoing kit of P, wherein said one or more SMAD inhibitor is LDN193189.

P21. The foregoing kit of P, wherein said one or more Wnt activator lowers glycogen synthase kinase 3β(GSK3β) for activation of Wnt signaling.

P22. The foregoing kit of P, wherein said one or more Wnt activator is a small molecule selected from the group consisting of CHIR99021, derivatives thereof, and mixtures thereof.

P23. The foregoing kit of P, wherein said one or more Wnt activator is CHIR99021.

P24. The foregoing kit of P, wherein said one or more SC differentiation inducer is selected from the group consisting of neuregulins, LIF, CNTF, Forskolin, TGFβ and FBS.

P25. The foregoing kit of P, wherein said one or more SC differentiation inducer is NRG1.

P26. The foregoing kit of P, wherein said one or more FGF activator is selected from the group consisting of FGF1, FGF2, FGF3, FGF4, FGF7, FGF8, FGF10, FGF18, derivatives, and mixtures thereof.

P27. The foregoing kit of P, wherein said one FGF activator is FGF2.

P28. The foregoing kit of P, further comprising one or more SC differentiation enhancer, and instructions for inducing maturation of said differentiated cells into a population of Schwann cells.

P29. The foregoing kit of P, wherein said one or more SC differentiation enhancer is selected from the group consisting of neuregulins, cyclic adenosine monophosphate (cAMP), Forskolin, LIF, and CNTF.

P30. The foregoing kit of P, wherein said one or more SC differentiation enhancer is cAMP.

P31. The foregoing kit of P, wherein said instructions for inducing maturation of said differentiated cells into a population of Schwann cells comprise: contacting said differentiated cells with said one or more FGF activator and said one or more Schwann cell differentiation inducer.

P32. The foregoing kit of P, wherein said instructions for inducing maturation of said differentiated cells into a population of Schwann cells comprise contacting said population of differentiated SC precursor cells with the one or more FGF activator and the one or more Schwann cell differentiation inducer for at least about 3 days.

P33. The foregoing kit of P, wherein said instructions for inducing maturation of said differentiated cells into a population of Schwann cells comprise contacting said population of differentiated SC precursor cells are contacted with the one or more FGF activator and the one or more Schwann cell differentiation inducer for about 10 days.

P34. The foregoing kit of P, wherein said instructions for inducing maturation of said differentiated cells into a population of Schwann cells comprise contacting said population of differentiated SC precursor cells are contacted with the one or more FGF activator and the one or more Schwann cell differentiation inducer for about 35 days.

P35. The foregoing kit of P, wherein said instructions for inducing maturation of said differentiated cells into a population of Schwann cells further comprise contacting the population of differentiated SC precursor cells with the one or more SC differentiation enhancer.

P36. The foregoing kit of P, wherein said instructions for inducing maturation of said differentiated cells into a population of Schwann cells further comprise contacting the population of differentiated SC precursor cells with the one or more SC differentiation enhancer for at least about 3 days.

P37. The foregoing kit of P, wherein said instructions for inducing maturation of said differentiated cells into a population of Schwann cells further comprise contacting the population of differentiated SC precursor cells with the one or more SC differentiation enhancer for about 14 days.

P38. The foregoing kit of P, wherein said instructions for inducing maturation of said differentiated cells into a population of Schwann cells further comprise contacting the population of differentiated SC precursor cells with the one or more SC differentiation enhancer for about 35 days.

P39. The foregoing kit of P, wherein said instructions for inducing maturation of said differentiated cells into a population of Schwann cells comprises contacting the population of differentiated SC precursor cells with the one or more FGF activator, the one or more Schwann cell differentiation inducer, and the one or more SC differentiation enhancer concurrently.

Q. In certain non-limiting embodiments, the presently disclosed subject matter provides an in vitro method for inducing differentiation of stem cells, comprising contacting a population of stem cells with one or more inhibitor of TGFβ/Activin-Nodal signaling, and contacting said cells with one or more Wnt activator, and further contacting said cells with one or more FGF activator for at least about 3 days, for between about 3 days and about 20 days, for between about 10 days and about 20 days or between about 10 days and about 15 days, to produce a population of differentiated cells that express one or more Schwann cell precursor marker, wherein the initial contact of said the one or more FGF activator with said cells is no later than about 10 days from the initial contact of the stem cells with the one or more inhibitor of TGFβ/Activin-Nodal signaling.

Q1. The foregoing method of Q, wherein the initial contact of said cells with said one or more Wnt activator is no later than about 4 days from the initial contact of said stem cells with said one or more inhibitor of TGFβ/Activin-Nodal signaling.

Q2. The foregoing method of Q, further comprising further contacting said cells with one or more SC differentiation inducer for at least about 3 days, for between about 3 days and about 20 days, for between about 10 days and about 20 days or between about 10 days and about 15 days, to produce a population of differentiated cells that express one or more Schwann cell precursor marker, wherein the initial contact of said the one or more SC differentiation inducer with the cells is no later than about 10 days from the initial contact of the stem cells with the one or more inhibitor of TGFβ/Activin-Nodal signaling.

Q3. The foregoing method of Q, further comprising further contacting said cells with one or more SC differentiation inducer and one or more FGF activator concurrently for at least about 3 days, for between about 3 days and about 20 days, for between about 10 days and about 20 days or between about 10 days and about 15 days, to produce a population of differentiated cells that express one or more Schwann cell precursor marker, wherein the initial contact of said the one or more SC differentiation inducer and one or more FGF activator with the cells is no later than about 10 days from the initial contact of the stem cells with the one or more inhibitor of TGFβ/Activin-Nodal signaling.

R. In certain non-limiting embodiments, the presently disclosed subject matter provides for a population of in vitro differentiated cells expressing one or more Schwann cell precursor marker, wherein said differentiated cell population is derived from a population of stem cells after: contacting a population of stem cells with one or more inhibitor of TGFβ/Activin-Nodal signaling, and contacting the cells with one or more Wnt activator, and further contacting said cells with one or more FGF activator for at least about 3 days, for between about 3 days and about 20 days, for between about 10 days and about 20 days or between about 10 days and about 15 days, wherein the initial contact of said one or more SC differentiation inducer and the one or more FGF activator with the cells is no later than about 20 days from the initial contact of the stem cells with the one or more inhibitor of TGFβ/Activin-Nodal signaling.

R1. The foregoing differentiated cell population of R, wherein the initial contact of said cells with said one or more Wnt activator is no later than about 4 days from the initial contact of said stem cells with said one or more inhibitor of TGFβ/Activin-Nodal signaling.

R2. The foregoing method of Q, further comprising further contacting said cells with one or more SC differentiation inducer for at least about 3 days, for between about 3 days and about 20 days, for between about 10 days and about 20 days or between about 10 days and about 15 days, wherein the initial contact of said one or more SC differentiation inducer with the cells is no later than about 10 days from the initial contact of the stem cells with the one or more inhibitor of TGFβ/Activin-Nodal signaling.

R3. The foregoing method of Q, further comprising further contacting said cells with one or more SC differentiation inducer and one or more FGF activator concurrently for at least about 3 days, for between about 3 days and about 20 days, for between about 10 days and about 20 days or between about 10 days and about 15 days, wherein the initial contact of said one or more SC differentiation inducer and one or more FGF activator with the cells is no later than about 10 days from the initial contact of the stem cells with the one or more inhibitor of TGFβ/Activin-Nodal signaling.

S. In certain non-limiting embodiments, the presently disclosed subject matter provides an in vitro method for inducing differentiation of neural crest lineage cells, comprising a population of cells that express one or more neural crest lineage marker with one or more Wnt activator, and one or more FGF activator to produce a population of cells that express one or more Schwann cell precursor marker.

S1. The foregoing method of S, wherein the method comprises contacting the population of cells that express one or more neural crest lineage marker with the one or more Wnt activator and one or more FGF activator for at least about 3 days.

S2. The foregoing method of S, wherein the method comprises contacting the population of cells that express one or more neural crest lineage marker with the one or more Wnt activator and one or more FGF activator for up to about 30 days.

S3. The foregoing method of S, wherein the method comprises contacting the population of cells that express one or more neural crest lineage marker with the one or more Wnt activator and one or more FGF activator for between about 5 days and about 15 days.

S4. The foregoing method of S, comprising contacting said population of cells that express one or more neural crest lineage marker with the one or more Wnt activator and one or more FGF activator for about 14 days.

S5. The foregoing method of S, wherein the method further comprises contacting the population of cells that express one or more neural crest lineage marker with one or more SC differentiation inducer.

S6. The foregoing method of S, wherein the method further comprises contacting the population of cells that express one or more neural crest lineage marker with the one or more SC differentiation inducer for at least about 3 days.

S7. The foregoing method of S, wherein the method further comprises contacting the population of cells that express one or more neural crest lineage marker with the one or more SC differentiation inducer for up to about 30 days.

S8. The foregoing method of S, wherein the method further comprises contacting the population of cells that express one or more neural crest lineage marker with the one or more SC differentiation inducer for about 14 days.

S9. The foregoing method of S, wherein the method further comprises contacting the population of cells that express one or more neural crest lineage marker with the one or more FGF activator, and one or more SC differentiation inducer concurrently.

S10. The foregoing method of S, wherein said one or more Wnt activator lowers glycogen synthase kinase 3β (GSK3β) for activation of Wnt signaling.

S11. The foregoing method of S, wherein said one or more Wnt activator is a small molecule selected from the group consisting of CHIR99021, Wnt-1, WNT3A, Wnt4, Wnt5a, derivatives thereof, and mixtures thereof.

S12. The foregoing method of S, wherein said one or more Wnt activator is CHIR99021.

S13. The foregoing method of S, wherein said one or more SC differentiation inducer is selected from the group consisting of neuregulins, LIF, CNTF, Forskolin, TGFβ and FBS.

S14. The foregoing method of S, wherein said one or more SC differentiation inducer is NRG1.

S15. The foregoing method of S, wherein said one or more FGF activator is selected from the group consisting of FGF1, FGF2, FGF3, FGF4, FGF7, FGF8, FGF10, FGF18, derivatives, and mixtures thereof.

S16. The foregoing method of S, wherein said one or more FGF activator is FGF2.

S17. The foregoing method of S, wherein said one or more Schwann cell precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

S18. The foregoing method of S, comprising subjecting said population of cells that express one or more Schwann cell precursor marker to conditions favoring maturation of said cells into a population of Schwann cells.

S19. The foregoing method of S, wherein said conditions comprise: contacting said population of cells that express one or more Schwann cell precursor marker with one or more FGF activator, and one or more Schwann cell differentiation inducer.

S20. The foregoing method of S, comprising contacting the population of cells that express one or more Schwann cell precursor marker with the one or more FGF activator and the one or more Schwann cell differentiation inducer for at least about 3 days.

S21. The foregoing method of S, comprising contacting the population of cells that express one or more Schwann cell precursor marker with the one or more FGF activator and the one or more Schwann cell differentiation inducer for about 10 days.

S22. The foregoing method of S, comprising contacting the population of cells that express one or more Schwann cell precursor marker with the one or more FGF activator and the one or more Schwann cell differentiation inducer for about 35 days.

S23. The foregoing method of S, wherein said conditions further comprise contacting said population of cells that express one or more Schwann cell precursor marker with one or more SC differentiation enhancer.

S24. The foregoing method of S, comprising further contacting the population of cells that express one or more Schwann cell precursor marker with the one or more SC differentiation enhancer for at least about 3 days.

S25. The foregoing method of S, comprising further contacting the population of cells that express one or more Schwann cell precursor marker with the one or more SC differentiation enhancer for at least about 10 days.

S26. The foregoing method of S, comprising further contacting the population of cells that express one or more Schwann cell precursor marker with the one or more SC differentiation enhancer for at least about 35 days.

S27. The foregoing method of S, wherein the method comprises contacting the population of cells that express one or more neural crest lineage marker with the one or more FGF activator and one or more SC differentiation enhancer concurrently.

S28. The foregoing method of S, wherein said one or more SC differentiation enhancer is selected from the group consisting of neuregulins, cyclic adenosine monophosphate (cAMP), Forskolin, LIF, and CNTF.

S29. The foregoing method of S, wherein said one or more SC differentiation enhancer is cAMP.

S30. The foregoing method of S, wherein said population of Schwann cells express one or more Schwann cell marker.

S31. The foregoing method of S, wherein said one or more Schwann cell marker is selected from the group consisting of Schwann cell marker is selected from the group consisting of LRRTM4, CDH1, FABP7, BDNF, UNCB5, SOSTDC1, OLIG1, PLAT, KCNJ10, SHH, NTN1, GDNF, ERBB3, GAP43, SOX10, S100, GFAP, POU3F1, PMP22, MBP, AQP4, MPZ, NGFR, NFATC4, MOG, IFNG, MAL, NTF3, TGFB1, CD9, CD81, CD44, CD98, CD49E, CD49D, TYRP1, ENTHD1, NT5E, HTR2B, NOV, IL8, SLC16A6, CDKN2A, PLP2, S100A6, AQP9, and CDH19.

S32. The foregoing method of S, wherein the neural crest lineage marker is selected from the group consisting of SOX10, p75, HNK1, CD49D, ERBB3, TFAP2, SNAIL and SLUG.

T. In certain non-limiting embodiments, the presently disclosed subject matter provides for a population of in vitro differentiated cells expressing one or more Schwann cell precursor marker, wherein said differentiated cell population is derived from a population of neural crest lineage cells after: contacting a population of cells that express one or more neural crest lineage marker with one or more Wnt activator, one or more FGF activator for at least about 3 days, for up to about 30 days, or for between about 5 days and about 15 days.

T1. The foregoing differentiated cell population of T, wherein said population of cells that express one or more neural crest lineage marker are contacted with said one or more Wnt activator and one or more FGF activator for about 14 days.

T2. The foregoing differentiated cell population of T, wherein said population of cells that express one or more neural crest lineage marker are further contacted with one or more SC differentiation inducer.

T3. The foregoing differentiated cell population of T, wherein said population of cells that express one or more neural crest lineage marker are further contacted with one or more SC differentiation inducer for at least about 3 days, for up to about 30 days, or for between about 5 days and about 15 days.

T4. The foregoing differentiated cell population of T, wherein said population of cells that express one or more neural crest lineage marker are further contacted with one or more SC differentiation inducer for about 14 days.

T5. The foregoing differentiated cell population of T, wherein said population of cells that express one or more neural crest lineage marker are contacted with one or more Wnt activator, one or more FGF activator, and one or more SC differentiation inducer simultaneously.

T6. The foregoing differentiated cell population of T, wherein said one or more Wnt activator lowers glycogen synthase kinase 3β(GSK3β) for activation of Wnt signaling.

T7. The foregoing differentiated cell population of T, wherein said one or more Wnt activator is a small molecule selected from the group consisting of CHIR99021, Wnt-1, WNT3A, Wnt4, Wnt5a, derivatives thereof, and mixtures thereof.

T8. The foregoing differentiated cell population of T, wherein said one or more Wnt activator is CHIR99021.

T9. The foregoing differentiated cell population of T, wherein said one or more SC differentiation inducer is selected from the group consisting of neuregulins, LIF, CNTF, Forskolin, TGFβ and FBS.

T10. The foregoing differentiated cell population of T, wherein said one or more SC differentiation inducer is NRG1.

T11. The foregoing differentiated cell population of T, wherein said one or more FGF activator is selected from the group consisting of FGF1, FGF2, FGF3, FGF4, FGF7, FGF8, FGF10, FGF18, derivatives, and mixtures thereof.

T12. The foregoing differentiated cell population of T, wherein said one FGF activator is FGF2.

T13. The foregoing differentiated cell population of T, wherein said one or more Schwann cell precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

T14. The foregoing method of T, wherein the neural crest lineage marker is selected from the group consisting of SOX10, p75, HNK1, CD49D, ERBB3, TFAP2, SNAIL and SLUG.

U. In certain embodiments, the in vitro method for inducing differentiation of stem cells comprises: in vitro differentiating a population of stem cells to a population of cells that express one or more neural crest lineage marker, and contacting the differentiated cells with one or more Wnt activator and one or more FGF activator to produce a population of cells that express one or more Schwann cell precursor marker.

U1. The foregoing method of U, wherein the method comprises contacting the population of cells that express one or more neural crest lineage marker with the one or more Wnt activator, one or more FGF activator for at least about 3 days.

U2. The foregoing method of U, wherein the method comprises contacting the population of cells that express one or more neural crest lineage marker with the one or more Wnt activator, one or more FGF activator for up to about 30 days.

U3. The foregoing method of U, wherein the method comprises contacting the differentiated cells with the one or more Wnt activator, one or more FGF activator for between about 5 days and about 15 days or between about 10 days and 15 days.

U4. The foregoing method of U, comprising contacting said population of cells that express one or more neural crest lineage marker with said one or more Wnt activator and one or more FGF activator for about 14 days.

U5. The foregoing method of U, wherein the method further comprises contacting the population of cells that express one or more neural crest lineage marker with one or more SC differentiation inducer.

U6. The foregoing method of U, wherein the method further comprises contacting the population of cells that express one or more neural crest lineage marker with one or more SC differentiation inducer for at least about 3 days.

U7. The foregoing method of U, wherein the method further comprises contacting the population of cells that express one or more neural crest lineage marker with one or more SC differentiation inducer for up to about 30 days.

U8. The foregoing method of U, wherein the method further comprises contacting the population of cells that express one or more neural crest lineage marker with one or more SC differentiation inducer for about 14 days.

U9. The foregoing method of U, wherein the method comprises contacting the population of cells that express one or more neural crest lineage marker with one or more Wnt activator, one or more FGF activator and one or more SC differentiation inducer concurrently to produce a population of cells that express one or more Schwann cell precursor marker.

U10. The foregoing method of U, wherein said one or more Wnt activator lowers glycogen synthase kinase 3β(GSK3β) for activation of Wnt signaling.

U11. The foregoing method of U, wherein said one or more Wnt activator is a small molecule selected from the group consisting of CHIR99021, Wnt-1, WNT3A, Wnt4, Wnt5a, derivatives thereof, and mixtures thereof.

U12. The foregoing method of U, wherein said one or more Wnt activator is CHIR99021.

U13. The foregoing method of U, wherein said one or more SC differentiation inducer is selected from the group consisting of neuregulins, LIF, CNTF, Forskolin, TGFβ and FBS.

U14. The foregoing method of U, wherein said one or more SC differentiation inducer is NRG1.

U15. The foregoing method of U, wherein said one or more FGF activator is selected from the group consisting of FGF1, FGF2, FGF3, FGF4, FGF7, FGF8, FGF10, FGF18, derivatives, and mixtures thereof.

U16. The foregoing method of U, wherein said one or more FGF activator is FGF2.

U17. The foregoing method of U, wherein said one or more Schwann cell precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

U18. The foregoing method of U, comprising subjecting said population of cells that express one or more Schwann cell precursor marker to conditions favoring maturation of said cells into a population of Schwann cells.

U19. The foregoing method of U, wherein said conditions comprise: contacting said population of cells that express one or more Schwann cell precursor marker with one or more FGF activator, and one or more Schwann cell differentiation inducer.

U20. The foregoing method of U, comprising contacting the population of cells that express one or more Schwann cell precursor marker with the one or more FGF activator and the one or more Schwann cell differentiation inducer for at least about 3 days.

U21. The foregoing method of U, comprising contacting the population of cells that express one or more Schwann cell precursor marker with the one or more FGF activator and the one or more Schwann cell differentiation inducer for about 10 days.

U22. The foregoing method of U, comprising contacting the population of cells that express one or more Schwann cell precursor marker with the one or more FGF activator and the one or more Schwann cell differentiation inducer for about 35 days.

U23. The foregoing method of U, wherein said conditions comprise further contacting said population of cells that express one or more Schwann cell precursor marker with one or more SC differentiation enhancer.

U24. The foregoing method of U, wherein said conditions comprise further contacting said population of cells that express one or more Schwann cell precursor marker with one or more SC differentiation enhancer for at least about 3 days.

U25. The foregoing method of U, wherein said conditions comprise further contacting said population of cells that express one or more Schwann cell precursor marker with one or more SC differentiation enhancer for about 10 days.

U26. The foregoing method of U, wherein said conditions comprise further contacting said population of cells that express one or more Schwann cell precursor marker with one or more SC differentiation enhancer for about 35 days.

U27. The foregoing method of U, wherein said conditions comprise contacting said population of cells that express one or more Schwann cell precursor marker with the one or more FGF activator, the one or more Schwann cell differentiation inducer, and the one or more SC differentiation enhancer simultaneously.

U28. The foregoing method of U, wherein said one or more SC differentiation enhancer is selected from the group consisting of neuregulins, cyclic adenosine monophosphate (cAMP), Forskolin, LIF, and CNTF.

U29. The foregoing method of U, wherein said one or more SC differentiation enhancer is cAMP.

U30. The foregoing method of U, wherein said population of Schwann cells express one or more Schwann cell marker.

U31. The foregoing method of U, wherein said one or more Schwann cell marker is selected from the group consisting of Schwann cell marker is selected from the group consisting of LRRTM4, CDH1, FABP7, BDNF, UNCB5, SOSTDC1, OLIG1, PLAT, KCNJ10, SHH, NTN1, GDNF, NGFR, NFATC4, MOG, IFNG, MAL, NTF3, TGFB1, SOX10, S100, GFAP, POU3F1, PMP22, MBP, AQP4, MPZ, GFAP, ERBB3, CD9, CD81, CD44, CD98, CD49E, CD49D, TYRP1, ENTHD1, NT5E, HTR2B, NOV, IL8, SLC16A6, CDKN2A, PLP2, S100A6, AQP9, and CDH19.

U32. The foregoing method of U, wherein the in vitro differentiation of the stem cell population to a population of cells that express one or more neural crest lineage marker comprises inhibiting SMAD signaling and activation of Wnt signaling.

U33. The foregoing method of U, the in vitro differentiating a stem cell population to a population of cells that express one or more neural crest lineage marker comprises contacting the stem cells with one or more inhibitor of TGFβ/Activin-Nodal signaling, and contacting the cells with one or more Wnt activator.

U34. The foregoing method of U, further comprising contacting said population of stem cells with one or more SMAD inhibitor.

U35. The foregoing method of U, comprising contacting said population of stem cells with said one or more inhibitor of TGFβ/Activin-Nodal signaling and said one or more SMAD inhibitor concurrently.

U36. The foregoing method of U, wherein the initial contact of said cells with said one or more Wnt activator is no later than about 4 days from the initial contact of said stem cells with said one or more inhibitor of TGFβ/Activin-Nodal signaling.

U37. The foregoing method of U, wherein the initial contact of said cells with said one or more activator of Wnt signaling is about 2 days from the initial contact of said stem cells with said one or more inhibitor of TGFβ/Activin-Nodal signaling.

U38. The foregoing method of U, wherein said one or more inhibitor of TGFβ/Activin-Nodal signaling is a small molecule selected from the group consisting of SB431542, derivatives thereof, and mixtures thereof.

U39. The foregoing method of U, wherein said one or more inhibitor of TGFβ/Activin-Nodal signaling is SB431542.

U40. The foregoing method of U, wherein said one or more SMAD inhibitor is a small molecule selected from the group consisting of LDN193189, derivatives thereof, and mixtures thereof.

U41. The foregoing method of U, wherein said one or more SMAD inhibitor is a LDN193189.

U42. The foregoing method of U, wherein the neural crest lineage marker is selected from the group consisting of SOX10, p75, HNK1, CD49D, ERBB3, TFAP2, SNAIL and SLUG.

V. In certain embodiments, the presently disclosed subject matter provides a method of regeneration of PNS and/or CNS in a subject, comprising administering to a subject an effective amount of one of the followings:

(a) the foregoing population of differentiated Schwann cell precursors;

(b) a composition comprising the foregoing population of differentiated Schwann cell precursors;

(c) the foregoing population of Schwann cells; and (d) a composition comprising the foregoing population of Schwann cells.

W. In certain embodiments, the presently disclosed subject matter provides the foregoing population of differentiated Schwann cell precursors for regeneration of PNS and/or CNS in a subject.

X. In certain embodiments, the presently disclosed subject matter provides a composition comprising the foregoing population of differentiated Schwann cell precursors for regeneration of PNS and/or CNS in a subject.

Y. In certain embodiments, the presently disclosed subject matter provides the foregoing population of Schwann cells for regeneration of PNS and/or CNS in a subject.

Z. In certain embodiments, the presently disclosed subject matter provides a composition comprising the foregoing population of Schwann cells for regeneration of PNS and/or CNS in a subject.

AA. In certain embodiments, the presently disclosed subject matter provides use of the foregoing population of differentiated Schwann cell precursors in the manufacture of a medicament for regeneration of PNS and/or CNS.

AB. In certain embodiments, the presently disclosed subject matter provides use of a composition the foregoing population of differentiated Schwann cell precursors in the manufacture of a medicament for regeneration of PNS and/or CNS.

AC. In certain embodiments, the presently disclosed subject matter provides use of the foregoing population of Schwann cells in the manufacture of a medicament for regeneration of PNS and/or CNS.

AD. In certain embodiments, the presently disclosed subject matter provides use of a composition the foregoing population of Schwann cells in the manufacture of a medicament for regeneration of PNS and/or CNS.

AE. In certain embodiments, the presently disclosed subject matter provides a method of preventing and/or treating myelin damage in a subject, comprising administering to a subject an effective amount of one of the followings:

(a) the foregoing population of differentiated Schwann cell precursors;

(b) a composition comprising the foregoing population of differentiated Schwann cell precursors;

(c) the foregoing population of Schwann cells; and (d) a composition comprising the foregoing population of Schwann cells.

AF. In certain embodiments, the presently disclosed subject matter provides the foregoing population of differentiated Schwann cell precursors for preventing and/or treating myelin damage in a subject.

AG. In certain embodiments, the presently disclosed subject matter provides a composition comprising the foregoing population of differentiated Schwann cell precursors for preventing and/or treating myelin damage in a subject.

AH. In certain embodiments, the presently disclosed subject matter provides the foregoing population of Schwann cells for preventing and/or treating myelin damage in a subject.

AI. In certain embodiments, the presently disclosed subject matter provides a composition comprising the foregoing population of Schwann cells for preventing and/or treating myelin damage in a subject.

AJ. In certain embodiments, the presently disclosed subject matter provides use of the foregoing population of differentiated Schwann cell precursors in the manufacture of a medicament for preventing and/or treating myelin damage.

AK. In certain embodiments, the presently disclosed subject matter provides use of a composition the foregoing population of differentiated Schwann cell precursors in the manufacture of a medicament for preventing and/or treating myelin damage.

AL. In certain embodiments, the presently disclosed subject matter provides use of the foregoing population of Schwann cells in the manufacture of a medicament for preventing and/or treating myelin damage.

AM. In certain embodiments, the presently disclosed subject matter provides use of a composition the foregoing population of Schwann cells in the manufacture of a medicament for preventing and/or treating myelin damage.

AU. In certain embodiments, the presently disclosed subject matter provides a composition comprising a population of in vitro differentiated cells, wherein at least about 50% (e.g., at least about 55%, at least about 60%, at least about 70%, at least about 75%, at least about 80%, at least about 85%, at least about 90%, at least about 95%, or at least about 99%) of the population of cells express one or more SC precursor marker, and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of stem cells markers, CNS markers, neuronal cell markers, and mesenchymal precursor markers.

AU1. The foregoing of the composition of AU, wherein the one or more SC precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

AU2. The foregoing of the composition of AU, wherein the stem cell markers are selected from the group consisting of OCT4, NANOG, SSEA4 and SSEA3. NAU1.

AU3. The foregoing of the composition of AU, wherein the CNS markers are selected from the group consisting of include PAX6, NESTIN, and SOX1.

AU4. The foregoing of the composition of AU, wherein the neuronal cell markers are selected from the group consisting of TUJ1, MAP2, NFH, BRN3A, ISL1, TH, ASCL1, CHAT, PHOX2B, PHOX2A, TRKA, TRKB, and TRKC.

AU5. The foregoing of the composition of AU, wherein the mesenchymal precursor markers are selected from the group consisting of SMA, and CD73.

AV. In certain embodiments, the presently disclosed subject matter provides a composition comprising a population of in vitro differentiated cells, wherein at least about 50% (e.g., at least about 55%, at least about 60%, at least about 70%, at least about 75%, at least about 80%, at least about 85%, at least about 90%, at least about 95%, or at least about 99%) of the population of cells express one or more SC marker, and wherein less than about 15% (e.g., less than about 10%, less than about 5%, less than about 4%, less than about 3%, less than about 2%, less than about 1%, less than about 0.5%, or less than about 0.1%) of cells express one or more marker selected from the group consisting of SC precursor markers, stem cells markers, CNS markers, neuronal cell markers, and mesenchymal precursor markers.

AV1. The foregoing of the composition of AV, wherein the one or more SC marker is selected from the group consisting of LRRTM4, CDH1, FABP7, BDNF, UNCB5, SOSTDC1, OLIG1, PLAT, KCNJ10, SHH, NTN1, GDNF, SOX10, S100, GFAP, POU3F1, PMP22, MBP, AQP4, MPZ, GFAP, ERBB3CD9, CD81, CD44, CD98, CD49E, CD49D, NGFR, NFATC4, MOG, IFNG, MAL, NTF3 TGFB1, TYRP1, ENTHD1, NT5E, HTR2B, NOV, IL8, SLC16A6, CDKN2A, PLP2, S100A6, AQP9, and CDH19

AV2. The foregoing of the composition of AV, wherein the SC precursor markers are selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

AV3. The foregoing of the composition of AV, wherein the stem cell markers are selected from the group consisting of OCT4, NANOG, SSEA4 and SSEA3. NAU1.

AV4. The foregoing of the composition of AU, wherein the CNS markers are selected from the group consisting of include PAX6, NESTIN, and SOX1.

AV5. The foregoing of the composition of AV, wherein the neuronal cell markers are selected from the group consisting of TUJ1, MAP2, NFH, BRN3A, ISL1, TH, ASCL1, CHAT, PHOX2B, PHOX2A, TRKA, TRKB, and TRKC.

AV6. The foregoing of the composition of AV, wherein the mesenchymal precursor markers are selected from the group consisting of SMA, and CD73.

BRIEF DESCRIPTION OF THE FIGURES

FIG. 1A shows schematic illustration of the protocol (day 11-35) for deriving Schwann cell precursors and Schwann cells. FIG. 1B shows SOX10::GFP expression at day 11, 25 and 35 of differentiation. FIGS. 1C and 1D show qRT-PCR for a panel of Schwann lineage markers involved in Schwann cell differentiation and myelination (FIG. 1C) and nerve interaction and support (FIG. 1D) Immunofluorescence of unsorted and CD49D sorted differentiated NC cells for SOX10. FIG. 1E shows representative immunofluorescence images of hESC-derived SCs for Schwann lineage markers at day 60. FIG. 1F shows quantification of markers in FIG. 1E. FIG. 1G shows principal component analysis of CD49d purified NC, CD49d purified SCP, human primary Schwann cells, and CD98 purified hESC-derived SC at day 50 and day 100 of differentiation in comparison with CNS precursors. FIG. 1H shows top 10 (normal typeface) and selected additional (bold typeface), significantly upregulated genes in day 25 SCP and day 100 SCs. FIG. 1I shows quantification of markers in FIG. 1E. Scale bars=100 μm in FIG. 1B left and middle panel and 25 μm in FIG. 1B right panel and FIG. 1E.

FIG. 2A shows schematic illustration of the hESC-SC co-cultures with hESC-derived sensory or motor neurons. FIG. 2B shows physical association of hESC-SCs with hESC-sensory neurons. FIG. 2C shows transmission electron microscopy shows evidence of in vitro myelination in long term co-cultures of hESC-SCs with hESC-sensory neurons (80 weeks of SC differentiation plus 4 months of co-culture). FIG. 2D shows physical association of hESC-SCs with hESC-motor neurons. FIG. 2E shows calcium imaging quantification of hESC-SC and hESC-motor neuron co-cultures at day 40 and 70 post co-culture. Scale bars=100 μm in FIG. 2B left panel, 20 μm in FIG. 2B right panel, and 0.2 μm in FIG. 2C.

FIG. 3A shows schematic illustration of hESC-SC transplantation in adult rat sciatic nerves. RFP+hPSC-derived Schwann cells were injected following nerve crush at the site of injury (adult Cylcosporin-A treated SD rats). FIG. 3B shows immunofluorescence staining of grafted sciatic nerves for human specific nuclear marker SC101 at 8 weeks post transplantation. FIG. 3C shows confocal analysis of teased nerve fibers for RFP (grafted human cells), axonal marker (NFH) and DAPI. FIG. 3D shows confocal analysis of teased nerve fibers for RFP (grafted human cells), myelin marker MAG (top panel) and P0 (bottom panel) and DAPI. FIG. 3E shows confocal analysis of teased nerve fibers for RFP and node markers Kv1.2 (K+channel, arrow heads, upper panel), CASPR (arrow heads, middle panel), Pan-Na+ (sodium channel, arrow heads, lower panel). Scale bars=100 μm in FIG. 3B, 20 μm in FIGS. 3C and 3D, and 10 μm in FIG. 3E.

FIG. 4A shows flow cytometry analysis of SOX10::GFP in hESC-derived NC (day11) and SCP (day25). FIG. 4B shows flow cytometry analysis of GFAP in hESC-derived SCs at different time points during in vitro differentiation.

FIG. 5A shows schematic illustration of the antibody screening paradigm. FIG. 5B shows primary screening identifies novel surface markers for hESC-SCs. FIG. 5C shows ommunocytochemistry and flow cytometry-based validation of surface marker expression at different stages of SC differentiation.

DETAILED DESCRIPTION OF THE INVENTION

Figure 1A:
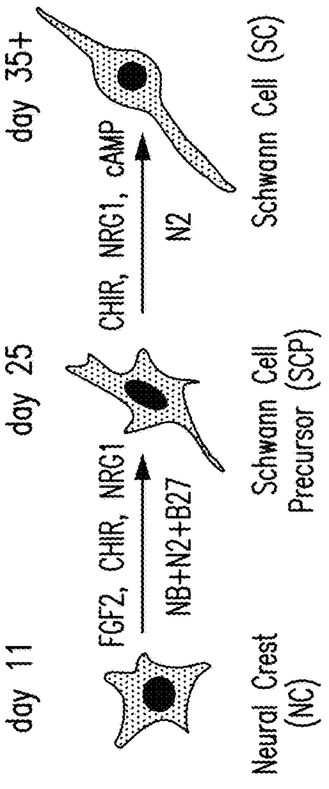
FIGS. 1A-1I: Deriving SCs from hESCs.

The presently disclosed subject matter relates to in vitro methods for inducing differentiation of stem cells (e.g., human stem cells) to cells that express one or more Schwann cell precursor marker (i.e., Schwann cell precursors "SC precursors"), which can further induced in vitro to Schwann cells ("SC"), cells (SC precursors and SCs) produced by such methods and compositions comprising such cells. Also provided are uses of such cells for regeneration of PNS and/or CNS, preventing and/or treating myelin damages and/or for preventing and/or treating a Schwann cell related disorder, e.g., peripheral neuropathy (e.g., Diabetic Peripheral Neuropathy), and for screening compounds suitable for regeneration of PNS and/or CNS, preventing and/or treating myelin damages and/or for preventing and/or treating a Schwann cell related disorder, e.g., peripheral neuropathy (e.g., Diabetic Peripheral Neuropathy).

For purposes of clarity of disclosure and not by way of limitation, the detailed description is divided into the following subsections:

1. Definitions
2. Method of Differentiating Stem Cells
3 Compositions Comprising Schwann Cell Precursors and Schwann Cells
4. Method of Treatments
5. Kits

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "signaling" in reference to a "signal transduction protein" refers to a protein that is activated or otherwise affected by ligand binding to a membrane receptor protein or some other stimulus. Examples of signal transduction protein include, but are not limited to, a Fibroblast Growth Factor (FGF), a SMAD, a wingless (Wnt) complex protein, including beta-catnin, NOTCH, transforming growth factor beta (TGFβ), Activin, Nodal and glycogen synthase kinase 3β (GSK3P) proteins. For many cell surface receptors or internal receptor proteins, ligand-receptor interactions are not directly linked to the cell's response. The ligand activated receptor can first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "signals" refer to internal and external factors that control changes in cell structure and function. They can be chemical or physical in nature.

As used herein, the term "ligands" refers to molecules and proteins that bind to receptors, e.g., TFGβ, Activin, Nodal, bone morphogenic proteins (BMPs), etc.

"Inhibitor" as used herein, refers to a compound or molecule (e.g., small molecule, peptide, peptidomimetic, natural compound, siRNA, anti-sense nucleic acid, aptamer, or antibody) that interferes with (e.g., reduces, decreases, suppresses, eliminates, or blocks) the signaling function of the molecule or pathway. An inhibitor can be any compound or molecule that changes any activity of a named protein (signaling molecule, any molecule involved with the named signaling molecule, a named associated molecule, such as a glycogen synthase kinase 3β (GSK3β) (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate SMAD biological activity by intercepting upstream signaling molecules (e.g., within the extracellular domain, examples of a signaling molecule and an effect include: Noggin which sequesters bone morphogenic proteins, inhibiting activation of ALK receptors 1,2,3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFb signaling molecules. Antibodies that block activins, nodal, TGFb, and BMPs are contemplated for use to neutralize extracellular activators of SMAD signaling, and the like. Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. An inhibitor can be a "direct inhibitor" that inhibits a signaling target or a signaling target pathway by actually contacting the signaling target.

As used herein, the term "schwann cell precursor" refers to a cell that express one or more schwann cell precursor marker, which includes, but not limited to, the schwann cell precursor markers disclosed herein. Under suitable maturation conditions, schwann cell precursors can become schwann cells.

As used herein, the term "schwann cell" refers to a cell that express one or more schwann cell marker, which includes, but not limited to, the schwann cell markers disclosed herein. The Schwann cell can be a myelinating Schwann cell or a non-myelinating Schwann cell. In certain embodiments, the Schwann cells are capable of maintaining and regenerating axons of the neurons in the peripheral nervous system (e.g., maintenance of healthy axons). In certain embodiments, the Schwann cells are capable of forming the myelin sheath. In certain embodiments, the Schwann cells are capable of forming Remak bundles.

"Activators", as used herein, refer to compounds that increase, induce, stimulate, activate, facilitate, or enhance activation the signaling function of the molecule or pathway, e.g., Wnt signaling, or FGF signaling.

As used herein, the term "derivative" refers to a chemical compound with a similar core structure.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells. The population may be a pure population comprising one cell type, such as a population of SC precursors, a population of SCs, or a population of undifferentiated stem cells. Alternatively, the population may comprise more than one cell type, for example a mixed cell population, e.g., a mixed population of SC precursors and SCs.

As used herein, the term "stem cell" refers to a cell with the ability to divide for indefinite periods in culture and to give rise to specialized cells. A human stem cell refers to a stem cell that is from a human.

As used herein, the term "embryonic stem cell" refers to a primitive (undifferentiated) cell that is derived from pre-implantation-stage embryo, capable of dividing without differentiating for a prolonged period in culture, and are known to develop into cells and tissues of the three primary germ layers. A human embryonic stem cell refers to an embryonic stem cell that is from a human. As used herein, the term "human embryonic stem cell" or "hESC" refers to a type of pluripotent stem cells ("PSCs") derived from early stage human embryos, up to and including the blastocyst stage, that is capable of dividing without differentiating for a prolonged period in culture, and are known to develop into cells and tissues of the three primary germ layers.

As used herein, the term "embryonic stem cell line" refers to a population of embryonic stem cells which have been cultured under in vitro conditions that allow proliferation without differentiation for up to days, months to years.

As used herein, the term "totipotent" refers to an ability to give rise to all the cell types of the body plus all of the cell types that make up the extraembryonic tissues such as the placenta.

As used herein, the term "multipotent" refers to an ability to develop into more than one cell type of the body.

As used herein, the term "pluripotent" refers to an ability to develop into the three developmental germ layers of the organism including endoderm, mesoderm, and ectoderm.

As used herein, the term "induced pluripotent stem cell" or "iPSC" refers to a type of pluripotent stem cell, similar to an embryonic stem cell, formed by the introduction of certain embryonic genes (such as a OCT4, SOX2, and KLF4 transgenes) (see, for example, Takahashi and Yamanaka Cell 126, 663-676 (2006), herein incorporated by reference) into a somatic cell, for examples, CI 4, C72, and the like.

As used herein, the term "somatic cell" refers to any cell in the body other than gametes (egg or sperm); sometimes referred to as "adult" cells.

As used herein, the term "somatic (adult) stem cell" refers to a relatively rare undifferentiated cell found in many organs and differentiated tissues with a limited capacity for both self-renewal (in the laboratory) and differentiation. Such cells vary in their differentiation capacity, but it is usually limited to cell types in the organ of origin.

As used herein, the term "neuron" refers to a nerve cell, the principal functional units of the nervous system. A neuron consists of a cell body and its processesan axon and one or more dendrites. Neurons transmit information to other neurons or cells by releasing neurotransmitters at synapses.

As used herein, the term "proliferation" refers to an increase in cell number.

As used herein, the term "undifferentiated" refers to a cell that has not yet developed into a specialized cell type.

As used herein, the term "differentiation" refers to a process whereby an unspecialized embryonic cell acquires the features of a specialized cell such as a heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type, such as SC precursors.

As used herein, the term "directed differentiation" in reference to a stem cell refers to the use of small molecules, growth factor proteins, and other growth conditions to promote the transition of a stem cell from the pluripotent state into a more mature or specialized cell fate (e.g. SC precursors, SCs, etc.).

As used herein, the term "inducing differentiation" in reference to a cell refers to changing the default cell type (genotype and/or phenotype) to a non-default cell type (genotype and/or phenotype). Thus, "inducing differentiation in a stem cell" refers to inducing the stem cell (e.g., human stem cell) to divide into progeny cells with characteristics that are different from the stem cell, such as genotype (e.g., change in gene expression as determined by genetic analysis such as a microarray) and/or phenotype (e.g., change in expression of a protein, such as SC precursor marker(s) and SC marker(s)).

As used herein, the term "cell culture" refers to a growth of cells in vitro in an artificial medium for research or medical treatment.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, the term "contacting" cells with a compound (e.g., one or more inhibitor, activator, and/or inducer) refers to placing the compound in a location that will allow it to touch the cell. The contacting may be accomplished using any suitable methods. For example, contacting can be accomplished by adding the compound to a tube of cells. Contacting may also be accomplished by adding the compound to a culture medium comprising the cells. Each of the compounds (e.g., the inhibitors, activators, and inducers disclosed herein) can be added to a culture medium comprising the cells as a solution (e.g., a concentrated solution). Alternatively or additionally, the compounds (e.g., the inhibitors, activators, and inducers disclosed herein) as well as the cells can be present in a formulated cell culture medium.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "expressing" in relation to a gene or protein refers to making an mRNA or protein which can be observed using assays such as microarray assays, antibody staining assays, and the like.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type.

As used herein, the term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vitro, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

2. Method of Differentiating Stem Cells

The presently disclosed subject matter provides for in vitro methods for inducing differentiation of stem cells (e.g., human stem cells).). In certain embodiments, the stem cell is a human stem cell. Non-limiting examples of human stem cells include human embryonic stem cells (hESC), human pluripotent stem cell (hPSC), human induced pluripotent stem cells (hiPSC), human parthenogenetic stem cells, primordial germ cell-like pluripotent stem cells, epiblast stem cells, F-class pluripotent stem cells, somatic stem cells, cancer stem cells, or any other cell capable of lineage specific differentiation. In certain embodiments, the human stem cell is a human pluripotent stem cell. In certain embodiments, the human stem cell is a human embryonic stem cell (hESC). In certain embodiments, the human stem cell is a human induced pluripotent stem cell (hiPSC). In certain embodiments, the stem cells are non-human stem cells, including, but not limited to, mammalian stem cells, primate stem cells, or stem cells from a rodent, a mouse, a rat, a dog, a cat, a horse, a pig, a cow, a sheep, etc.

The inventors previously disclosed the use of dual SMAD inhibition for inducing differentiation of stem cells (e.g., hPSC) to one type of neural lineage (Chambers (2009), which is incorporated by reference in its entirety). Furthermore, the inventors previously disclosed differentiation of stem cells to neural crest lineage cells (e.g., nociceptors) by sequential inhibition of SMAD signaling followed by activation of Wnt signaling. (Chambers (2012); Mica (2013); WO2011/149762; Fattahi (2016); and U.S. Patent Provisional application No. 62/387,468 filed Dec. 23, 2015, all of which are incorporated by reference in their entireties).

The presently disclosed subject matter is directed to stem-cell-derived Schwann cells. In certain embodiments, the differentiation of stem cells to SCs include three phases: in vitro differentiation of stem cells to cells expressing one or more neural crest lineage marker (neural crest lineage cells), in vitro differentiation of neural crest lineage cells to SC precursors, and in vitro differentiation or maturation of SC precursors to SCs. Any suitable methods for in vitro differentiation of stem cells to neural crest lineage cells, including, but not limited to, those disclosed in Chambers (2012); Mica (2013); WO2011/149762; U.S. Patent Provisional application No. 62/387,468 filed Dec. 23, 2015; and Fattahi (2016) can be used in the first phase of the presently disclosed method. In certain embodiments, a population of stem cells is in vitro differentiated to a population of neural crest lineage cells, which is in vitro differentiated to a population of SC precursors, which is further induced in vitro to a population of SCs.

Non-limiting examples of neural crest lineage marker include SOX10, p75, HNK1, CD49D, ERBB3, TFAP2, SNAIL and SLUG.

In certain embodiments, the neural crest lineage cells are in vitro differentiated from stem cells by inhibition of SMAD signaling and activation of Wnt signaling. In certain embodiments, the method comprises contacting a population of stem cells (e.g., human stem cells) with one or more inhibitor of transforming growth factor beta (TGFβ/Activin-Nodal signaling and one or more Wnt activator.

In certain embodiments, the SC precursors are in vitro differentiated from neural crest lineage cells by inducing SC differentiation. In certain embodiments, the method comprises contacting a population of neural crest lineage cells (e.g., the neural crest lineage cells derived from stem cells by inhibition of SMAD signaling and activation of Wnt signaling) with one or more Wnt activator and one or more FGF activator. In certain embodiments, the method comprises contacting a population of neural crest lineage cells (e.g., the neural crest lineage cells derived from stem cells by inhibition of SMAD signaling and activation of Wnt signaling) with one or more SC differentiation inducer.

In certain embodiments, the SCs are in vitro differentiated from SC precursors by enhancing SC differentiation. In certain embodiments, the method comprises contacting a population of SC precursors (e.g., the SC precursors cells derived from neural crest lineage cells by inducing SC differentiation) with one or more FGF activator, one or more SC differentiation inducer. In certain embodiments, the method comprises contacting a population of SC precursors (e.g., the SC precursors cells derived from neural crest lineage cells by inducing SC differentiation) with one or more SC differentiation enhancer.

1.1. In Vitro Differentiation of Stem Cells to Neural Crest Linage Cells

In certain embodiments, the method of in vitro inducing differentiation of stem cells to cells expressing one or more neural crest lineage maker comprises contacting a population of stem cells (e.g., human stem cells) with one or more inhibitor of transforming growth factor beta (TGFβ)/Activin-Nodal signaling. In certain embodiments, the inhibitor of TGFβ/Activin-Nodal signaling neutralizes the ligands including TGFβs, bone morphogenetic proteins (BMPs), Nodal, and activins, or blocking their signal pathways through blocking the receptors and downstream effectors. Non-limiting examples of inhibitors of TGFβ/Activin-Nodal signaling are disclosed in WO2011/149762, Chambers (2009), and Chambers (2012), which are incorporated by reference in their entireties. In certain embodiments, the one or more inhibitor of TGFβ/Activin-Nodal signaling is a small molecule selected from the group consisting of SB431542, derivatives thereof, and mixtures thereof. In certain embodiments, the one or more inhibitor of TGFβ/Activin-Nodal signaling is SB431542.

"SB431542" refers to a molecule with a number CAS 301836-41-9, a molecular formula of $C_{22}H_{18}N_4O_3$, and a name of 4-[4-(1,3-benzodioxol-5-yl)-5-(2-pyridinyl)-1H-imidazol-2-yl]-benzamide, for example, see structure below:

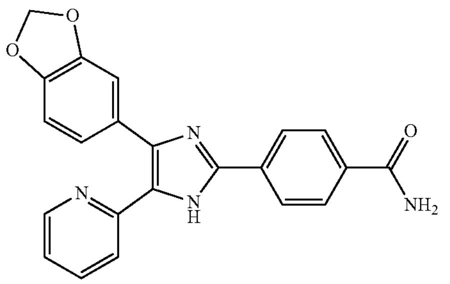 [SMILES: NC(=O)c1ccc(-c2nc(-c3ccc4c(c3)OCO4)c(-c3ccccn3)[nH]2)cc1]

In certain embodiments, the method of in vitro inducing differentiation of stem cells to cells expressing one or more neural crest lineage maker further comprises contacting the stem cells with one or more inhibitor of Small Mothers Against Decapentaplegic (SMAD) signaling ("SMAD inhibitor"). Non-limiting examples of SMAD inhibitors are disclosed in WO2011/149762, Chambers (2009), and Chambers (2012), which are incorporated by reference in their entireties. In certain embodiments, the one or more inhibitor of SMAD signaling is a small molecule selected from the group consisting of LDN193189, derivatives thereof, and mixtures thereof. In certain embodiments, the one or more SMAD inhibitor is LDN193189.

"LDN193189" refers to a small molecule DM-3189, IUPAC name 4-(6-(4-(piperazin-1-yl)phenyl)pyrazolo[1,5-a]pyrimidin-3-yl)quinoline, with a chemical formula of $C_{25}H_{22}N_6$ with the following formula.

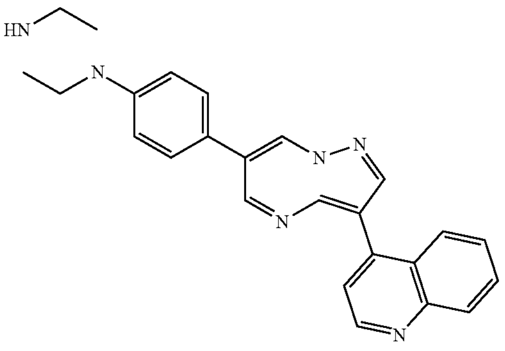

LDN193189 is capable of functioning as a SMAD signaling inhibitor. LDN193189 is also highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8 (Yu et al. (2008) Nat Med 14:1363-1369; Cuny et al. (2008) Bioorg. Med. Chem. Lett. 18: 4388-4392, herein incorporated by reference).

In certain embodiments, the method of in vitro inducing differentiation of stem cells to cells expressing one or more neural crest lineage maker comprises further comprises contacting the cells with one or more Wnt activator. As used herein, the term "WNT" or "wingless" in reference to a ligand refers to a group of secreted proteins (i.e. Intl (integration 1) in humans) capable of interacting with a WNT receptor, such as a receptor in the Frizzled and LRPDerailed/RYK receptor family. As used herein, the term "WNT" or "wingless" in reference to a signaling pathway refers to a signal pathway composed of Wnt family ligands and Wnt family receptors, such as Frizzled and LRPDerailed/RYK receptors, mediated with or without β-catenin. In certain embodiments, a WNT signaling pathway includes mediation by β-catenin, e.g., WNT/-catenin.

In certain embodiments, the one or more Wnt activator lowers glycogen synthase kinase 3β (GSK3β) for activation of Wnt signaling. Thus, the Wnt activator can be a GSK3β inhibitor. A GSK3P inhibitor is capable of activating a WNT signaling pathway, see e.g., Cadigan, et al., J Cell Sci. 2006; 119:395-402; Kikuchi, et al., Cell Signaling. 2007; 19:659-671, which are incorporated by reference herein in their entireties. As used herein, the term "glycogen synthase kinase 3β inhibitor" refers to a compound that inhibits a glycogen synthase kinase 3β enzyme, for example, see, Doble, et al., J Cell Sci. 2003; 116:1175-1186, which is incorporated by reference herein in its entirety.

Non-limiting examples of Wnt activators or GSK3β inhibitors are disclosed in WO2011/149762, Chambers (2012), and Calder et al., J Neurosci. 2015 Aug. 19; 35(33): 11462-81, which are incorporated by reference in their entireties. In certain embodiments, the one or more Wnt activator is a small molecule selected from the group consisting of CHIR99021, WNT3A, Wnt-1, Wnt4, Wnt5a, derivatives thereof, and mixtures thereof. In certain embodiments, the one or more Wnt activator is CHIR99021.

"CHIR99021" (also known as "aminopyrimidine" or "3-[3-(2-Carboxyethyl)-4-methylpyrrol-2-methylidenyl]-2-indolinone") refers to IUPAC name 6-(2-(4-(2,4-dichlorophenyl)-5-(4-methyl-1H-imidazol-2-yl)pyrimidin-2-ylamino)ethylamino)nicotinonitrile with the following formula.

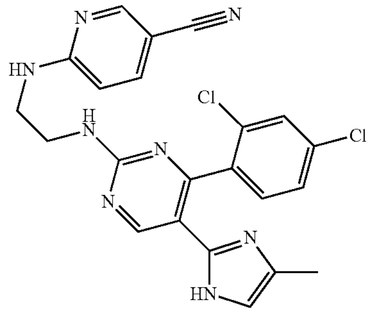 [SMILES: Cc1c[nH]c(-c2cnc(NCCNc3ccc(C#N)cn3)nc2-c2ccc(Cl)cc2Cl)n1]

CHIR99021 is highly selective, showing nearly thousand-fold selectivity against a panel of related and unrelated kinases, with an IC50=6.7 nM against human GSK3β and nanomolar IC50 values against rodent GSK3β homologs.

For in vitro differentiation of stem cells to cells expressing one or more neural crest lineage marker, the stem cells can be contacted with the one or more inhibitor of TGFβ/Activin-Nodal signaling for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days. In certain embodiments, the stem cells are contacted with the one or more inhibitor of TGFβ/Activin-Nodal signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days. In certain embodiments, the stem cells are contacted with the one or more inhibitor of TGFβ/Activin-Nodal signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days. In certain embodiments, the stem cells are contacted with the one or more inhibitor of TGFβ/Activin-Nodal signaling for between 10 days and about 15 days. In certain embodiments, the stem cells are contacted with the one or more inhibitor of TGFβ/Activin-Nodal signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day. In certain embodiments, the stem cells are contacted with the one or more inhibitor of TGFβ/Activin-Nodal signaling for about 10 days. In certain embodiments, the stem cells are contacted with the one or more inhibitor of TGFβ/Activin-Nodal signaling for about 11 days.

For in vitro differentiation of stem cells to cells expressing one or more neural crest lineage marker, the stem cells can be contacted with the one or more inhibitor of SMAD signaling for at least about 3 days, at least about 4 days, at least about 5 days, at least about 6 days, at least about 7 days, at least about 8 days, at least about 9 days, at least about 10 days, at least about 11 days, at least about 12, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days. In certain embodiments, the stem cells are contacted with the one or more inhibitor of SMAD signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, for up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days. In certain embodiments, the stem cells are contacted with the one or more inhibitor of SMAD signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days. In certain embodiments, the stem cells are contacted with the one or more inhibitor of SMAD signaling for between 10 days and about 15 days. In certain embodiments, the stem cells are contacted with the one or more inhibitor of SMAD signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day. In certain embodiments, the stem cells are contacted with the one or more inhibitor of SMAD signaling for about 10 days. In certain embodiments, the stem cells are contacted with the one or more inhibitor of SMAD signaling for about 11 days.

Furthermore, the cells can be contacted with the one or more activator of Wnt signaling for at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, or at least about 29 days, at least about 30 days. In certain embodiments, the cells are contacted with the one or more activator of Wnt signaling for up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days. In certain embodiments, the cells are contacted with the one or more activator of Wnt signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days. In certain embodiments, the cells are contacted with the one or more activator of Wnt signaling for between 5 days and about 15 days. In certain embodiments, the cells are contacted with the one or more activator of Wnt signaling for about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day. In certain embodiments, the cells are contacted with the one or more activator of Wnt signaling for about 11 days. In certain embodiments, the cells are contacted with the one or more activator of Wnt signaling for about 10 days. In certain embodiments, the cells are contacted with the one or more activator of Wnt signaling for about 9 days.

In certain embodiments, the stem cells are contacted with the one or more inhibitor of TGFβ/Activin-Nodal signaling in a concentration of from about 1 nM to about 300 nM, from about 5 nM to about 250 nM, from about 10 nM to about 200 nM, from about 10 nM to about 50 nM, from about 50 nM to about 150 nM, from about 80 nM to about 120 nM, from about 90 nM to about 110 nM, from about 50 nM to about 100 nM, from about 100 nM to about 150 nM, from about 150 nM to about 200 nM, from about 200 nM to about 250 nM, or from about 250 nM to about 300 nM. In certain embodiments, the stem cells are contacted with the one or more inhibitor of TGFβ/Activin-Nodal signaling in a concentration of from about 80 nM to about 120 nM. In certain embodiments, the stem cells are contacted with the one or more inhibitor of TGFβ/Activin-Nodal signaling in a concentration of about 100 nM. In certain embodiments, the stem cells are contacted with the one or more inhibitor of TGFβ/Activin-Nodal signaling in any one of the above-described concentrations daily, every other day or every two days. In certain embodiments, the stem cells are contacted with the one or more inhibitor of TGFβ/Activin-Nodal signaling in a concentration of about 100 nM daily.

In certain embodiments, the stem cells are contacted with the one or more inhibitor of SMAD signaling in a concentration of from about 1 μM to 100 μM, from about 1 μM to 20 μM, from about 1 μM to 15 μM, from about 1 μM to 10 μM, from about 1 μM to 5 μM, from about 5 μM to 10 μM, from about 5 μM to 15 μM, from about 15 μM to 20 μM, from about 20 μM to 30 μM, from about 30 μM to 40 μM, from about 40 μM to 50 μM, from about 50 μM to 60 μM, from about 60 μM to 70 μM, from about 70 μM to 80 μM, from about 80 μM to 90 μM, or from about 90 μM to 100 μM. In certain embodiments, the stem cells are contacted with the one or more inhibitor of SMAD signaling in a concentration of from about from about 5 μM to 15 μM. In certain embodiments, the stem cells are contacted with the one or more inhibitor of SMAD signaling in a concentration of about 10 μM. In certain embodiments, the stem cells are contacted with the one or more inhibitor of SMAD signaling in any one of the above-described concentrations daily, every other day or every two days. In certain embodiments, the stem cells are contacted with the one or more inhibitor of SMAD signaling in a concentration of about 10 μM daily.

In certain embodiments, the cells are contacted with the one or more activator of Wnt signaling in a concentration of from about 1 μM to 100 μM, from about 1 μM to 20 μM, from about 1 μM to 15 from about 1 μM to 10 from about 1 μM to 5 from about 5 μM to 10 from about 5 μM to 15 μM, from about 15 μM to 20 μM from about 20 μM to 30 μM, from about 30 μM to 40 μM, from about 40 μM to 50 μM, from about 50 μM to 60 μM, from about 60 μM to 70 μM, from about 70 μM to 80 μM, from about 80 μM to 90 μM, or from about 90 μM to 100 μM. In certain embodiments, the cells are contacted with the one or more activator of Wnt signaling in a concentration of from about 1 μM to 5 μM. In certain embodiments, the ells are contacted with the one or more activator of Wnt signaling in a concentration of about 3 μM. In certain embodiments, the cells are contacted with the one or more activator of Wnt signaling in any one of the above-described concentrations daily, every other day or every two days. In certain embodiments, the cells are contacted with the one or more activator of Wnt signaling in a concentration of about 3 μM daily.

1.2. In Vitro Differentiation of Neural Crest Lineage Cells to Schwann Cell Precursors A presently disclosed differentiation method for direct differentiation of Neural Crest Lineage Cells to Schwann Cell Precursors comprises contacting the cells (e.g., cells expressing one or more neural crest lineage marker, e.g., differentiated cells after contacting a population of stem cells with one or more TGFβ/Activin-Nodal signaling and optionally one or more SMAD inhibitor, and further contacting the cells with one or more Wnt activator,) with one or more Wnt activator described herein, and one or more activator of FGF signaling ("FGF activator") to produce a population of SC precursors, e.g., cells that express one or more Schwann cell precursor marker. In certain embodiments, the method comprises contacting the cells (e.g., cells expressing one or more neural crest lineage marker, e.g., differentiated cells after contacting a population of stem cells with one or more TGFβ/Activin-Nodal signaling and optionally one or more SMAD inhibitor, and further contacting the cells with one or more Wnt activator) with one or more molecule that induces Schwann cell differentiation ("SC differentiation inducer") to produce a population of SC precursors, e.g., cells that express one or more Schwann cell precursor marker.

Non-limiting examples of SC differentiation inducers include neuregulins, LIF, CNTF, Forskolin, TGFβ and FBS. In certain embodiments, the one or more SC differentiation inducer is Neuregulin 1 (NRG1).

Non-limiting examples of activators of FGF signaling include FGF1, FGF2, FGF3, FGF4, FGF7, FGF8, FGF10, FGF18, derivatives, and mixtures thereof. In certain embodiments, the one or more FGF activator is FGF2.

In certain embodiments, the cells (e.g., cells expressing one or more neural crest lineage marker) are contacted with the one or more Wnt activator and one or more FGF activator, and optionally one or more SC differentiation inducer concurrently. In certain embodiments, the cells (e.g., cells expressing one or more neural crest lineage marker) are contacted with the one or more Wnt activator, one or more FGF activator, and one or more SC differentiation inducer concurrently. For example, the one or more Wnt activator and one or more FGF activator, and optionally one or more SC differentiation inducer are all present in a cell culture medium comprising the cells (e.g., cells expressing one or more neural crest lineage marker). In certain embodiments, the one or more Wnt activator, one or more FGF activator, and optionally one or more SC differentiation inducer are added together daily (or every other day or every two days) to a cell culture medium comprising the cells (e.g., cells expressing one or more neural crest lineage marker, e.g., differentiated cells after contacting a population of stem cells with one or more TGFβ/Activin-Nodal signaling and optionally one or more SMAD inhibitor, and further contacting the cells with one or more Wnt activator).

The cells expressing one or more neural crest lineage marker can be contacted with the one or more Wnt activator, one or more FGF activator, and optionally one or more SC differentiation inducer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days, to produce SC precursors. In certain embodiments, the cells expressing one or more neural crest lineage marker are contacted with the one or more Wnt activator, one or more FGF activator, and optionally one or more SC differentiation inducer for at least about 10 days to produce SC precursors. In certain embodiments, the cells expressing one or more neural crest lineage marker are contacted with the one or more Wnt activator, one or more FGF activator, and optionally one or more SC differentiation inducer for up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce SC precursors. In certain embodiments, the cells expressing one or more neural crest lineage marker are contacted with the one or more Wnt activator, one or more FGF activator, and optionally one or more SC differentiation inducer for between about 3 days and about 5 days, between about 5 days and about 10 days, between about 10 days and about 15 days, between about 15 days and about 20 days, between about 20 days and about 25 days, or between about 25 days and about 30 days, to produce SC precursors. In certain embodiments, the cells expressing one or more neural crest lineage marker are contacted with the one or more Wnt activator, one or more FGF activator, and optionally one or more SC differentiation inducer for between about 10 days and about 15 days to produce SC precursors. In certain embodiments, the cells expressing one or more neural crest lineage marker are contacted with the one or more Wnt activator, one or more FGF activator, and optionally one or more SC differentiation inducer for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days, to produce SC precursors. In certain embodiments, the cells expressing one or more neural crest lineage marker are contacted with the one or more Wnt activator, one or more FGF activator, and optionally one or more SC differentiation inducer for about 14 days to produce SC precursors. In certain embodiments, the cells expressing one or more neural crest lineage marker are contacted with the one or more Wnt activator, one or more FGF activator, and optionally one or more SC differentiation inducer for about 15 days to produce SC precursors.

In certain embodiments, the cells are contacted with one or more Wnt activator to produce a population of cells expressing one or more neural crest lineage marker, and the neural crest linage cell population is further contacted with the one or more Wnt activator. Thus, the cells can be contacted with the one or more Wnt activator for at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, or at least about 29 days, at least about 30 days, at least about 31 days, at least about 32 days, at least about 33 days, at least about 34 days, at least about 35 days, at least about 36 days, at least about 37 days, at least about 38 days, at least about 39 days, or at least about 40 days, in total. In certain embodiments, the cells are contacted with the one or more Wnt activator for up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, up to about 30 days, up to about 31 days, up to about 32 days, up to about 33 days, up tot about 34 days, up to about 35 days, up to about 36 days, up to about 37 days, up to about 38 days, up to about 39 days, up to about 40 days, up to about 41 days, up to about 42 days, up to about 43 days, up to about 44 days, up to about 45 days, up to about 46 days, up to about 47 days, up to about 48 days, up to about 49 days, up to about 50 days, up to about 51 days, up to about 52 days, up to about 53 days, up to about 54 days, up to about 55 days, up to about 56 days, up to about 57 days, up to about 58 days, up to about 59 days, or up to about 60 days in total. In certain embodiments, the cells are contacted with the one or more Wnt activator for between about 14 days and about 20 days, between about 20 days and about 25 days, between about 25 days and about 30 days, between about 30 days and about 35 days, between about 35 days and about 40 days, between about 40 days and about 45 days, between about 45 days and about 50 days, between about 50 days and about 55 days, or between about 55 days and about 60 days. In certain embodiments, the cells are contacted with the one or more Wnt activator for between 20 days and about 30 days, in total. In certain embodiments, the cells are contacted with the one or more activator of Wnt signaling for between 20 days and about 25 days, in total. In certain embodiments, the cells are contacted with the one or more Wnt activator for between 25 days and about 30 days, in total. In certain embodiments, the cells are contacted with the one or more activator of Wnt signaling for about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days or about 60 days, in total. In certain embodiments, the cells are contacted with the one or more Wnt activator for about 26 days in total. In certain embodiments, the cells are contacted with the one or more activator of Wnt signaling for about 25 days in total. In certain embodiments, the cells are contacted with the one or more Wnt activator for about 24 days in total. In certain embodiments, the cells are contacted with the one or more Wnt activator for about 23 days in total.

In certain embodiments, the cells (e.g., cells expressing one or more neural crest lineage marker) are contacted with the one or more activator of FGF signaling in a concentration of from about 1 nM to 100 nM, from about 1 nM to 20 nM, from about 1 nM to 15 nM, from about 1 nM to 10 nM, from about 1 nM to 5 nM, from about 5 nM to 10 nM, from about 5 nM to 15 nM, from about 15 nM to 20 nM, from about 20 nM to 30 nM, from about 30 nM to 40 nM, from about 40 nM to 50 nM, from about 50 nM to 60 nM, from about 60 nM to 70 nM, from about 70 nM to 80 nM, from about 80 nM to 90 nM, or from about 90 nM to 100 nM, to produce SC precursors. In certain embodiments, the cells (e.g., cells expressing one or more neural crest lineage marker) are contacted with the one or more activator of FGF signaling in a concentration of from about from about 5 nM to 15 nM to produce SC precursors. In certain embodiments, the cells (e.g., cells expressing one or more neural crest lineage marker) are contacted with the one or more activator of FGF signaling in a concentration of about 10 nM to produce SC precursors. In certain embodiments, the cells (e.g., cells expressing one or more neural crest lineage marker) are contacted with the one or more activator of FGF signaling in any one of the above-described concentrations daily, every other day or every two days to produce SC precursors. In certain embodiments, the cells (e.g., cells expressing one or more neural crest lineage marker) are contacted with the one or more activator of FGF signaling in a concentration of about 10 nM daily to produce SC precursors.

In certain embodiments, the cells (e.g., cells expressing one or more neural crest lineage marker) are contacted with the one or more molecule that induces Schwann cell differentiation in a concentration of from about 1 ng/ml to 100 ng/ml, from about 1 ng/ml to 20 ng/ml, from about 1 ng/ml to 15 ng/ml, from about 1 ng/ml to 10 ng/ml, from about 1 ng/ml to 5 ng/ml, from about 5 ng/ml to 10 ng/ml, from about 5 ng/ml to 15 ng/ml, from about 15 ng/ml to 25 ng/ml, from about 15 ng/ml to 20 ng/ml, from about 20 ng/ml to 30 ng/ml, from about 30 ng/ml to 40 ng/ml, from about 40 ng/ml to 50 ng/ml, from about 50 ng/ml to 60 ng/ml, from about 60 ng/ml to 70 ng/ml, from about 70 ng/ml to 80 ng/ml, from about 80 ng/ml to 90 ng/ml, or from about 90 ng/ml to 100 ng/ml to produce SC precursors. In certain embodiments, the cells (e.g., cells expressing one or more neural crest lineage marker) are contacted with the one or more molecule that induces Schwann cell differentiation in a concentration of from about from about 5 ng/ml to 15 ng/ml to produce SC precursors. In certain embodiments, the cells (e.g., cells expressing one or more neural crest lineage marker) are contacted with the one or more molecule that induces Schwann cell differentiation in a concentration of about 10 ng/ml to produce SC precursors. In certain embodiments, the cells (e.g., cells expressing one or more neural crest lineage marker) are contacted with the one or more molecule that induces Schwann cell differentiation in any one of the above-described concentrations daily, every other day or every two days to produce SC precursors. In certain embodiments, the cells (e.g., cells expressing one or more neural crest lineage marker) are contacted with the one or more molecule that induces Schwann cell differentiation in a concentration of about 10 ng/ml daily to produce SC precursors. In certain embodiments, the cells (e.g., cells expressing one or more neural crest lineage marker) are contacted with the one or more molecule that induces Schwann cell differentiation in a concentration of about 10 ng/ml daily to produce SC precursors.

In certain embodiments, the cells (e.g., cells expressing one or more neural crest lineage marker) are contacted with the one or more activator of Wnt signaling in a concentration of from about 1 μM to 100 μM, from about 1 μM to 20 μM, from about 1 μM to 15 μM, from about 1 μM to 10 μM, from about 1 μM to 5 μM, from about 5 μM to 10 μM, from about 5 μM to 15 μM, from about 15 μM to 20 μM, from about 20 μM to 30 μM, from about 30 μM to 40 μM, from about 40 μM to 50 μM, from about 50 μM to 60 μM, from about 60 M to 70 μM, from about 70 μM to 80 μM, from about 80 μM to 90 μM, or from about 90 μM to 100 μM, to produce SC precursors. In certain embodiments, the cells (e.g., cells expressing one or more neural crest lineage marker) are contacted with the one or more activator of Wnt signaling in a concentration of from about 1 μM to 5 μM to produce SC precursors. In certain embodiments, the cells (e.g., cells expressing one or more neural crest lineage marker) are contacted with the one or more activator of Wnt signaling in a concentration of about 3 μM to produce SC precursors. In certain embodiments, the cells (e.g., cells expressing one or more neural crest lineage marker) are contacted with the one or more activator of Wnt signaling in any one of the above-described concentrations daily, every other day or every two days. In certain embodiments, the cells (e.g., cells expressing one or more neural crest lineage marker) are contacted with the one or more activator of Wnt signaling in a concentration of about 3 μM daily.

In certain embodiments, a cell population comprising at least about 50% cells expressing one or more neural crest lineage marker are differentiated into cells expressing one or more Schwann cell precursor marker, wherein the population of cells are contacted with one Wnt activator (e.g., CHIR99021, e.g., 3 μM CHIR99021), one FGF activator (e.g., FGF2, e.g., 10 nM FGF2), and one SC differentiation inducer (e.g., NRG1, e.g., 10 ng/ml NRG1) for about 15 days (e.g., about 14 days or about 15 days).

In certain embodiments, the stem cells are differentiated into cells expressing one or more Schwann cell precursor marker, wherein the cells are contacted with one inhibitor of TGFβ/Activin-Nodal signaling (e.g., SB431542, e.g., 10 μM SB431542) and optionally one SMAD inhibitor (e.g., LDN193189, e.g., 100 nM LDN193189) for about 10 days (e.g., about 10 days or 11 about days); with one Wnt activator (e.g., CHIR99021, e.g., 3 μM CHIR99021) for about 23 days (e.g., about 23 days or about 24 days); and with one FGF activator (e.g., FGF2, e.g., 10 nM FGF2) and one SC differentiation inducer (e.g., NRG1, e.g., 10 ng/ml NRG1) for about 15 days (e.g., about 14 or 15 days).

In certain embodiments, the cells are not exposed to an activator of Sonic Hedgehog (SHH) signaling. Non-limiting examples of activators of SHH signaling include sonic hedgehog (SHH), C25II, smoothened (SMO) receptor small molecule agonists (e.g., purmorphamine), derivatives thereof, and mixtures thereof. In certain embodiments, the cells are not exposed to SHH.

1.3. In Vitro Induction of Schwann Cell Precursors to Schwann Cells

The Schwann cell precursors can be further induced in vitro to Schwann cells. The differentiated SC precursors can be subjected to conditions favoring maturation of SC precursors into a population of Schwann cells. The Schwann cell can be a myelinating Schwann cell or a non-myelinating Schwann cell.

In certain embodiments, the Schwann cell precursors (SC precursors) are contacted with one or more FGF activator described herein, one or more Schwann cell differentiation inducer described herein to produce a population of SCs. In certain embodiments, the Schwann cell precursors (SC precursors) are contacted with one or more molecule that enhances Schwann cell differentiation (referred to as "SC differentiation enhancer"). Non-limiting examples of SC differentiation enhancers include neuregulins, cyclic adenosine monophosphate (cAMP), Forskolin, LIF, and CNTF. In certain embodiments, the one or more SC differentiation enhancer is selected cAMP. In certain embodiments, the Schwann cell precursors (SC precursors) are contacted with one FGF activator and two Schwann cell differentiation inducers to produce a population of SCs. In certain embodiments, the two Schwann cell differentiation inducers are cAMP and NRG1.

In certain embodiments, the SC precursors are contacted with the one or more FGF activator and one or more Schwann cell differentiation inducer, and optionally one or more SC differentiation enhancer in a cell culture medium to produce SCs. In certain embodiments, the cell culture medium is an NB medium supplemented with L-Glutamine (e.g., from Gibco, 25030-164), N2 (e.g., from Stem Cell Technologies, 07156), and B27 (e.g., from Life Technologies, 17504044).

In certain embodiments, the SC precursors are contacted with the one or more molecule that induces Schwann cell differentiation in a concentration of from about 1 ng/ml to 100 ng/ml, from about 1 ng/ml to 20 ng/ml, from about 1 ng/ml to 15 ng/ml, from about 1 ng/ml to 10 ng/ml, from about 1 ng/ml to 5 ng/ml, from about 5 ng/ml to 10 ng/ml, from about 5 ng/ml to 15 ng/ml, from about 15 ng/ml to 25 ng/ml, from about 15 ng/ml to 20 ng/ml, from about 20 ng/ml to 30 ng/ml, from about 30 ng/ml to 40 ng/ml, from about 40 ng/ml to 50 ng/ml, from about 50 ng/ml to 60 ng/ml, from about 60 ng/ml to 70 ng/ml, from about 70 ng/ml to 80 ng/ml, from about 80 ng/ml to 90 ng/ml, or from about 90 ng/ml to 100 ng/ml to produce SCs. In certain embodiments, the SC precursors are contacted with the one or more molecule that induces Schwann cell differentiation in a concentration of from about 15 ng/ml to 25 ng/ml to produce SCs. In certain embodiments, the SC precursors are contacted with the one or more molecule that induces Schwann cell differentiation in a concentration of about 20 ng/ml to produce SCs. In certain embodiments, the SC precursors are contacted with the one or more molecule that induces Schwann cell differentiation in any one of the above-described concentrations daily, every other day or every two days to produce SCs. In certain embodiments, the SC precursors are contacted with the one or more molecule that induces Schwann cell differentiation in a concentration of about 10 ng/ml daily to produce SCs.

In certain embodiments, the SC precursors are contacted with the one or more FGF activator, and one or more Schwann cell differentiation inducer, and optionally one or more SC differentiation enhancer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days, to produce SCs. In certain embodiments, the SC precursors are contacted with the one or more FGF activator, and one or more Schwann cell differentiation inducer, and optionally one or more SC differentiation enhancer for between about 3 days and about 40 days, between about 3 days and about 35 days, between about 3 days and about 30 days, between about 3 days and about 25 days, between about 3 days and about 20 days, between about 3 days and about 15 days, between about 10 days and about 40 days, between about 10 days and about 20 days, between about 20 days and about 40 days, between about 20 days and about 30 days, or between about 30 days and about 40 days, to produce SCs. In certain embodiments, the SC precursors are contacted with the one or more FGF activator, and one or more Schwann cell differentiation inducer, and optionally one or more SC differentiation enhancer for between about 3 days and about 15 days to produce SCs. In certain embodiments, the SC precursors are contacted with the one or more FGF activator, and one or more Schwann cell differentiation inducer, and optionally one or more SC differentiation enhancer for between about 30 days and about 40 days to produce SCs. In certain embodiments, the SC precursors are contacted with the one or more FGF activator, and one or more Schwann cell differentiation inducer, and optionally one or more SC differentiation enhancer for about 10 days to produce SCs. In certain embodiments, the SC precursors are contacted with the one or more FGF activator, and one or more Schwann cell differentiation inducer, and optionally one or more SC differentiation enhancer for about 11 days to produce SCs. In certain embodiments, the SC precursors are contacted with the one or more FGF activator, and one or more Schwann cell differentiation inducer, and optionally one or more SC differentiation enhancer for about 35 days to produce SCs.

In certain embodiments, the SC precursors are contacted with the one or more activator of FGF signaling in a concentration of from about 1 nM to 100 nM, from about 1 nM to 20 nM, from about 1 nM to 15 nM, from about 1 nM to 10 nM, from about 1 nM to 5 nM, from about 5 nM to 10 nM, from about 5 nM to 15 nM, from about 15 nM to 20 nM, from about 20 nM to 30 nM, from about 30 nM to 40 nM, from about 40 nM to 50 nM, from about 50 nM to 60 nM, from about 60 nM to 70 nM, from about 70 nM to 80 nM, from about 80 nM to 90 nM, or from about 90 nM to 100 nM, to produce SCs. In certain embodiments, the SC precursors are contacted with the one or more activator of FGF signaling in a concentration of from about from about 5 nM to 15 nM to produce SC precursors. In certain embodiments, the stem cells are contacted with the one or more activator of FGF signaling in a concentration of about 10 nM to produce SCs. In certain embodiments, the SC precursors are contacted with the one or more activator of FGF signaling in any one of the above-described concentrations daily, every other day or every two days to produce SCs. In certain embodiments, the SC precursors are contacted with the one or more activator of FGF signaling in a concentration of about 10 nM daily to produce SCs.

In certain embodiments, conditions favoring maturation from SC precursors to SCs comprise aggregating the differentiated SC precursors cells into 3D spheroids, and further contacting said 3D spheroids with the one or more FGF activator, and the one or more Schwann cell differentiation inducer, and optionally the one or more SC differentiation enhancer. In certain embodiments, the culture medium is the suspension culture medium.

In certain embodiments, a cell population comprising at least about 50% cells expressing one or more Schwann cell precursor marker are differentiated into cells expressing one or more Schwann cell marker, wherein the population of cells are contacted with one FGF activator (e.g., FGF2, e.g., 10 nM FGF2), two SC differentiation inducers (e.g., NRG1 (e.g., 10 ng/ml NRG1) and cAMP (e.g., 100 mM cAMP)) for at least about 10 days.

In certain embodiments, the cells are not exposed to an activator of Sonic Hedgehog (SHH) signaling. Non-limiting examples of activators of SHH signaling include sonic hedgehog (SHH), C25II, smoothened (SMO) receptor small molecule agonists (e.g., purmorphamine), derivatives thereof, and mixtures thereof. In certain embodiments, the cells are not exposed to SHH.

1.4. Cell Culture Media

In certain embodiments, the above-described inhibitors, activators, inducers and enhancers are added to a cell culture medium comprising the cells, e.g., stem cells, cells expressing one or more neural crest lineage marker, cells expressing one or more SC precursor marker, cells expressing one or more SC marker, or a combination thereof. Suitable cell culture media include, but are not limited to, Knockout® Serum Replacement ("KSR") medium, N2 medium, an Essential 8®/Essential 6® ("E8/E6") medium, and a Neurobasal (NB) medium (e.g., a NB medium supplemented with N2 and B-27® Supplement). KSR medium, N2 medium, E8/E6 medium and NB medium are commercially available. In certain embodiments, a medium for in vitro differentiation of stem cells to cells expressing one or more neural crest lineage marker is a medium selected from the group consisting of a KSR medium, a N2 medium, and a combination thereof. In certain embodiments, a medium for in vitro differentiation of stem cells to cells expressing one or more neural crest lineage marker is an E8/E6 medium. In certain embodiments, a medium for in vitro induction of cells expressing one or more neural crest lineage marker to cells expressing one or more SC precursor marker is an NB medium. In certain embodiments, a medium for in vitro induction of cells expressing one or more SC precursor marker to cells expressing one or more SC marker is an NB medium.

KSR medium is a defined, serum-free formulation optimized to grow and maintain undifferentiated hESC cells in culture. The components of a KSR medium are disclosed in WO2011/149762. In certain embodiments, a KSR medium comprises Knockout DMEM, Knockout Serum Replacement, L-Glutamine, Pen/Strep, MEM, and 13-mercaptoethanol. In certain embodiments, 1 liter of KSR medium can comprise 820 mL of Knockout DMEM, 150 mL of Knockout Serum Replacement, 10 mL of 200 mM L-Glutamine, 10 mL of Pen/Strep, 10 mL of 10 mM MEM, and 55 μM of 13-mercaptoethanol.

E8/E6 medium is a feeder-free and xeno-free medium that supports the growth and expansion of human pluripotent stem cells. E8/E6 medium has been proven to support somatic cell reprogramming. In addition, E8/E6 medium can be used as a base for the formulation of custom media for the culture of PSCs. One example E8/E6 medium is described in Chen et al., Nat Methods. 2011 May; 8(5):424-9, which is incorporated by reference in its entirety. One example E8/E6 medium is disclosed in WO15/077648, which is incorporated by reference in its entirety. In certain embodiments, an E8/E6 cell culture medium comprises DMEM/F12, ascorbic acid, selenium, insulin, $NaHCO_3$, transferrin, FGF2 and TGFβ. The E8/E6 medium differs from a KSR medium in that E8/E6 medium does not include an active BMP or Wnt ingredient. Thus, in certain embodiments, when an E8/E6 medium is used to culture the stem cells, one or more SMAD inhibitor (e.g., those inhibiting BMP) is not required to be added to the E8/E6 medium.

N2 supplement is a chemically defined, animal-free, supplement used for expansion of undifferentiated neural stem and progenitor cells in culture. N2 Supplement is intended for use with DMEM/F12 medium. The components of a N2 medium are disclosed in WO2011/149762. In certain embodiments, a N2 medium comprises a DMEM/F12 medium supplemented with glucose, sodium bicarbonate, putrescine, progesterone, sodium selenite, transferrin, and insulin. In certain embodiments, 1 liter of a N2 medium comprises 985 ml dist. $H_2O$ with DMEM/F12 powder, 1.55 g of glucose, 2.00 g of sodium bicarbonate, putrescine (100 uL aliquot of 1.61 g dissolved in 100 mL of distilled water), progesterone (20 uL aliquot of 0.032 g dissolved in 100 mL 100% ethanol), sodium selenite (60 uL aliquot of 0.5 mM solution in distilled water), 100 mg of transferrin, and 25 mg of insulin in 10 mL of 5 mM NaOH.

In certain embodiments, the stem cells are initially cultured in a KSR medium, which is gradually replaced with increasing amount of a N2 medium from about 1, about 2, about 3, about 4, or about 5, about 6, about 7, or about 8 days after the initial contact of the stem cells with the one or more inhibitor of TGFβ/Activin-Nodal signaling until the contact of the stem cells with the SC differentiation inducers and FGF activators. In certain embodiments, the stem cells are initially cultured in a KSR medium, which is gradually replaced with increasing amount of a N2 medium from day 4 to day 10 after the initial contact of the stem cells with the one or more inhibitor of TGFβ/Activin-Nodal signaling.

The cell culture medium used for culturing the presently disclosed population of stem cells not only determines the inhibitor(s), activator(s), inducer(s) and enhancer(s) to be contacted with the cells (e.g., for a KSR medium, one or more inhibitor of TGFβ/Activin-Nodal signaling and one or more SMAD inhibitor are required; and for an E8/E6 medium, only one or more inhibitor of TGFβ/Activin-Nodal signaling is required), but also determines the sequence of adding the inhibitor(s), activator(s), inducer(s) and enhancer (s) to the cell culture medium.

In certain embodiments, the initial contact of the cells with the one or more Wnt activator is no later than about 4 days (e.g., concurrently (on the same day), or between about 1 and about 4 days, e.g., about 1 day, about 2 days, about 3 days, or about 4 days) from the initial contact of the stem cells with the one or more inhibitor of TGFβ/Activin-Nodal signaling.

In certain embodiments, the cell culture medium for in vitro differentiation of stem cells to cell expressing one or more neural crest lineage marker is a KSR medium, and the initial contact of the cells with the one or more Wnt activator is about 2 days from the initial contact of the stem cells with the one or more inhibitor of TGFβ/Activin-Nodal signaling. In certain embodiments, the initial contact of the stem cells with the one or more SMAD inhibitor is on the same day as the initial contact of the stem cells with the one or more inhibitor of TGFβ/Activin-Nodal signaling, e.g., by initially adding the SMAD inhibitor(s) and inhibitor(s) of TGFβ/Activin-Nodal signaling to a cell culture medium comprising the stem cells on the same day.

In certain embodiments, the cell culture medium for in vitro differentiation of stem cells to cell expressing one or more neural crest lineage marker is an E8/E6 medium, and the initial contact of the cells with the one or more Wnt activator is on the same day as the initial contact of the stem cells with the one or more inhibitor of TGFβ/Activin-Nodal signaling, e.g., by initially adding the Wnt activator(s) and inhibitor(s) of TGFβ/Activin-Nodal signaling to a cell culture medium comprising the stem cells on the same day. In certain embodiments, a BMP active agent is added to the E8/E6 medium. In certain embodiments, the BMP active agent is withdrawn from the medium after about 1 day, about 2 days, about 3 days, about 4 days, about 5 days, about 6 days, about 7 days, about 8 days, about 9 days, or about 10 days of culture. In certain embodiments, the BMP active agent is withdrawn from the medium after about 3 days of culturing. In certain embodiments, the BMP active agent is present in the culture medium at a concentration of from between about 0.5 and about 20 ng/mL, or between about 1 and about 15 ng/ml, or between about 2 and about 10 ng/ml, or between about 3 and about 5 ng/ml. In certain embodiments the BMP active agent is present in the culture medium at a concentration of about 5 ng/ml. Non-limiting examples of BMP active agents include BMP1, BMP2, BMP3, BMP4, BMP5, BMP6, BMP7, BMP8a, BMP8b, BMP10, BMP11, BMP15, derivatives thereof, and mixtures thereof.

In certain embodiments, the initial contact of the one or more FGF activator and optionally the one or more SC differentiation inducer with the cells is no later than about 20 days from the initial contact of the stem cells with the one or more inhibitor of TGFβ/Activin-Nodal signaling. In certain embodiments, the initial contact of the one or more FGF activator and optionally the one or more SC differentiation inducer with the cells is at least about 5 days from the initial contact of the stem cells with the one or more inhibitor of TGFβ/Activin-Nodal signaling. In certain embodiments, the initial contact of the one or more FGF activator and optionally the one or more SC differentiation inducer with the cells is between about 5 days and about 20 days (e.g., about 5 days, about 6 days, about 7 days, about 8 days, about 9 days, about 10 days, about 11 days, about 12, days, about 13 days, about 14 days, about 15 days, about 16 days, about 17 days, about 18 days, about 19 days, or about 20 days) from the initial contact of the stem cells with the one or more inhibitor of TGFβ/Activin-Nodal signaling. In certain embodiments, the initial contact of the one or more FGF activator and optionally the one or more SC differentiation inducer with the cells is about 10 days from the initial contact of the stem cells with the one or more inhibitor of TGFβ/Activin-Nodal signaling. In certain embodiments, the initial contact of the one or more FGF activator and optionally the one or more SC differentiation inducer with the cells is about 11 days from the initial contact of the stem cells with the one or more inhibitor of TGFβ/Activin-Nodal signaling.

In certain embodiments, the Wnt activator(s), FGF activator(s) and optionally SC differentiation inducer(s) are added (daily, every other day or every two days) to a NB medium supplemented with L-Glutamine (e.g., from Gibco, 25030-164), N2 (e.g., from Stem Cell Technologies, 07156), and B27 (e.g., from Life Technologies, 17504044), to produce SC precursors.

In certain embodiments, the SC differentiation inducer(s), FGF activator(s) and optionally SC differentiation enhancer(s) are added (daily, every other day or every two days) to a NB medium supplemented with L-Glutamine (e.g., from Gibco, 25030-164), N2 (e.g., from Stem Cell Technologies, 07156), and B27 (e.g., from Life Technologies, 17504044), to produce SC precursors.

In certain embodiments, the inhibitor(s) of TGFβ/Activin-Nodal signaling, SMAD inhibitor(s), Wnt activator(s), SC differentiation inducer(s), FGF activator(s), and optionally SC differentiation enhancer(s) are added daily (or every other day or every two days) to a cell culture medium comprising the stem cells.

In certain embodiments, the initial contact of the stem cells with the one or more inhibitor of TGFβ/Activin-Nodal signaling and the one or more SMAD inhibitor is on day 0, the initial contact of the cells with the one or more Wnt activator is on day 2, the initial contact of the cells with the one or more FGF activator and optionally the one or more SC differentiation inducer is on day 11, and the initial contact of the cells with the one or more SC differentiation inducer and the one or more FGF activator, and optionally the one or more SC differentiation enhancer is on day 25. In certain embodiments, the cell culture medium for day 0 to day 10 is a KSR medium, a N2 medium, or a mixture thereof. In certain embodiments, the cell culture medium for day 0 to day 3 is a KSR medium. In certain embodiments, the cell culture medium for day 4 to day 10 is a combination of a KSR medium and a N2 medium. In certain embodiments, the cell culture medium for day 10 is a N2 medium. In certain embodiments, the cell culture medium for day 11 and after is a NB medium supplemented with L-Glutamine, N2, and B27.

In certain embodiments, the initial contact of the stem cells with the one or more inhibitor of TGFβ/Activin-Nodal signaling and the one or more Wnt activator is on day 0, the initial contact of the cells with the one or more FGF activator and optionally the one or more SC differentiation inducer is on day 11 (or every other day or every two days), and the initial contact of the cells with one or more SC differentiation inducer and the one or more FGF activator, and optionally the one or more SC differentiation enhancer is on day 25. In certain embodiments, the cell culture medium for day 0 to day 10 is an E8/E6 medium, a N2 medium, or a mixture thereof. In certain embodiments, the cell culture medium for day 11 and after is a NB medium supplemented with L-Glutamine, N2, and B27.

In certain embodiments, the cells are contacted with one or more inhibitor of TGFβ/Activin-Nodal signaling and the one or more SMAD inhibitor for about 10 days; with the one or more Wnt activator for about 23 days; and with the one or more FGF activator for about 14 days, and optionally with the one or more SC differentiation inducer for about 14 days, to produce SC precursors. In certain embodiments, the SC precursors are contacted with one or more SC differentiation inducer, one or more FGF activator and optionally one or more SC differentiation enhancer for at least 8 days (e.g., 10 days or 35 days) to produce SCs.

In certain embodiments, the cells are contacted with one or more inhibitor of TGFβ/Activin-Nodal signaling for about 10 days; with the one or more activator of Wnt signaling for about 25 days; and with the one or more activator of FGF signaling for about 14 days, and optionally the one or more SC differentiation inducer for about 14 days, to produce SC precursors. In certain embodiments, the SC precursors are contacted with one or more SC differentiation inducer, one or more FGF activator and optionally one or more SC differentiation enhancer for at least 8 days (e.g., 10 days or 35 days) to produce SCs.

Schwann cell (SC) precursors (e.g., cells that express one or more early Schwann cell marker) can be differentiated from stem cells in less than about 35 days, in less than about 34 days, in less than about 33 days, in less than about 32 days, in less than about 31 days, in less than about 30 days, in less than about 29 days, in less than about 28 days, in less than about 27 days, in less than about 26 days, in less than about 25 days, in less than about 24 days, in less than about 23 days, in less than about 22 days, in less than about 21 days, or in less than about 20 days from initial contact with the inhibitor(s) of TGFβ/Activin-Nodal signaling. In certain embodiments, SC precursors are differentiated from the stem cells on or after about 25 days from the initial contact with the inhibitor(s) of TGFβ/Activin-Nodal signaling.

1.5. Markers and Reporters

The differentiated SC precursors express one or more Schwann cell precursor marker.

Non-limiting examples of Schwann cell precursor markers include SOX10, GAP43, BLBP, myelin protein zero (MPZ), Dhh, P75NTR, CD49D, TFAP2, CDH19, CD44, ERBB3, POU3F1, glial fibrillary acidic protein (GFAP), CALCB, GRP116, TSPYL5, ITPKA, SLC17A6, SYPL2, LOC100128252, ANGPTL7, LOC728978, ZNF502, SLC16A6, LPL, SLC30A2, SLC10A4, and genes listed in Tables 1-4.

The SCs express one or more Schwann cell marker. Non-limiting examples of Schwann cell markers include leucine rich repeat transmembrane neuronal 4 (LRRTM4), cadherin 1 (CDH1), fatty acid binding protein 7 (FABP7), brain derived neurotrophic factor (BDNF), UNCB5, sclerostin domain containing 1 (SOSTDC1), oligodendrocyte transcription factor 1 (OLIG1), plasminogen activator (PLAT), potassium inwardly-rectifying channel subfamily J member 10 (KCNJ10), sonic hedgehog (SHH), netrin 1 (NTN1), glial cell line derived neurotrophic factor (GDNF), erb-b2 receptor tyrosine kinase 3 (ERBB3), growth associated protein 43 (GAP43), SOX10, S100, GFAP, POU3F1, PMP22, myelin basic protein (MBP), aquaporin 4 (AQP4), NGFR, NFATC4, MOG, IFNG, MAL, NTF3, TGFB1, MPZ, CD9, CD49D, CD49E, CD44, CD98, and CD81, TYRP1, ENTHD1, NT5E, HTR2B, NOV, IL8, SLC16A6, CDKN2A, PLP2, S100A6, AQP9, CDH19, and genes listed in Tables 1-4.

The differentiated SC precursors and further matured SCs can further express one or more reporter. Non-limiting examples of reporters include fluorescent proteins (such as green fluorescent protein (GFP), blue fluorescent protein (EBFP, EBFP2, Azurite, mKalamal), cyan fluorescent protein (ECFP, Cerulean, CyPet, mTurquoise2), and yellow fluorescent protein derivatives (YFP, Citrine, Venus, YPet, EYFP)), β-galactosidase (LacZ), chloramphenicol acetyltransferase (cat), neomycin phosphotransferase (neo), enzymes (such as oxidases and peroxidases); and antigenic molecules. As used herein, the terms "reporter gene" or "reporter construct" refer to genetic constructs comprising a nucleic acid encoding a protein that is easily detectable or easily assayable, such as a colored protein, fluorescent protein such as GFP or an enzyme such as beta-galactosidase (lacZ gene).

The differentiated SC precursors and further matured SCs can be purified after differentiation, e.g., in a cell culture medium. As used herein, the terms "purified," "purify," "purification," "isolated," "isolate," and "isolation" refer to the reduction in the amount of at least one contaminant from a sample. For example, a desired cell type is purified by at least about 10%, by at least about 30%, by at least about 50%, by at least about 75%, and by at least about 90%>, with a corresponding reduction in the amount of undesirable cell types. The term "purify" can refer to the removal of certain cells (e.g., undesirable cells) from a sample. The removal or selection of undesirable cells results in an increase in the percent of desired SC precursors or SCs in the sample. In certain embodiments, the SC precursors are purified by sorting a mixed cell population into cells expressing at least one Schwann cell precursor marker. In certain embodiments, the one or more Schwann cell precursor marker is selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4. In certain embodiments, the one or more Schwann cell precursor marker is selected from the genes listed in Tables 1-4. In certain embodiments, the one or more Schwann cell precursor marker is selected from the genes listed in Table 1. In certain embodiments, the one or more Schwann cell precursor marker is selected from the group consisting of CALCB, GRP116, TSPYL5, ITPKA, SLC17A6, SYPL2, LOC100128252, ANGPTL7, LOC728978, and ZNF502.

The presently disclosed subject matter also provides a population of SC precursors and SCs produced by the in vitro methods described herein, and compositions comprising such cells.

3. Compositions Comprising Schwann Cell Precursors and Schwann Cells

The presently disclosed subject matter provides compositions comprising a population of differentiated SC precursors produced by the in vitro differentiation methods described herewith. Furthermore, the presently disclosed subject matter provides compositions comprising a population of SCs matured from the in vitro differentiated SC precursors described herewith.

Furthermore, the presently disclosed subject matter provides compositions comprising a population of in vitro differentiated cells, wherein at least about 50% (e.g., at least about 55%, at least about 60%, at least about 70%, at least about 75%, at least about 80%, at least about 85%, at least about 90%, at least about 95%, or at least about 99%) of the population of cells express one or more SC precursor marker selected from the group consisting of SOX10, GAP43, BLBP, MPZ, Dhh, P75NTR, CD49D, TFAP2, CDH19, CD44, ERBB3, POU3F1, GFAP, CALCB, GRP116, TSPYL5, ITPKA, SLC17A6, SYPL2, LOC100128252, ANGPTL7, LOC728978, ZNF502, SLC16A6, LPL, SLC30A2, and SLC10A4, and wherein less than about 25% (e.g., less than about 20%, less than about 15%, less than about 10%, less than about 5%, less than about 4%, less than about 3%, less than about 2%, less than about 1%, less than about 0.5%, or less than about 0.1%) of the population of cells express one or more marker selected from the group consisting of stem cells markers, CNS markers, neuronal cell markers, and mesenchymal precursor markers. In certain embodiments, the one or more Schwann cell precursor marker is selected from the genes listed in Tables 1-4. In certain embodiments, the one or more Schwann cell precursor marker is selected from the genes listed in Table 1. In certain embodiments, the one or more Schwann cell precursor marker is selected from the group consisting of CALCB, GRP116, TSPYL5, ITPKA, SLC17A6, SYPL2, LOC100128252, ANGPTL7, LOC728978, and ZNF502.

Furthermore, the presently disclosed subject matter provides compositions comprising a population of in vitro differentiated cells, wherein at least about 50% (e.g., at least about 55%, at least about 60%, at least about 70%, at least about 75%, at least about 80%, at least about 85%, at least about 90%, at least about 95%, or at least about 99%) of the population of cells express one or more SC marker selected from the group consisting of LRRTM4, CDH1, FABP7, BDNF, UNCB5, SOSTDC1, OLIG1, PLAT, KCNJ10, SHH, NTN1, GDNF, ERBB3, GAP43, SOX10, S100, GFAP, POU3F1, PMP22, MBP, AQP4, MPZ, NGFR, NFATC4, MOG, IFNG, MAL, NTF3, TGFB1, CD9, CD81, CD44, CD98, CD49E, CD49D, TYRP1, ENTHD1, NT5E, HTR2B, NOV, IL8, SLC16A6, CDKN2A, PLP2, S100A6, AQP9, and CDH19, and wherein less than about 25% (e.g., less than about 20%, less than about 15%, less than about 10%, less than about 5%, less than about 4%, less than about 3%, less than about 2%, less than about 1%, less than about 0.5%, or less than about 0.1%) of cells express one or more marker selected from the group consisting of SC precursor markers, stem cells markers, CNS markers, neuronal cell markers, and mesenchymal precursor markers. In certain embodiments, the one or more SC marker is selected from the genes listed in Tables 1-4. In certain embodiments, the one or more SC marker is selected from the group consisting of TYRP1, CD44, ENTHD1, NT5E, HTR2B, NOV, IL8, SLC16A6, and CDKN2A.

Non-limiting examples of stem cell markers include OCT4, NANOG, SSEA4 and SSEA3. Non-limiting examples of CNS markers include PAX6, NESTIN, and SOX1. Non-limiting examples of neuronal cell markers include TUJ1, MAP2, NFH, BRN3A, ISL1, TH, ASCL1, CHAT, PHOX2B, PHOX2A, TRKA, TRKB, and TRKC. Non-limiting examples of mesenchymal precursor markers are SMA, and CD73.

In certain embodiments, the composition comprises a population of from about $1\times10^4$ to about $1\times10^{10}$ from about $1\times10^4$ to about $1\times10^5$ from about $1\times10^5$ to about $1\times10^9$ from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ the presently disclosed stem-cell-derived SC precursors or matured SCs are administered to a subject. In certain embodiments, from about $1\times10^5$ to about $1\times10^7$ the presently disclosed stem-cell-derived SC precursors or matured SCs.

In certain embodiments, said composition is frozen. In certain embodiments, said composition may further comprise one or more cryoprotectant, for example, but not limited to, dimethylsulfoxide (DMSO), glycerol, polyethylene glycol, sucrose, trehalose, dextrose, or a combination thereof.

In certain non-limiting embodiments, the composition further comprises a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties).

In certain embodiments, the composition is a pharmaceutical composition that comprises a pharmaceutically acceptable carrier. The compositions can be used for regeneration of Peripheral Nervous System (hereafter "PNS") and/or Central Nervous System (hereafter "CNS"), preventing and/or repairing myelin damages, and/or for preventing and/or treating a Schwann cell related disorder, e.g., peripheral neuropathy (e.g., Diabetic Peripheral Neuropathy).

The presently disclosed subject matter also provides a device comprising the differentiated cells or the composition comprising thereof, as disclosed herein. Non-limiting examples of devices include syringes, fine glass tubes, stereotactic needles and cannulas.

4. Method of Treatments

The in vitro differentiated SC precursors and SCs can be used for regeneration of Peripheral Nervous System (hereafter "PNS"). The in vitro differentiated SC precursors and SCs can be also used for regeneration of Central Nervous System (hereafter "CNS"). Furthermore, the in vitro differentiated SC precursors and SCs can be used for preventing and/or treating/repairing myelin damages. The myelin can be PNS myelin, or CNS myelin.

The in vitro differentiated SC precursors and SCs can also be used for preventing and/or treating Schwann cell related disorders. Non-limiting examples of Schwann cell related disorders include peripheral neuropathy, Schwannomatosis, Charcot Marie Tooth Disease, Guillain Barre Syndrome, metachromatic leukodystrophy, neurofibromatosis, and multiple sclerosis (MS). In certain embodiments, the peripheral neuropathy is Diabetic Peripheral Neuropathy (DPN).

Peripheral glia regulate many crucial aspects of the PNS physiology. They provide trophic support for the neurons, myelinate axons and promote nerve repair. There are many subtypes of peripheral glia including satellite cells of the dorsal root ganglia and autonomic ganglia, the perisynaptic Schwann cells of the neuromuscular junction and the myelinating and non-myelinating Schwann cells that ensheathe the axons of the peripheral neurons. It is known that these subtypes arise from the NC during embryonic development, but the mechanisms that regulate their specification and functional maturation are not well understood. Difficulties in obtaining these embryonic lineages from primary sources limits the ability to dissect the molecular and cellular mechanisms that govern the formation of SCs and acquisition of myelinating or non-myelinating fates in humans. The presently disclosed method for deriving these lineages from human pluripotent stem cells can circumvent these limitations and enable rigorous investigations of these developmental processes. Access to an in vitro model of myelination could facilitate molecular studies of the myelination process in a human system.

In addition to addressing these significant basic questions, the hPSC-derived SCs described herein can also be utilized in translational research. SCs are involved in many types of peripheral neuropathies caused by a variety of factors including genetic mutations, cancer chemotherapy and irradiation induced damage, or metabolic issues such as diabetes.

One of the most prevalent genetic disorders that affect SCs is Charcot Marie Tooth type 1A (CMT1A). This disease is caused by a duplication or triplication in PMP22 gene (Lupski, 1998; Pareyson, 1999). PMP22 is part of the compact myelin structure and is involved in establishing the physical connection between the myelin membrane layers. Elevated levels of PMP22 protein due to increased gene dosage in CMT1A leads to destabilization of the SC membrane and myelin fragility (Lupski, 1998). This pathology in SCs leads to symptoms such as muscle weakness and sensory impairments. By generating SCs from CMT1A patient-derived iPSCs or introducing PMP22 mutations in hESC and their subsequent differentiation into myelinating SCs could enable comprehensive studies of this myelination defect in a human model system that provide insights into disease pathogenesis and potential treatment options.

Chemotherapy and irradiation therapy are among the most common causes of the PNS damage in cancer patients (Quasthoff and Hartung) due to their associated damage to the SCs or the peripheral neurons. Given that, SCs play significant roles in mediating the PNS repair, transplantation of SCs could offer a potential therapeutic opportunity for these neuropathies. The regenerative potential of transplanted SCs has been investigated quite extensively in the context of spinal cord injury (Wiliams and Bunge, 2012). Although, SCs are not normally present in the spinal cord, autologous transplantation of ex vivo expanded SCs is reported to be beneficial in spinal cord repair (Guest et al., 2013). However, it is not clear whether the transplanted SCs directly contribute to myelination of the regenerated axons or their effect is primarily mediated through trophic support. A major hurdle in these transplantation paradigms is obtaining the SCs in large scale and limitation in their migration ability after transplantation in the injured area (Kocsis and Waxman, 2007).

Differentiation of SCs from hPSCs can overcome the scale problem and the fetal nature of hPSC-derived lineages is usually associated with enhanced migration capacity (Master et al., 2007). Therefore, hPSC-SCs opens up new possibilities for cell therapy studies to promote regeneration in the PNS and CNS.

The main cause of peripheral neuropathies is diabetes mellitus (Martyn and Hughes, 1997). There is an enormous unmet need for effective interventions to manage the symptoms and prevent the underlying nerve damage in diabetic patients. Despite extensive attempts, all the candidate drugs tested to date have failed in different stages of clinical trials (Grewal et al., 2016). This is largely due to the inadequacy of the model systems in which these drugs were initially identified or validated (Callaghan et al., 2012). A better understanding of the underlying metabolic and cellular mechanism would be necessary for rational design of therapies to prevent the nerve damage in diabetic peripheral neuropathy (DPN).

The presently disclosed subject matter provides methods for regeneration of PNS. The presently disclosed subject matter provides methods for regeneration of CNS. The presently disclosed subject matter provides methods for preventing and/or treating or repairing myelin damages. The presently disclosed subject matter further provides methods for preventing and/or treating a Schwann cell related disorder.

In certain embodiment, the method comprises administering to a subject in need thereof an effective amount of one or more of the followings:

(a) a population of differentiated Schwann cell precursors described herein;
(b) a composition comprising such differentiated Schwann cell precursors;
(c) a population of Schwann cells described herein; and
(d) a composition comprising such Schwann cells.

Furthermore, the presently disclosed subject matter provides for uses of one or more of the followings for regeneration of PNS and/or CNS, for preventing and/or treating or repairing myelin damages, and/or for preventing and/or treating a Schwann cell related disorder:

(a) a population of differentiated Schwann cell precursors described herein;
(b) a composition comprising such differentiated Schwann cell precursors;
(c) a population of Schwann cells described herein; and
(d) a composition comprising such Schwann cells.

In certain embodiment, the myelin is PNS myelin. In certain embodiment, the myelin is CNS myelin.

In certain embodiment, the Schwann cell related disorder is selected from peripheral neuropathy, Schwannomatosis, Charcot Marie Tooth Disease, Guillain Barre Syndrome, metachromatic leukodystrophy, neurofibromatosis, and multiple sclerosis (MS). In certain embodiments, the peripheral neuropathy is Diabetic Peripheral Neuropathy (DPN).

The presently disclosed stem-cell-derived SC precursors or a composition comprising thereof, matured SCs or a composition comprising thereof, can be administered or provided systemically or directly to a subject. In certain embodiments, the presently disclosed stem-cell-derived SC precursors or a composition comprising thereof, matured SCs or a composition comprising thereof, are directly injected into an organ of interest (e.g., an organ affected by a Schwann cell defects related disorder (e.g., peripheral neuropathy). The presently disclosed stem-cell-derived SC precursors or a composition comprising thereof, matured SCs or a composition comprising thereof, can be administered (injected) directly to a subject's any part of the body having effective nerves, including, but not limited to, brain and spinal cord.

The presently disclosed stem-cell-derived SC precursors or a composition comprising thereof, matured SCs or a composition comprising thereof, can be administered in any physiologically acceptable vehicle. Pharmaceutical compositions comprising a pharmaceutically acceptable carrier and the presently disclosed stem-cell-derived SC precursors or matured SCs, also provided. The presently disclosed stem-cell-derived SC precursors or a composition comprising thereof, matured SCs or a composition comprising thereof, or a pharmaceutically acceptable carrier can be administered via localized injection, orthotropic (OT) injection, systemic injection, intravenous injection, or parenteral administration. In certain embodiments, the presently disclosed stem-cell-derived SC precursors or a composition comprising thereof, matured SCs or a composition comprising thereof, are administered to a subject via localized injection.

The presently disclosed stem-cell-derived SC precursors or a composition comprising thereof, matured SCs or a composition comprising thereof, can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating the compositions of the presently disclosed subject matter, e.g., a composition comprising the presently disclosed stem-cell-derived SC precursors or matured SCs, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the presently disclosed stem-cell-derived SC precursors or a composition comprising thereof, and/or matured SCs or a composition comprising thereof.

Those skilled in the art will recognize that the components of the compositions should be selected to be chemically inert and will not affect the viability or efficacy of the presently disclosed stem-cell-derived SC precursors or matured SCs. This will present no problem to those skilled in chemical and pharmaceutical principles, or problems can be readily avoided by reference to standard texts or by simple experiments (not involving undue experimentation), from this disclosure and the documents cited herein.

In certain non-limiting embodiments, the SC precursors and SCs described herein are comprised in a composition that further comprises a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties).

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the Schwann cell related disorder (e.g., DPN), or otherwise reduce the pathological consequences of the Schwann cell related disorder (e.g., DPN). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

In certain embodiments, an effective amount of the presently disclosed stem-cell-derived SC precursors, matured SCs, is an amount sufficient to regenerate PNS and/or CNS, an amount sufficient to prevent myelin damages, an amount sufficient to repair/treat myelin damages, an amount sufficient to prevent a Schwann cell related disorder, and/or an amount sufficient to treat (e.g., slow the progression of, alleviate and/or reduce the symptoms) of a Schwann cell related disorder. The quantity of the presently disclosed stem-cell-derived SC precursors or matured SCs to be administered will vary for the subject being treated. In certain embodiments, from about $1\times10^4$ to about $1\times10^{10}$, from about $1\times10^4$ to about $1\times10^5$, from about $1\times10^5$ to about $1\times10^9$, from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ the presently disclosed stem-cell-derived SC precursors or matured SCs are administered to a subject. In certain embodiments, from about $1\times10^5$ to about $1\times10^7$ the presently disclosed stem-cell-derived SC precursors or matured SCs are administered to a subject, e.g., a subject suffering from peripheral neuropathy, e.g., a subject suffering from DPN. The precise determination of what would be considered an effective dose may be based on factors individual to each subject, including their size, age, sex, weight, and condition of the particular subject. Dosages can be readily ascertained by those skilled in the art from this disclosure and the knowledge in the art.

In certain embodiments, the cells that are administered to a subject for regeneration of PNS and/or CNS, for prevention and/or treatment/repair of myelin damages, and/or for prevention and/or treatment of a Schwann cell related disorder (e.g., peripheral neuropathy) are a population of matured Schwann cells that are differentiated/matured from the presently disclosed stem-cell-derived Schwann cell precursors.

5. Kits

The presently disclosed subject matter provides kits for inducing differentiation of neural crest lineage cells to SC precursors. In certain embodiments, the kit comprises one or more Wnt activator, one or more FGF activator, and optionally one or more SC differentiation inducer described herein. In certain embodiments, the kit further comprises instructions for inducing differentiation of neural crest lineage cells (e.g., cells expressing one or more neural crest lineage marker) to SC precursors (e.g., cells that express one or more Schwann cell precursor marker). In certain embodiments, the instructions comprise contacting the neural crest lineage cells with or more Wnt activator, one or more FGF activator, and optionally one or more SC differentiation inducer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days, to produce SC precursors. In certain embodiments, the instructions comprise contacting the neural crest lineage cells the one or more Wnt activator, one or more FGF activator, and optionally one or more SC differentiation inducer for at least about 10 days to produce SC precursors. In certain embodiments, the instructions comprise contacting the neural crest lineage cells with the one or more Wnt activator, one or more FGF activator, and optionally one or more SC differentiation inducer for up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce SC precursors. In certain embodiments, the instructions comprise contacting the neural crest lineage cells with the one or more Wnt activator, one or more FGF activator, and optionally one or more SC differentiation inducer for between about 3 days and about 5 days, between about 5 days and about 10 days, between about 10 days and about 15 days, between about 15 days and about 20 days, between about 20 days and about 25 days, or between about 25 days and about 30 days, to produce SC precursors. In certain embodiments, the instructions comprise contacting the neural crest lineage cells with the one or more Wnt activator, one or more FGF activator, and optionally one or more SC differentiation inducer for between about 10 days and about 15 days to produce SC precursors. In certain embodiments, the instructions comprise contacting the neural crest lineage cells with the one or more Wnt activator, one or more FGF activator, and optionally one or more SC differentiation inducer for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days, to produce SC precursors. In certain embodiments, the instructions comprise contacting the neural crest lineage cells with the one or more Wnt activator, one or more FGF activator, and optionally one or more SC differentiation inducer for 14 days to produce SC precursors. In certain embodiments, the instructions comprise contacting the neural crest lineage cells with the one or more Wnt activator, one or more FGF activator, and optionally one or more SC differentiation inducer for 15 days to produce SC precursors.

The presently disclosed subject matter also provides kits for inducing differentiation of stem cells. In certain embodiments, the kit comprises one or more inhibitor of transforming growth factor beta (TGFβ/Activin-Nodal signaling one or more activator of wingless (Wnt) signaling, one or more activator of FGF signaling, and optionally one or more molecule that induces Schwann cell differentiation. In certain embodiments, the kit further comprises instructions for inducing differentiation of the stem cells into a population of differentiated SC precursors, e.g., cells that express one or more Schwann cell precursor marker.

In certain embodiments, the instructions comprise contacting the cells with the inhibitor(s), activator(s) and inducer(s) in a specific sequence. The sequence of contacting the inhibitor(s), activator(s) and inducer(s) can be determined by the cell culture medium used for culturing the stem cells.

In certain embodiments, the instructions comprise contacting the cells with the one or more activator of FGF signaling and optionally the one or more SC differentiation inducer for at least about 3 days. In certain embodiments, the instructions comprise contacting the cells with the one or more activator of FGF signaling and optionally the one or more SC differentiation inducer for 15 days. In certain embodiments, the instructions comprise contacting the cells with the one or more activator of FGF signaling and optionally the one or more SC differentiation inducer for 14 days.

In certain embodiments, the instructions comprise initially contacting the cells with the one or more activator of Wnt signaling no later than about 4 days (e.g., concurrently (on the same day), e.g., between about 1 days and about 4 days, e.g., about 1 day, about 2 days, about 3 days, or about 4 days) from the initial contact of the stem cells with the one or more inhibitor of TGFβ/Activin-Nodal signaling. In certain embodiments, the instructions comprise initially contacting the cells with the one or more activator of Wnt signaling about 2 days from/after the initial contact of the stem cells with the one or more inhibitor of TGFβ/Activin-Nodal signaling.

In certain embodiments, the kit further comprises one or more inhibitor of Small Mothers Against Decapentaplegic (SMAD) signaling. In certain embodiments, the instructions comprise contacting the stem cells with the one or more inhibitor of TGFβ/Activin-Nodal signaling and the one or more inhibitor of SMAD signaling concurrently.

In certain embodiments, the instructions comprise initially contacting the one or more activator of FGF signaling and optionally the one or more SC differentiation inducer with the cells no later than about 20 days from the initial contact of the stem cells with the one or more inhibitor of TGFβ/Activin-Nodal signaling. In certain embodiments, the instructions comprise initially contacting the one or more activator of FGF signaling and optionally the one or more SC differentiation inducer with the cells at least about 5 days from the initial contact of the stem cells with the one or more inhibitor of TGFβ/Activin-Nodal signaling. In certain embodiments, the instructions comprise initially contacting the one or more activator of FGF signaling and optionally the one or more SC differentiation inducer with the cells is about 5 days and about 20 days (e.g., about 5 days, about 6 days, about 7 days, about 8 days, about 9 days, about 10 days, about 11 days, about 12, days, about 13 days, about 14 days, about 15 days, about 16 days, about 17 days, about 18 days, about 19 days, or about 20 days) from the initial contact of the stem cells with the one or more inhibitor of TGFβ/Activin-Nodal signaling.

In certain embodiments, the instructions comprise initially contacting the one or more activator of FGF signaling and optionally the one or more SC differentiation inducer with the cells 10 days from the initial contact of the stem cells with the one or more inhibitor of TGFβ/Activin-Nodal signaling. In certain embodiments, the instructions comprise initially contacting the one or more activator of FGF signaling and optionally the one or more SC differentiation inducer with the cells is about 11 days from the initial contact of the stem cells with the one or more inhibitor of TGFβ/Activin-Nodal signaling.

In certain embodiments, the instructions comprise contacting the stem cells with the one or more inhibitor of TGFβ/Activin-Nodal signaling for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days. In certain embodiments, the instructions comprise contacting the stem cells with the one or more inhibitor of TGFβ/Activin-Nodal signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days. In certain embodiments, the instructions comprise contacting the stem cells with the one or more inhibitor of TGFβ/Activin-Nodal signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days. In certain embodiments, the instructions comprise contacting the stem cells with the one or more inhibitor of TGFβ/Activin-Nodal signaling for between 10 days and about 15 days. In certain embodiments, the instructions comprise contacting the stem cells with the one or more inhibitor of TGFβ/Activin-Nodal signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day. In certain embodiments, the instructions comprise contacting the stem cells with the one or more inhibitor of TGFβ/Activin-Nodal signaling for about 11 days. In certain embodiments, the instructions comprise contacting the stem cells with the one or more inhibitor of TGFβ/Activin-Nodal signaling for about 10 days.

In certain embodiments, the instructions comprise contacting the stem cells with the one or more inhibitor of SMAD signaling for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days. In certain embodiments, the instructions comprise contacting the stem cells with the one or more inhibitor of SMAD signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days. In certain embodiments, the instructions comprise contacting the stem cells with the one or more inhibitor of SMAD signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days. In certain embodiments, the instructions comprise contacting the stem cells with the one or more inhibitor of SMAD signaling for between 10 days and about 15 days. In certain embodiments, the instructions comprise contacting the stem cells with the one or more inhibitor of SMAD signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day. In certain embodiments, the instructions comprise contacting the stem cells with the one or more inhibitor of SMAD signaling for about 11 days. In certain embodiments, the instructions comprise contacting the stem cells with the one or more inhibitor of SMAD signaling for about 10 days.

In certain embodiments, the instructions comprise contacting the cells with the one or more activator of Wnt signaling for at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, or at least about 29 days, at least about 30 days, at least about 31 days, at least about 32 days, at least about 33 days, at least about 34 days, at least about 35 days, at least about 36 days, at least about 37 days, at least about 38 days, at least about 39 days, or at least about 40 days. In certain embodiments, the instructions comprise contacting the cells with the one or more activator of Wnt signaling for up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, up to about 30 days, up to about 31 days, up to about 32 days, up to about 33 days, up tot about 34 days, up to about 35 days, up to about 36 days, up to about 37 days, up to about 38 days, up to about 39 days, up to about 40 days, up to about 41 days, up to about 42 days, up to about 43 days, up to about 44 days, up to about 45 days, up to about 46 days, up to about 47 days, up to about 48 days, up to about 49 days, up to about 50 days, up to about 51 days, up to about 52 days, up to about 53 days, up to about 54 days, up to about 55 days, up to about 56 days, up to about 57 days, up to about 58 days, up to about 59 days or up to about 60 days. In certain embodiments, the instructions comprise contacting the cells with the one or more activator of Wnt signaling for between about 14 days and about 20 days, between about 20 days and about 25 days, between about 25 days and about 30 days, between about 30 days and about 35 days, between about 35 days and about 40 days, between about 40 days and about 45 days, between about 45 days and about 50 days, between about 50 days and about 55 days, or between about 55 days and about 60 days. In certain embodiments, the instructions comprise contacting the cells with the one or more activator of Wnt signaling for between 20 days and about 30 days. In certain embodiments, the instructions comprise contacting the cells with the one or more activator of Wnt signaling for between 25 days and about 30 days. In certain embodiments, the instructions comprise contacting the cells with the one or more activator of Wnt signaling for about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days or about 60 days. In certain embodiments, the instructions comprise contacting the cells with the one or more activator of Wnt signaling for about 26 days. In certain embodiments, the instructions comprise contacting the cells with the one or more activator of Wnt signaling for about 25 days. In certain embodiments, the instructions comprise contacting the cells with the one or more activator of Wnt signaling for about 24 days. In certain embodiments, the instructions comprise contacting the cells with the one or more activator of Wnt signaling for about 23 days.

In certain embodiments, the instructions comprise contacting the cells with the one or more activator of FGF signaling and optionally the one or more SC differentiation inducer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days, to produce SC precursors. In certain embodiments, the instructions comprise contacting the cells with the one or more activator of FGF signaling and optionally the one or more SC differentiation inducer for at least about 10 days to produce SC precursors. In certain embodiments, the instructions comprise contacting the cells with the one or more activator of FGF signaling and optionally the one or more SC differentiation inducer for up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce SC precursors. In certain embodiments, the instructions comprise contacting the cells with the one or more one or more molecule that induces Schwann cell differentiation and one or more activator of FGF signaling for between about 3 days and about 10 days, between about 5 days and about 10 days, between about 10 days and about 15 days, between about 15 days and about 20 days, between about 20 days and about 25 days, or between about 25 days and about 30 days, to produce SC precursors. In certain embodiments, the cells are contacted with the one or more activator of FGF signaling and optionally the one or more SC differentiation inducer for between about 10 days and about 15 days to produce SC precursors. In certain embodiments, the instructions comprise contacting the cells with the one or more activator of FGF signaling and optionally the one or more SC differentiation inducer for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days, to produce SC precursors. In certain embodiments, the instructions comprise contacting the cells with the one or more activator of FGF signaling and optionally the one or more SC differentiation inducer for about 14 days to produce SC precursors. In certain embodiments, the instructions comprise contacting the cells with the one or more activator of FGF signaling and optionally the one or more SC differentiation inducer for about 14 days to produce SC precursors.

In certain embodiments, the instructions comprise contacting the cells with one or more inhibitor of TGFβ/Activin-Nodal signaling and the one or more inhibitor of SMAD signaling for about 11 days; with the one or more activator of Wnt signaling for about 23 days; and with the one or more activator of FGF signaling and optionally the one or more SC differentiation inducer for about 14 days, to produce SC precursors.

In certain embodiments, the instructions comprise contacting the cells with one or more inhibitor of TGFβ/Activin-Nodal signaling and the one or more inhibitor of SMAD signaling for about 11 days; with the one or more activator of Wnt signaling for about 25 days; and with the one or more activator of FGF signaling and optionally the one or more SC differentiation inducer for about 14 days, to produce SC precursors.

In certain embodiments, the kit further comprises one or more molecule that enhance SC differentiation ("Sc differentiation enhancer"), and instructions for inducing maturation of SC precursors to SCs. In certain embodiments, the instructions for inducing maturation of SC precursors to SCs comprise contacting the SC precursors with the one or more FGF activator, one or more Schwann cell differentiation inducer, and optionally one or more SC differentiation enhancer to produce SCs. In certain embodiments, the instructions for inducing maturation of SC precursors to SCs comprise contacting the SC precursors with the one or more FGF activator, the one or more Schwann cell differentiation inducer, and optionally the one or more SC differentiation enhancer for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days, to produce SCs. In certain embodiments, the instructions for inducing maturation of SC precursors to SCs comprise contacting the SC precursors with the one or more FGF activator, the one or more Schwann cell differentiation inducer, and optionally the one or more SC differentiation enhancer for between about 3 days and about 40 days, between about 3 days and about 35 days, between about 3 days and about 30 days, between about 3 days and about 25 days, between about 3 days and about 20 days, between about 3 days and about 15 days, between about 10 days and about 40 days, between about 10 days and about 20 days, between about 20 days and about 40 days, between about 20 days and about 30 days, or between about 30 days and about 40 days, to produce SCs. In certain embodiments, the instructions for inducing maturation of SC precursors to SCs comprise contacting the SC precursors with the one or more FGF activator, the one or more Schwann cell differentiation inducer, and optionally the one or more SC differentiation enhancer for between about 3 days and about 15 days to produce SCs. In certain embodiments, the instructions for inducing maturation of SC precursors to SCs comprise contacting the SC precursors with the one or more FGF activator, the one or more Schwann cell differentiation inducer, and optionally the one or more SC differentiation enhancer for between about 30 days and about 40 days to produce SCs. In certain embodiments, the instructions for inducing maturation of SC precursors to SCs comprise contacting the SC precursors with the one or more FGF activator, the one or more Schwann cell differentiation inducer, and optionally the one or more SC differentiation enhancer for 10 days to produce SCs. In certain embodiments, the instructions for inducing maturation of SC precursors to SCs comprise contacting the SC precursors with the one or more FGF activator, the one or more Schwann cell differentiation inducer, and optionally the one or more SC differentiation enhancer for about 11 days to produce SCs. In certain embodiments, the instructions for inducing maturation of SC precursors to SCs comprise contacting the SC precursors with the one or more FGF activator, the one or more Schwann cell differentiation inducer, and optionally the one or more SC differentiation enhancer for about 35 days to produce SCs.

Furthermore, the presently disclosed subject matter provides for kits for regeneration of PNS and/or CNS, prevention and/or repair of myelin damages, and/or for treating and/or preventing a Schwann cell related disorder (e.g., peripheral neuropathy, e.g., DPN). In certain embodiments, the kit comprises an effective amount of a population of the presently disclosed stem-cell-derived SC precursors or a composition comprising thereof, or matured SCs or a composition comprising thereof in unit dosage form. In certain embodiments, the kit comprises a sterile container which contains the therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit comprises instructions for administering a population of the presently disclosed stem-cell-derived SC precursors or a composition comprising thereof, or matured SCs or a composition comprising thereof to a subject, e.g., a subject suffering from a Schwann cell related disorder (e.g., peripheral neuropathy, e.g., DPN). The instructions can comprise information about the use of the cells or composition for regeneration of PNS and/or CNS, prevention and/or repair of myelin damages, and/or for treating and/or preventing a Schwann cell related disorder (e.g., peripheral neuropathy, e.g., DPN). In certain embodiments, the instructions comprise at least one of the following: description of the therapeutic agent; dosage schedule and administration for regeneration of PNS and/or CNS, prevention and/or repair of myelin damages, and/or for treating and/or preventing a Schwann cell related disorder (e.g., peripheral neuropathy, e.g., DPN) or symptoms thereof; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

EXAMPLES

The presently disclosed subject matter will be better understood by reference to the following Example, which is provided as exemplary of the presently disclosed subject matter, and not by way of limitation.

Example 1

Summary

The inventors developed a method of highly efficient generation and prospective isolation of Schwann cell precursors and Schwann Cells derived from human stem cells (e.g., hPSC). The stem-cell-derived SCs were capable of myelinating hESC-derived sensory neurons in vitro and accelerating the maturation of hESC-derived motor neurons. The stem-cell-derived SCs were also capable of efficiently engraft in a rat model of PNS injury in vivo. Transplanted stem-cell-derived SCs in injured sciatic nerves of rats contributed to myelination of regenerating host axons and promoted appropriate ion channel localization in newly myelinated fibers.

Methods and Materials

Culture of Undifferentiated Human Embryonic Stem Cells (hESCs)

hESC line H9 (WA-09) and derivatives (SOX10::GFP; SYN::ChR2-YFP; SYN::YFP; PHOX2B:GFP; EF1::RFP EDNRB−/−) as well as 2 independent hiPSC lines (healthy and Familial Dysautonomia, Sendai-based, OMSK (Cytotune)) were maintained on mouse embryonic fibroblasts (MEF, Global Stem, Rockville, MD) in KSR (Life Technologies, 10828-028) containing hESC medium (Chambers et. al., 2009). Cells were subjected to mycoplasma testing at monthly intervals and STR profiled to confirm cell identity at the initiation of the study.

Neural Crest Induction and Induction and Expansion of Schwann Cells from hESCs hESCs were plated on matrigel (BD Biosciences, 354234) coated dishes ($10^5$ cells/$cm^2$) in hESC medium containing 10 nM FGF2 (R&D Systems, 233-FB-001MG/CF). Differentiation was initiated in knockout serum replacement (KSR) medium (KO DMEM+15% KSR, L-glutamine (Life Technologies, 25030-081), NEAA (Life Technologies, 11140-050) containing LDN193189 (100 nM, Stemgent, Cambridge, MA) and SB431542 (10 μM, Tocris, Ellisville, MI). The KSR medium was gradually replaced with increasing amounts of N2 medium from day 4 through day 10 as described previously ((Chambers et. al., 2009). For Cranial NC (CNC) induction, cells are treated with 3 μM CHIR99021 (Tocris Bioscience, 4423) in addition to LDN and SB from day 2 through day 11. CNS precursor control cells were generated by treatment with LDN and SB from day 0 through day 11 as previously described (Chambers et al., 2009). Throughout the Example, day 0 was the day the medium was switched from hESC medium to LDN and SB containing medium. Days of differentiation in text and figures refer to the number of days since the pluripotent stage (day 0).

At day 11, NC cells were aggregated into 3D spheroids (5 million cells/well) in Ultra Low Attachment 6-well culture plates (Fisher Scientific, 3471) and cultured in Neurobasal (NB) medium supplemented with L-Glutamine (Gibco, 25030-164), N2 (Stem Cell Technologies, 07156) and B27 (Life Technologies, 17504044) containing CHIR (3 uM, Tocris Bioscience, 4423) and FGF2 (10 nM, R&D Systems, 233-FB-001MG/CF) and NRG1 (10 ng/ml, R&D 378-SM-025). After 14 days of suspension culture, the spheroids are plated on Poly Ornithine/Laminin/Fibronectin (PO/LM/FN)

coated dishes (prepared as described previously) in Neurobasal (NB) medium supplemented with L-Glutamine (Gibco, 25030-164), N2 (Stem Cell Technologies, 07156) and B27 (Life Technologies, 17504044) containing NRG1 (20 ng/ml, R&D 378-SM-025), FGF2 (10 nM, R&D Systems, 233-FB-001MG/CF) and cAMP (100 mM, Sigma, D0260) (Lee G et. al., 2007). The SC precursors migrate out of the plated spheroids and differentiate into SCs within 10 days. For long-term expansion, cells were cultured in Schwann cell medium (Sciencell, 1701) on PO/LM/FN coated dishes. The cells were fixed for immunostaining or harvested for gene expression analysis at Day 25, Day 35 Day 50, Day 60, and Day 100 of differentiation.

FACS and Immunofluorescence (IF) Analysis

For IF, the cells were fixed with 4% paraformaldehyde (PFA, Affymetrix-USB, 19943) for 20 minutes, then blocked and permeabilized using 1% Bovine Serum Albumin (BSA, Thermo Scientific, 23209) and 0.3% triton X-100 (Sigma, T8787). The cells were then incubated in primary antibody solutions overnight at 4° C. (Celsius) and stained with fluorophore conjugated secondary antibodies at RT for 1 hour, the stained cells were then incubated with DAPI (1 ng/ml, Sigma, D9542-5MG) and washed several times before imaging. For Flow Cytometry analysis, the cells were dissociated with Accutase (Innovative Cell Technologies, AT104) and fixed and permeabilized using BD Cytofix/Cytoperm (BD Bioscience, 554722) solution, then washed, blocked and permeabilized using BD Perm/Wash buffer (BD Bioscience, 554723) according to the manufacturer's instructions. The cells were then stained with primary (overnight at 4) and secondary (30 min at room temperature) antibodies and analyzed using a flow Cytometer (FlowJo software). A list of primary antibodies and dilutions is provided in Table 5.

Surface Marker Screening

Screening for specific surface antigens was performed using BD Lyoplate Library® (BD, 560747) on hESC-SCs at day 80 of differentiation. Cells were plated in 96 well plates (10,000 cells/well) and stained with primary and secondary antibodies according to manufacturer's instructions. The stained wells were fixed for total plate imaging and quantification. The percentage of double positive cells out of total GFAP was quantified for each antibody. Top hits (>60% double positive) were validated further using flow cytometry.

Gene Expression Analysis

For RNA sequencing, total RNA was extracted using RNeasy RNA purification kit (Qiagen, 74106). For qRT-PCR assay, total RNA samples were reverse transcribed to cDNA using Superscript II Reverse Transcriptase (Life Technologies, 18064-014). qRT-PCR reactions were set up using QuantiTect SYBR Green PCR mix (Qiagen, 204148). Each data point represents three independent biological replicates. RNA-seq reads were mapped to the human reference genome (hg19) using TopHat v2.0. TopHat was run with default parameters with exception to the coverage search. Alignments were then quantified using HTSeq and differential gene expression was calculated using DESeq normalized to the cranial neural crest sample.

Viability Assay

To monitor the viability of SCs, cells were assayed for LDH activity using CytoTox 96 cytotoxicity assay kit (Promega, G1780). Briefly, the cells are plated in 96 well plates at 30,000 cells/cm$^2$. The supernatant and the cell lysate were harvested 24 hours later and assayed for LDH activity using a plate reader (490 nm absorbance). Viability was calculated by dividing the LDH signal of the lysate by total LDH signal (from lysate plus supernatant). The cells were cultured in Schwann cell medium (Sciencell, 1701) on PO/LM/FN coated dishes during the assay.

Calcium Imaging

MN-SC co-cultures were subjected to calcium imaging at days 40 and 70 post-coculture as previously described (Barreto-Chang and Dolmetsch, 2009). Briefly, cells were incubated with 5 μM Fluo-4 (Life Technologies) for 30 min at 37° C. prior to imaging. Coverslips were mounted in a FCS2 imaging chamber (Bioptechs), and cells were perfused with normal Tyrode's saline solution as previously described with the addition of 0.1% BSA w/v. For activation, cells were perfused with Tyrode's solution containing glutamate (50 or 100 μM). Images were acquired every 5 s at 340 nm and 380 nm wavelengths using an Axiovert 200M Inverted Microscope with a 40×1.3 numerical aperture oil immersion objective (Zeiss). Ratiometric analysis was performed using Metamorph Software (Molecular Devices).

Transplantation of hESC-SCs in Rat Sciatic Nerves and Histological Assessment

All procedures were performed following NIH guidelines, and were approved by the local Institutional Animal Care and Use Committee (IACUC). Rats were placed under isoflurane gas anesthesia and both sciatic nerves were exposed below the sciatic notch and crushed using Dumont #5 forceps for 30 seconds twice in the same location. Immediately afterwards, a cell suspension of $3\times10^4$ hES cells/μl Schwann cells were transplanted through injection of ~3-4 μl atproximal and distal to the crush site with a glass micropipette. Survival times ranged from 2 to 8 weeks. Immunohistochemistry Rats were fixed through intracardiac perfusion of 4% paraformaldehyde 0.1M PBS. Sciatic nerves were dissected from rats at 2, 3, 4, 8 wks after crush lesion and transplantation. After dissection sciatic nerves where prepared by placing them in 30% sucrose in 0.1M PBS overnight and embedding them in OCT blocks for cryosectioning, or, by removing the perineurium and teasing them in cold 0.1M Phosphate Buffer (pH 7.4). Some nerves were teased after perfusion and immunostained to examine individual axons. Regenerated axons distal to the crush site were analyzed.

Statistical Analysis

Data are presented as mean±SEM and were derived from at least 3 independent experiments. Data on replicates (n) is given in figure legends. Statistical analysis was performed using the Student t-test (comparing 2 groups) or ANOVA with Dunnett test (comparing multiple groups against control). Distribution of the raw data approximated normal distribution (Kolmogorov Smirnov normality test) for data with sufficient number of replicates to test for normality. Survival analysis was performed using log rank (Mantel-Cox) test. Z-scores for primary hits were calculated as $Z=(x-\mu)/\sigma$. X is the migration score value and is 3 for all hit compounds. $\mu$ is the mean migration score value and $\sigma$ is the standard deviation for all compounds and DMSO controls

Results

Derivation and Prospective Isolation of SC Lineages from hESCs

To dissect the cell type specific mechanisms of sensory nerve damage in DPN human sensory neurons and SCs were generated from hPSCs. Methods for induction of sensory neurons from hESCs are described in Cai et al., 2016; Chambers et al., 2012, but the derivation of SCs has remained elusive. Therefore, as a first step towards establishing an hESC model for DPN, an effective strategy to differentiate hESCs into SCs was established.

The inventors' past efforts of deriving SCs relied on the prolonged, 2-3 months, culture of NC-enriched progenitor cells to obtain a small proportion of gliogenic cells (Lee et al., 2007). More recent studies reported on the derivation of SC-like cells from hPSCs but did not show expression of key lineages markers such as SOX10 and failed to demonstrate functional myelination (Liu et al., 2012; Ziegler et al., 2011). During embryonic development, SCs were thought to arise from $SOX10^+$ NC cells in a stepwise process. Based on studies in the mouse and chick embryo, NC first gives rise to SC precursors that associate with neuronal bundles in the developing nerves. The associated neurons express NRG1 and promote survival and further differentiation of SC precursors by activating their ERBB3 receptors (Newbern and Birchmeier, 2010). By E13.5 of mouse development, SC precursors give rise to immature SCs that up regulate lineage markers such as GFAP, S100 and POU3F1 while maintaining the expression of SOX10. Terminal differentiation of SCs into myelinating and non-myelinating fates continues until after birth (Jessen et al., 2015).

Figure 1B:
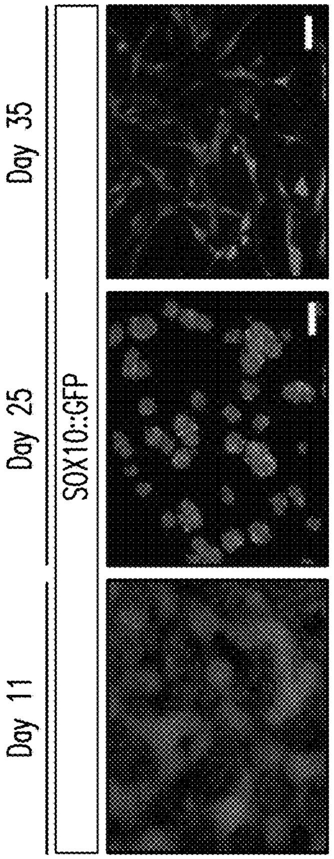
Figure 1C:
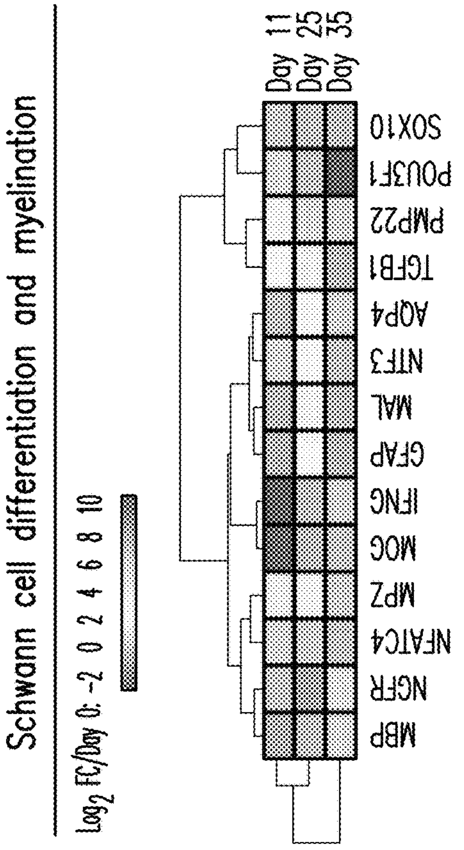
Figure 1D:
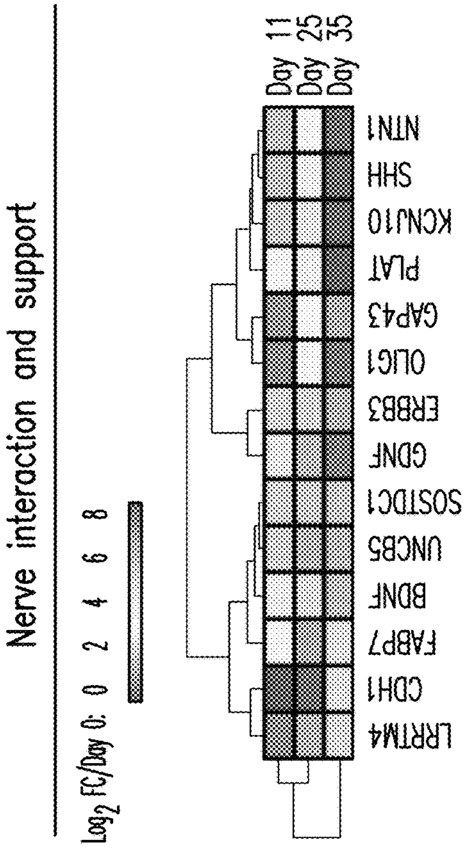
Figure 1E:
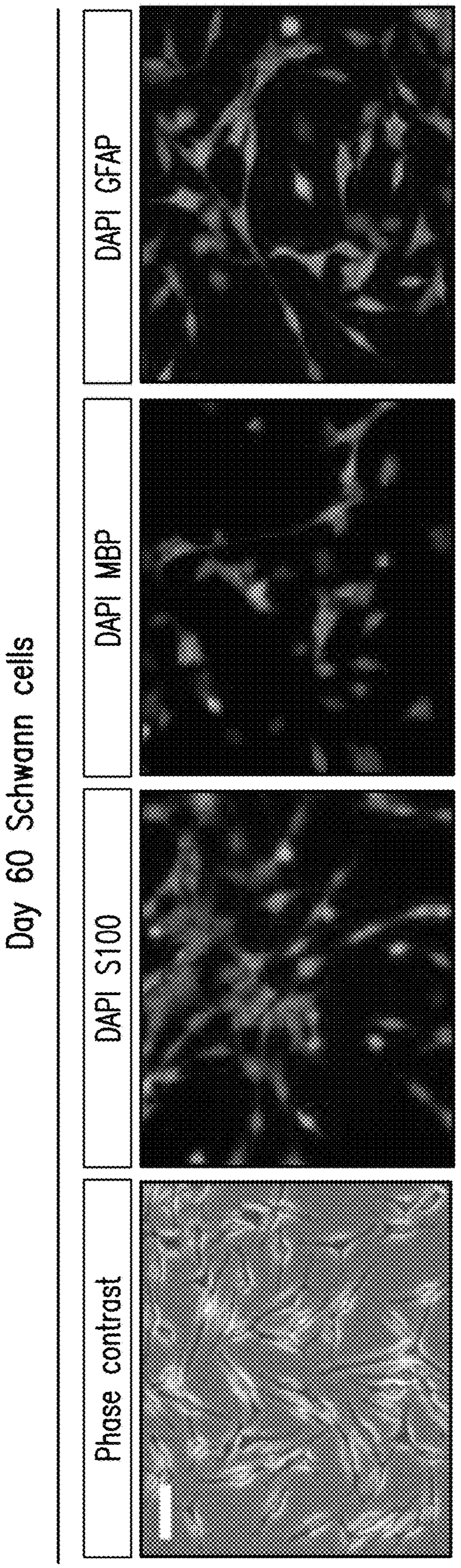
Figure 1F:
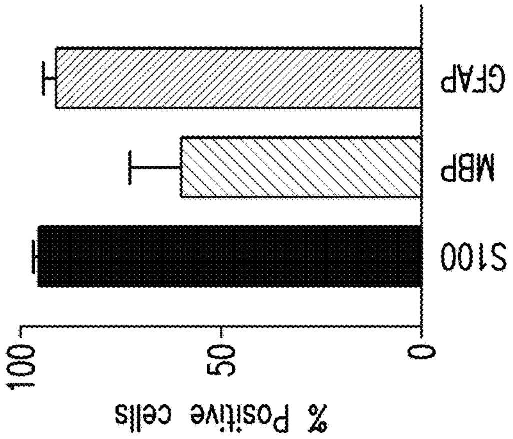
Figure 1G:
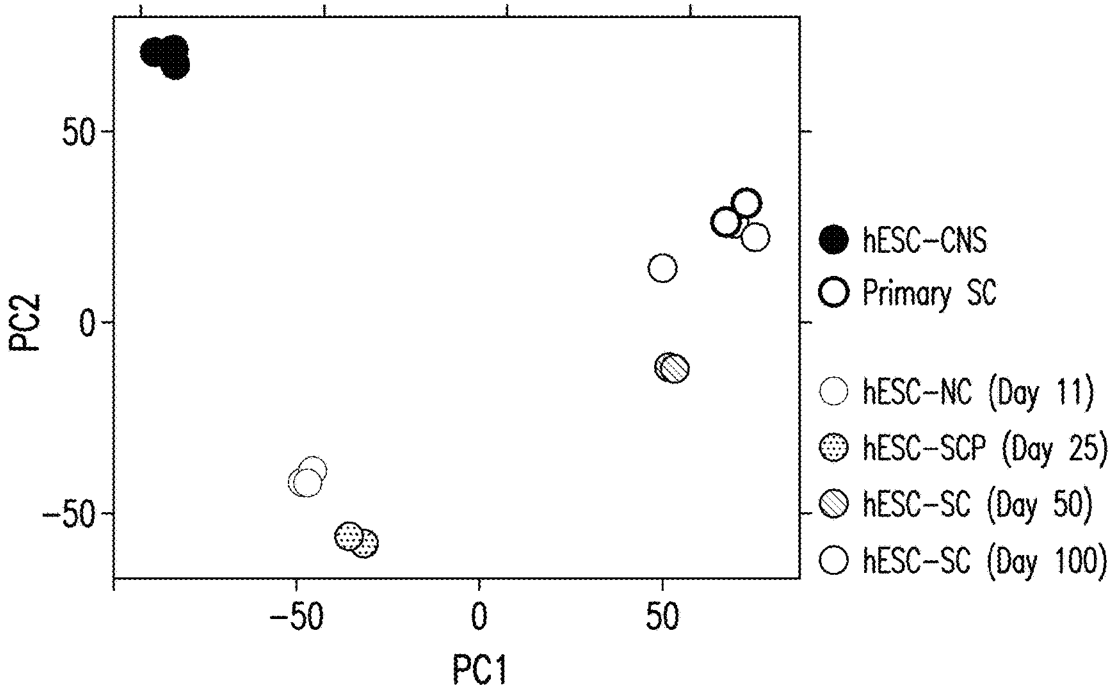
Figure 1H:
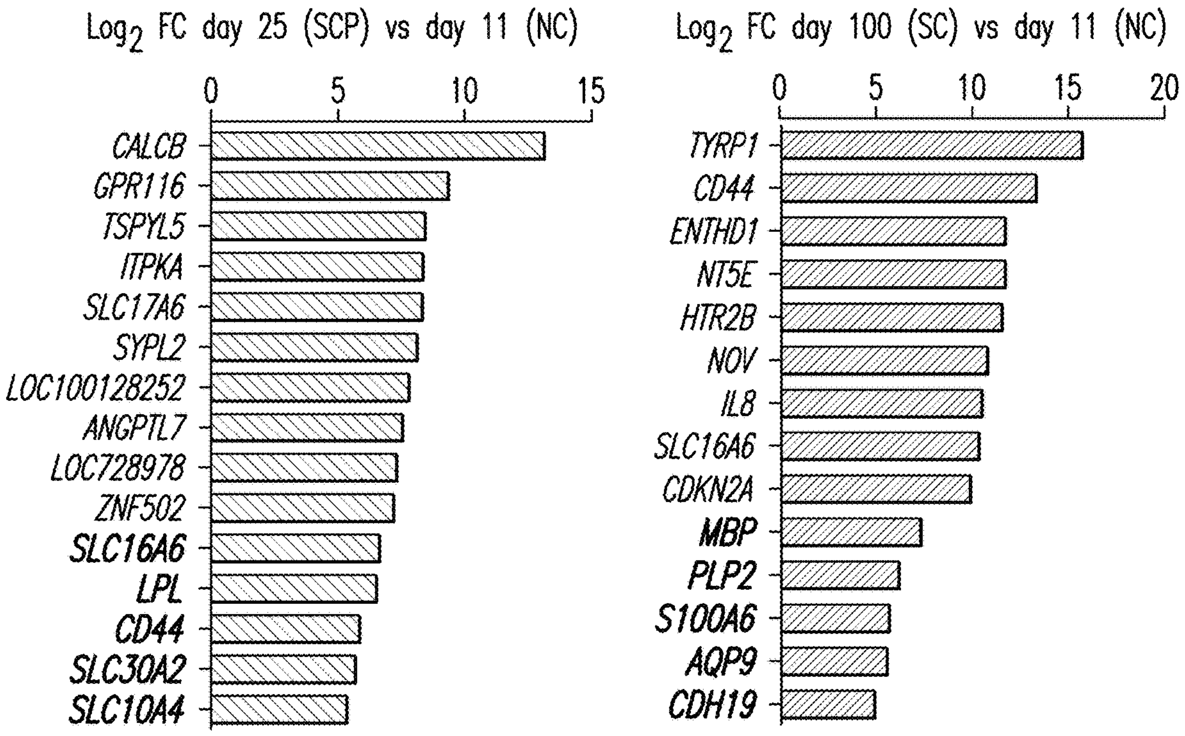
Figure 1I:
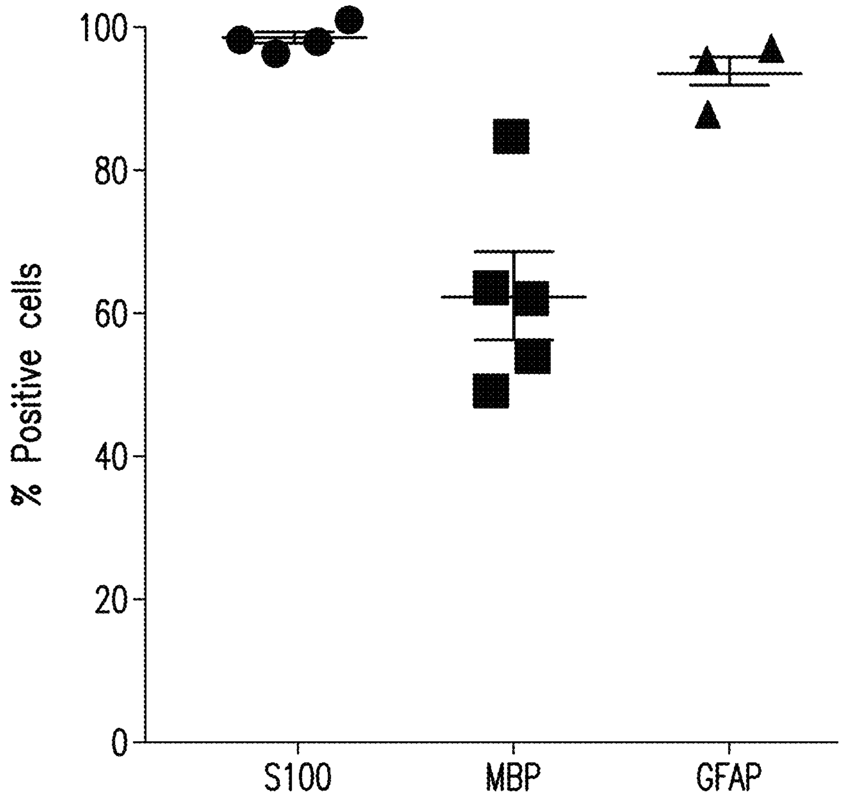
Figure 4A:
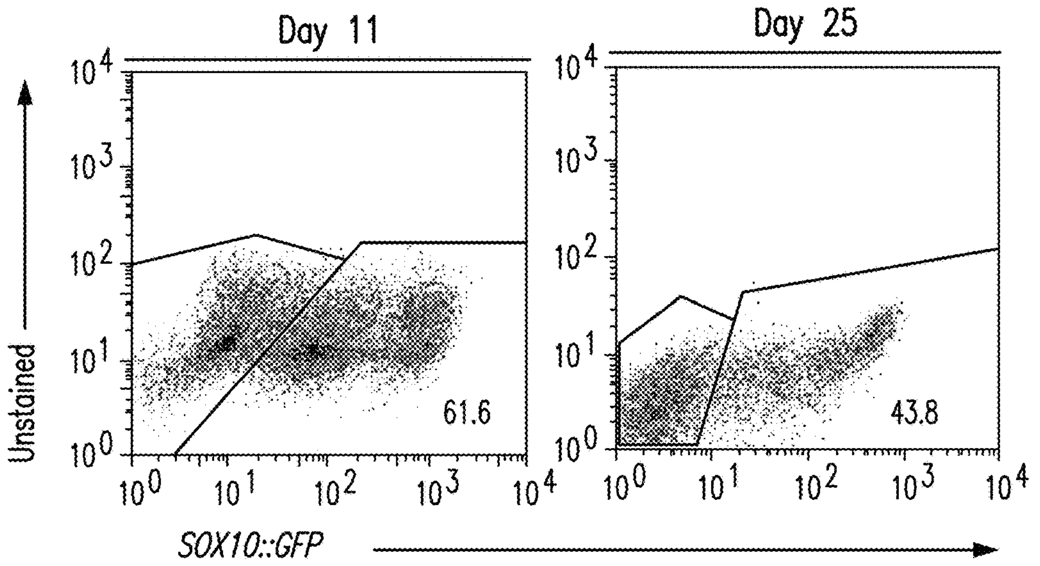
FIGS. 4A-4B: Characterization of hESC-derived SCP and SC lineages.
Figure 4B:
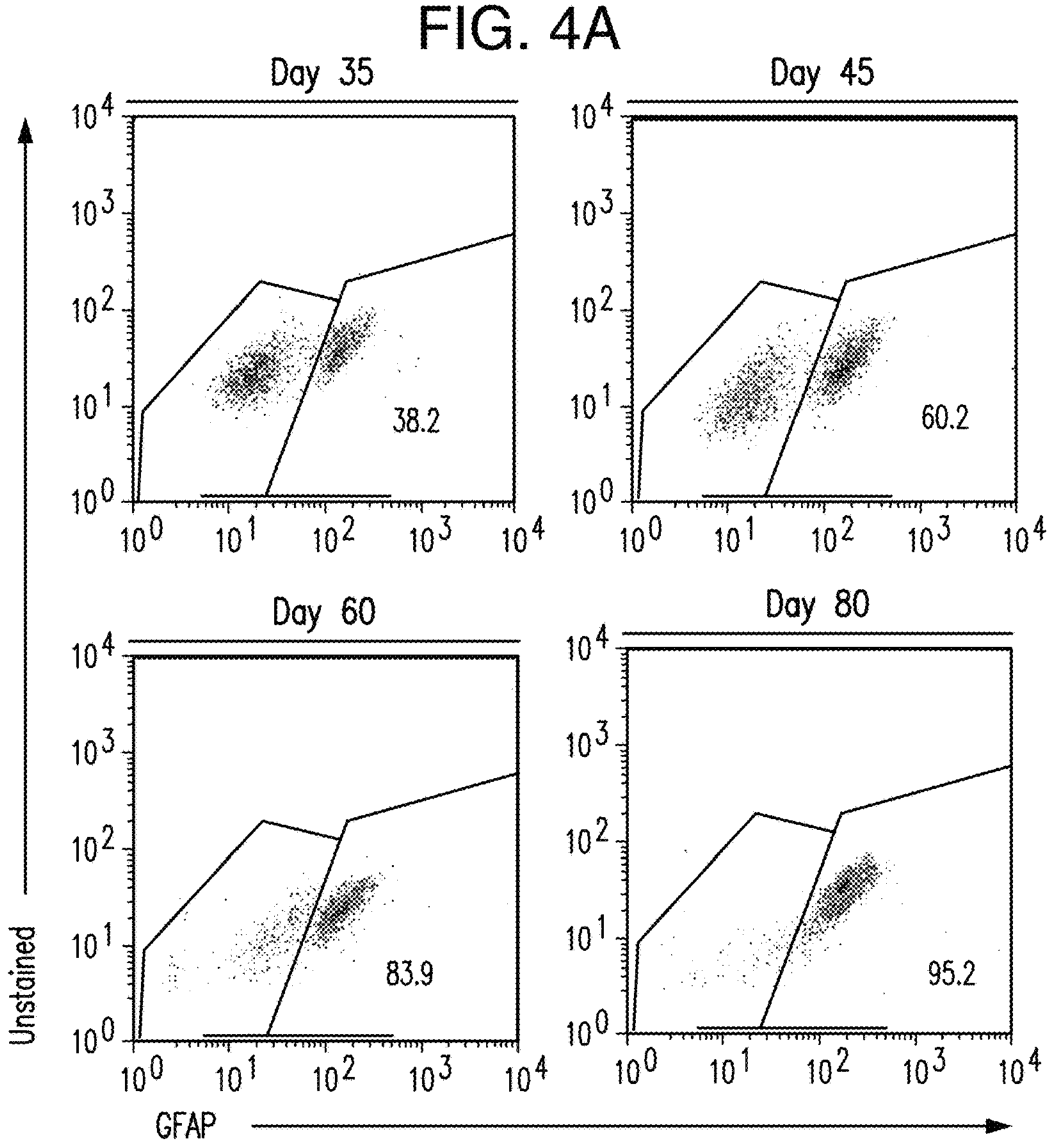

Initial hESC-based NC differentiation protocols relied on the delamination of putative NC cells from neuroepithelial lineages combined with the prospective isolation of $p75^+$ and/or $HNK1^+$ NC precursors (Bajpai et al., 2010; Lee et al., 2007). While those protocols yield various NC-derived lineages, the levels of SOX10 expression are generally low. In contrast, more directed NC induction protocols based on timed exposure to activators of WNT signaling show robust induction of SOX10 in the majority of cells by day 11 of differentiation (Fattahi et al., 2016; Menendez et al., 2011; Mica et al., 2013). Upon further culture, those hESC-derived NC cells can be directed into $SOX10^+$ melanocytes (Mica et al., 2013) but also give rise to $SOX10^-$ mesenchymal and neuronal precursors (Mica et al., 2013). Since SOX10 expression is a key marker retained in SC lineages throughout the development, the inventors first focused on establishing conditions to maintain $SOX10^+$ precursors in culture before instructing them towards a glial fate. The inventors determined the percentage of $SOX10^+$ cells in 2D or 3D NC cultures in the presence of modulators of EGF, FGF, WNT, Notch, TGFβ, BMP, NRG and Endothelin 3 signaling. Combination of a 3D aggregation step and activation of WNT signaling by CHIR99021 in addition to FGF2 and NRG1 treatment resulted in maintenance of SOX10 expression (FIG. 4A) and the induction of S100 and other early SC markers by day 25 (FIGS. 1A-1C). At this stage, treatment of day 25 cultures precursors with FGF2, NRG1 and cAMP for 10 additional days promotes a robust induction of several SC markers such as GFAP, POU3F1, PMP22, MBP, AQP4, MPZ and upregulation of genes involved in neuronal interaction and support including GDNF, ERBB3, and GAP43 among others (FIGS. 1A-1D). Longer-term culture resulted in the enrichment of GFAP+ cells yielding almost homogeneous populations of SCs by day 60-90 (FIG. 4B) based on the expression of S100, MBP and GFAP (FIGS. 1E, 1F and 1I). These hESC-derived populations can proliferate for several additional weeks while maintaining a high percentage of S100, MBP and GFAP expressing SCs (FIGS. 1E, 1F, and 1I).

Figures 2A, 2B, 2C, 2D, 2E:
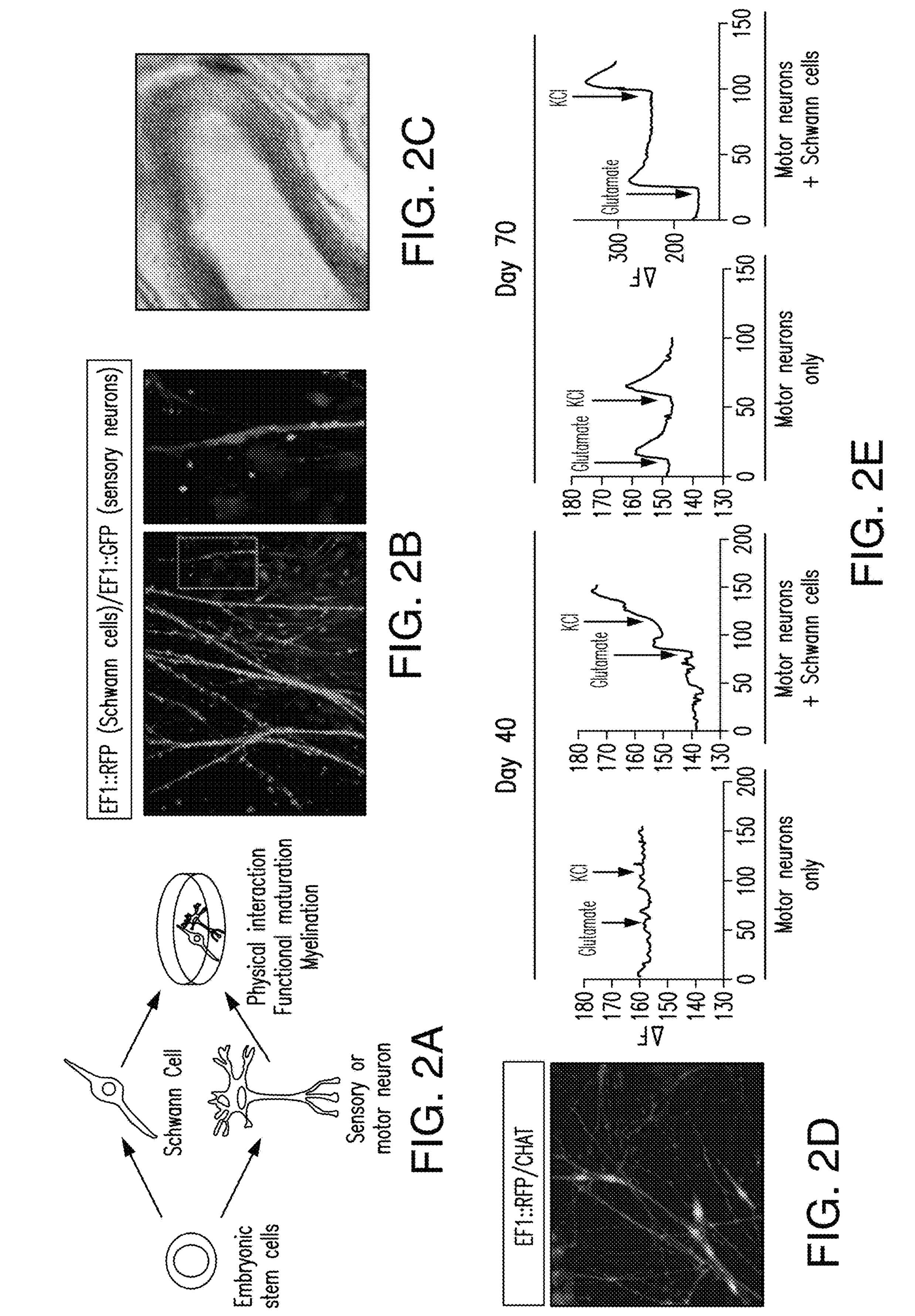
FIGS. 2A-2E: in vitro functional characterization of hESC-SCs and hESC-derived Schwann cells myelinate hESC-derived sensory neurons.
Figure 5A:
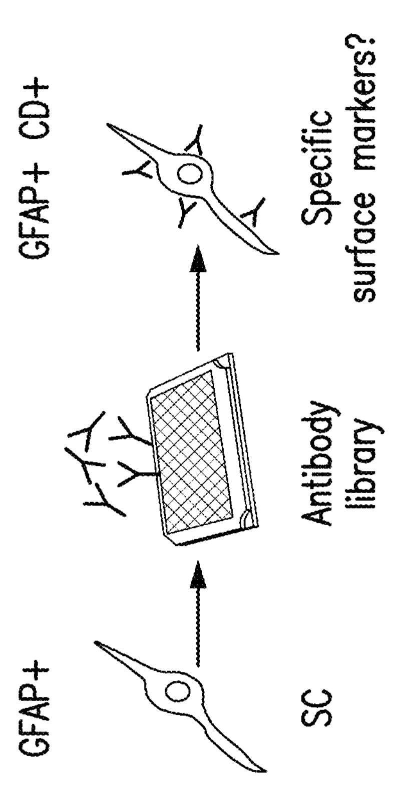
FIGS. 5A-5C: Antibody screen identifies novel surface markers for human SCs.
Figure 5B:
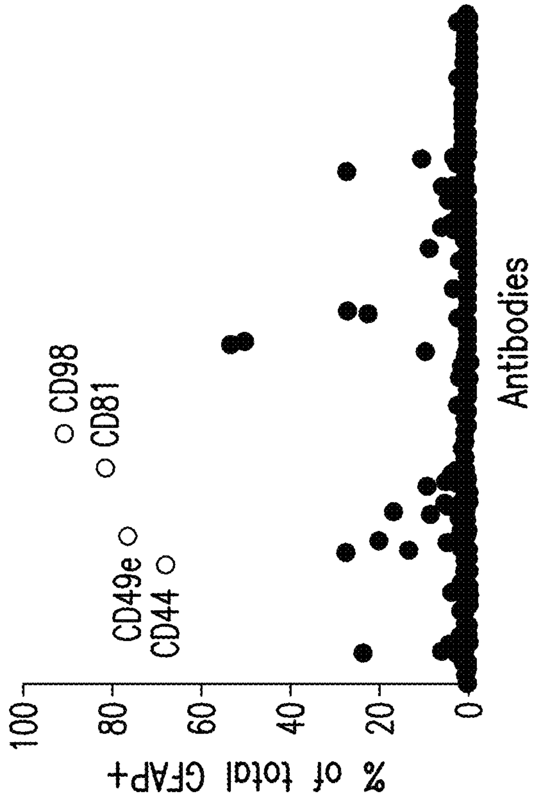
Figure 5C:
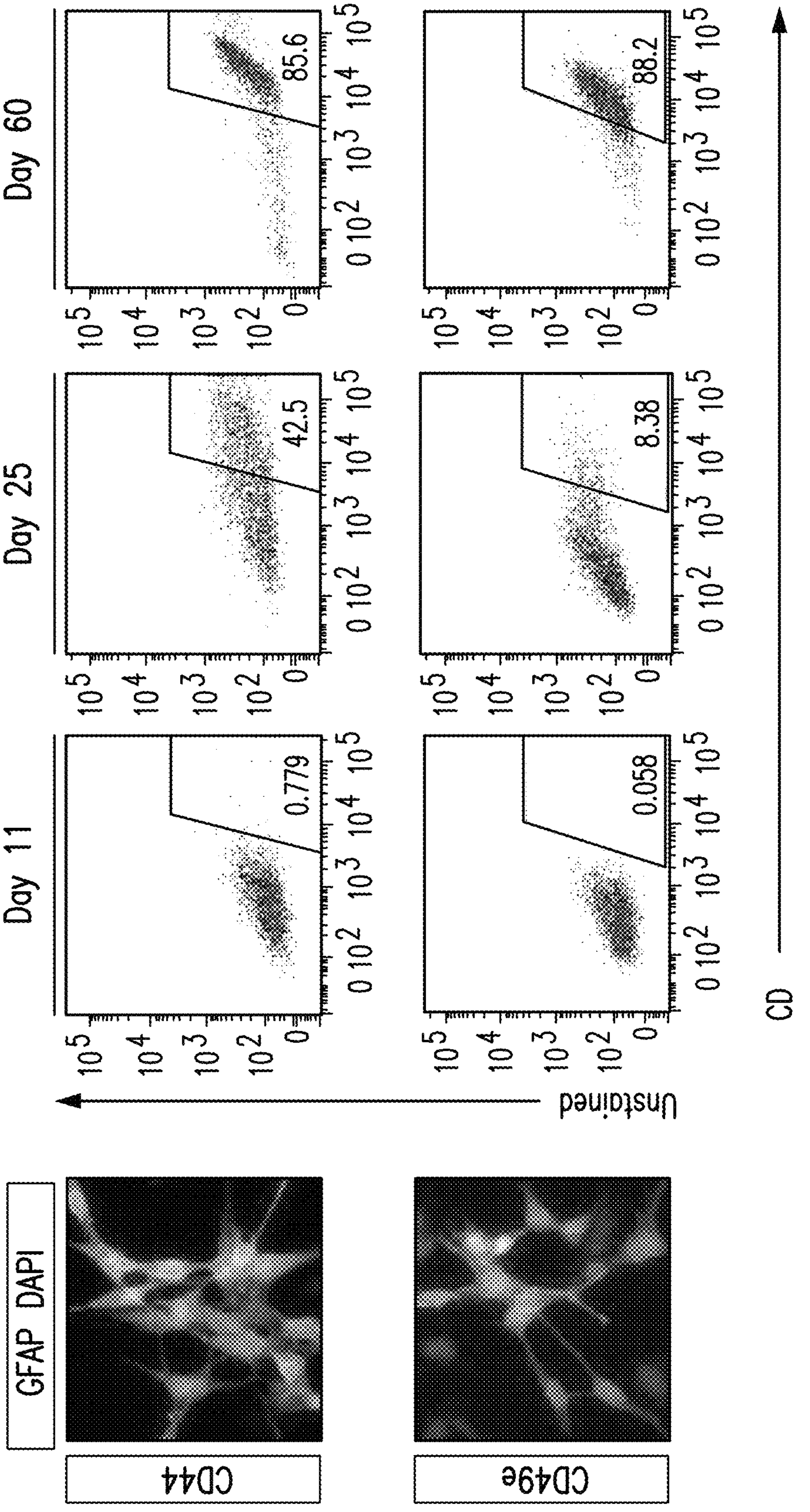
Figure 5C:
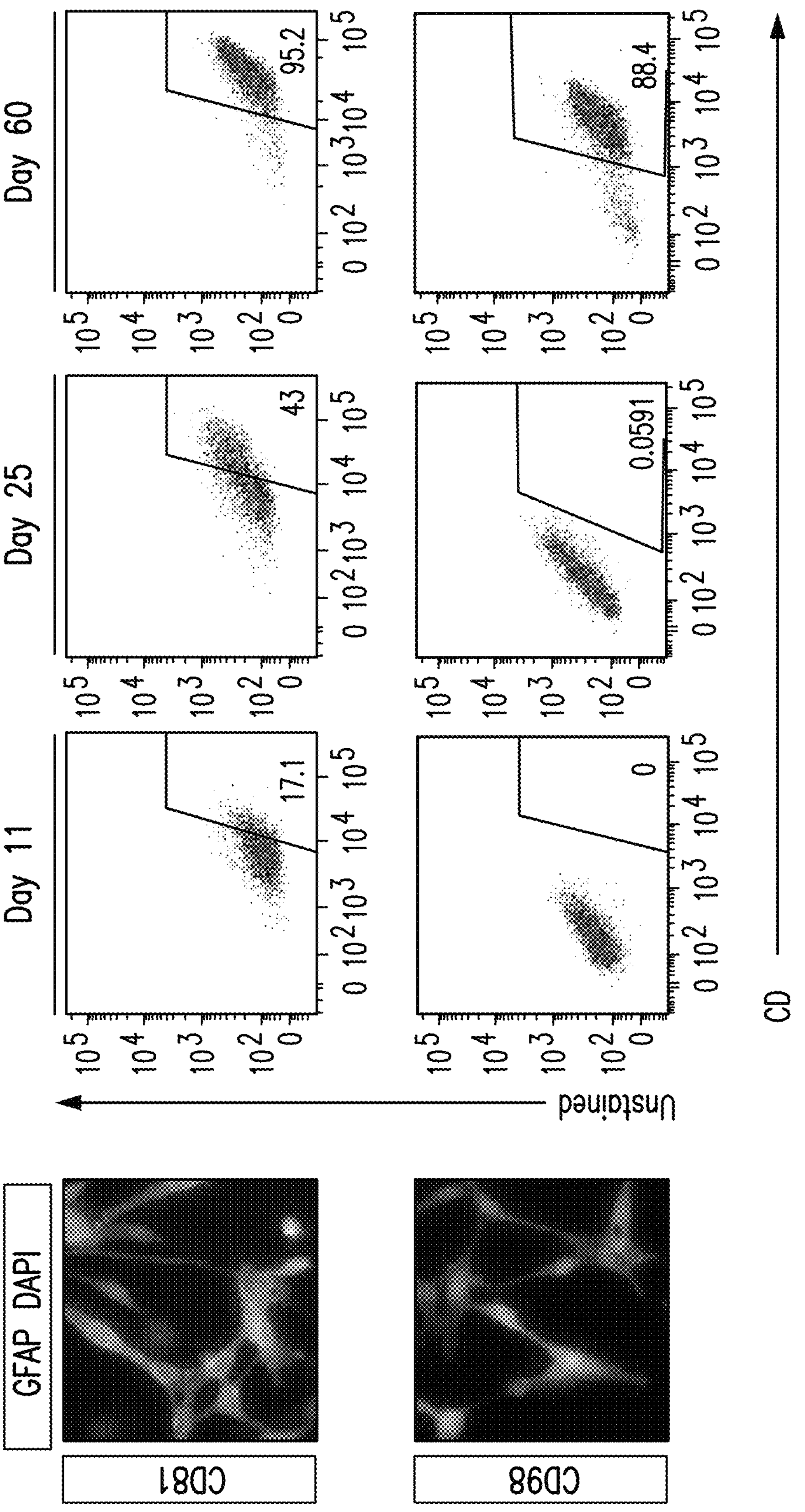

To enable the prospective isolation of hESC-SCs during the differentiation, the inventors screened a library of 242 antibodies for surface antigens that specifically mark $GFAP^+$ SCs (FIG. 5A). It was determined that CD44, CD49e, CD81 and CD98 label the $GFAP^+$ cell population (FIG. 5B). Further validations revealed that CD98 was the only marker specifically expressed in day 60 SCs but not in day 11 NC or day 25 SCP cells (FIG. 5C) which express CD49D, a marker previously shown to label early $SOX10^+$ NC lineages (Fattahi et al., 2016). RNA sequencing of purified cells demonstrated that day 25 hESC-derived SCPs were closely related to early NC cells while day 50 and, in particular, day 100 SCs showed a gene expression pattern closely matching primary adult human SCs (FIG. 1G). The gene expression data also yielded novel candidate SCP and SC markers by comparing day 25 and 100 cells with day 11 NC (FIG. 1H). A list of top 200 enriched transcripts for each lineage is provided in Tables 1-4.

hESC-SCs Promote Neuronal Maturation and Myelination In Vitro and Engraft into the Injured Rat Sciatic Nerve In Vivo A key function of glia is to interact with neurons to regulate their function and produce myelin. The inventors tested this ability in hESC-SCs by establishing co-cultures with hESC-derived sensory (Chambers et al., 2012) and motor neurons generated using previously reported methods (Calder et al., 2015) (FIG. 2 A). Day 60 RFP-labeled hESC-SCs were mixed with day 50 GFP-labeled hESC sensory neurons and monitored 72 hours after the initiation of co-cultures. The SCs associate closely and align with the neuronal fibers indicating that they have the required receptors to respond properly to the signaling cues expressed on the axon membrane (FIG. 2B).

The lengthy process of functional maturation in hESC-derived lineages is a major hurdle in current differentiation systems. Glial cells are shown to promote functional maturation of neurons in co-cultures of hESC-derived CNS lineages (Tang et al., 2013). To assess whether hESC-SCs can contribute to overcome this problem, their impact on functional maturation of motor neurons was investigated. The inventors set up a co-culture system with day 60 hESC-SCs and day 25 hESC-derived motor neurons. Similar to the co-cultures with sensory neurons, the hESC-SCs showed a robust tendency to align with the neuronal fibers (FIG. 2D). The protracted process of human cell maturation in hESC-derived lineages is a major hurdle in the field. Glial cells such as astrocytes have been shown to promote the functional maturation of hESC-derived CNS neurons (Tang et al., 2013). To monitor the functional maturation of co-cultured motor neurons, calcium imaging was performed at day 40 and 70 of motor neuron differentiation (15 and 55 days after the initiation of co-culture). The co-cultured hESC-derived motor neurons showed an ability to respond to glutamate and KC1 stimulation as early as day 40 while the motor neuron single cultures did not show such calcium responses at the same time point (FIG. 2E-left panel). The responsiveness of the co-cultured motor neurons to glutamate and KC1 stimulations was further increased at day 70 and was remarkably higher compared to motor neuron single cultures (FIG. 2E-right panel).

To assess whether hESC-derived SCs are capable of forming myelin, the inventors established long-term co-cultures of hESC-SCs with hESC-sensory neurons, and characteristic, myelinated structures were observed by transmission electron microscopy (TEM) (FIG. 2C). These finding validate the ability of hESC-SCs to produce myelin and modulate neuronal behavior in vitro. SCs are also known to play significant roles in promoting nerve repair in response to injury (Jessen and Mirsky, 2016; Jessen et al., 2015; Webber et al., 2011). This is largely due to their ability to secrete tropic factors that guide the repair process in the damaged axons (Arthur-Farraj et al., 2012; Bunge, 1994; Webber et al., 2011). Transplantation of SCs has been demonstrated to enhance nerve regeneration in several experimental systems such as spinal cord contusion models (Lavdas et al., 2008; Rodrigues et al., 2012; Wiliams and Bunge, 2012; Kocsis and Bunge, 2014); and autologous SCs are currently being tested in SCI patients (NCT01739023; NCT02354625). The main obstacle in such cell therapy approaches is the limitations in obtaining phenotypically stable primary SCs in large scale. hESCs offer a limitless alternative supply of human SCs for these regenerative applications. As a first step towards assessing the regenerative potential of hESC-SCs, the inventors tested whether these cells can survive and engraft after transplantation in a rat model of sciatic nerve injury.

Figure 3A:
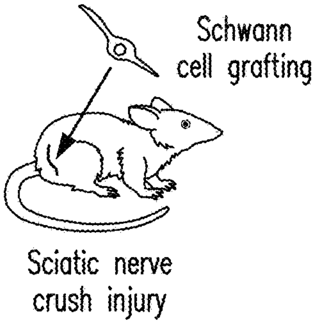
FIGS. 3A-3E: In vivo functional characterization of hESC-SCs.
Figure 3B:
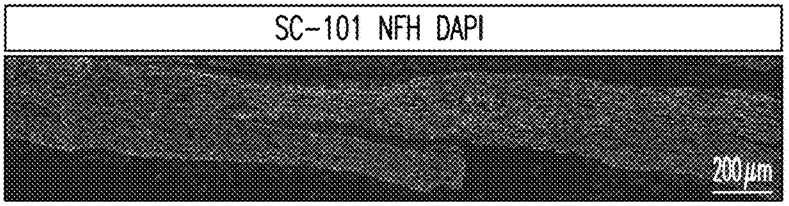
Figure 3C:
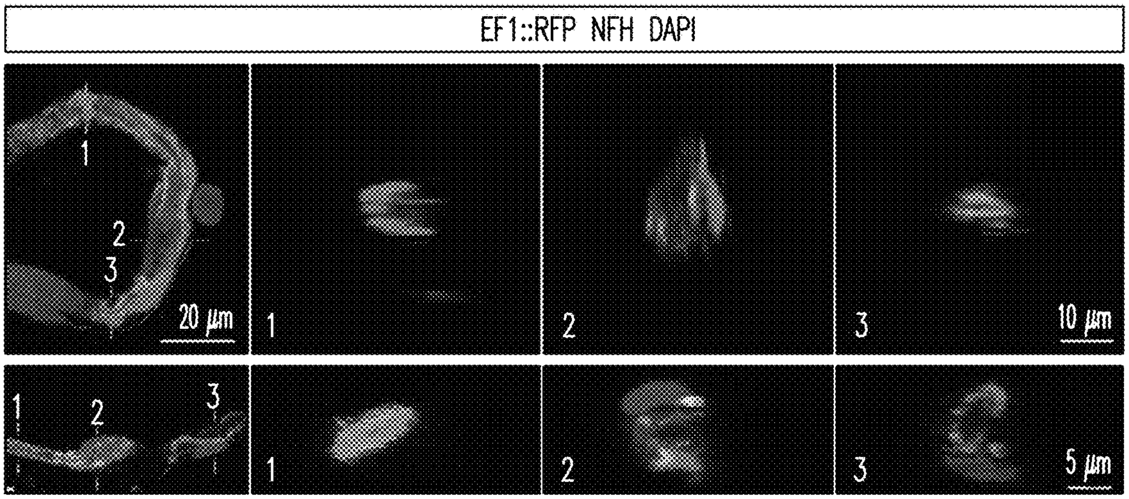
Figure 3D:
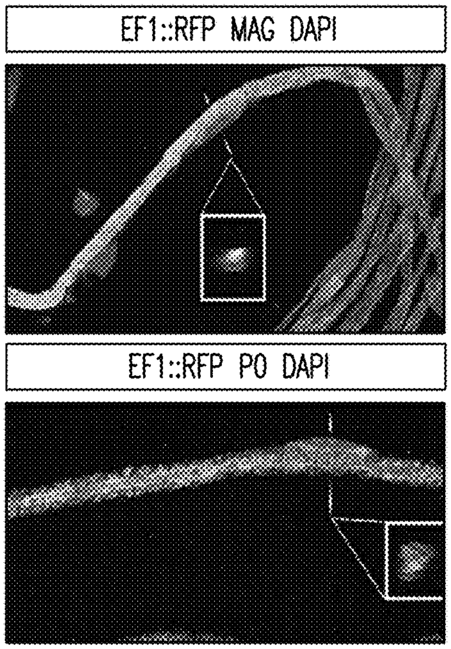
Figure 3E:
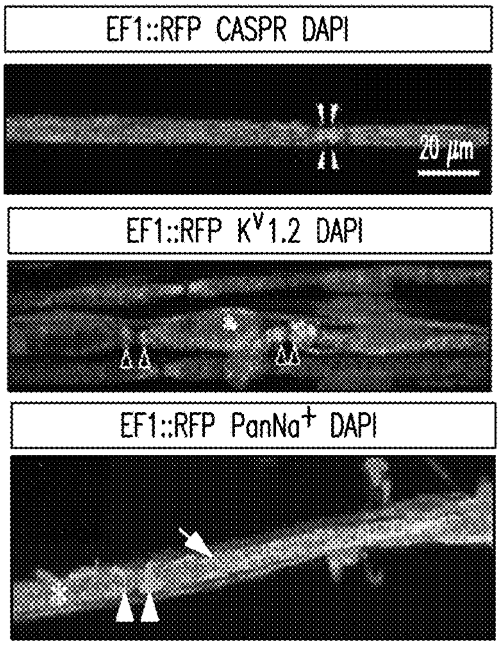

In this model, the sciatic nerve was mechanically crushed and the hESC-SCs were immediately injected in the site of injury (FIG. 3A). The transplanted hESC-SCs were readily detectable in transplanted nerves eight weeks after the injection by staining for human specific nuclear marker SC101 (FIG. 3B). The transplanted hESC-SCs were in close contact with the host neuronal fibers (FIG. 3C) and expressed myelin markers such as MAG and P0 (FIG. 3D). In a mature myelinated fiber, sodium channels are localized to the nodes of Ranvier. This area is flanked by a domain where the axon membrane is attached to the myelin membrane by a specific protein called CASPR. Next to the CASPR expressing region, there is a membrane domain that contains the potassium channels. The expression of these markers in axons that were wrapped in RFP-labelled hESC-SCs was evaluated and it was confirmed that they are localized in their appropriate membrane domains (FIG. 3E). These studies demonstrate the ability of hESC-SCs to engraft and produce myelin that is appropriately associated with nerve fibers and the nodes of Ranvier in injured adult peripheral nerves.

Taken together, these in vitro and in vivo studies on hPSC-SCs confirm their SC identity and function.

Discussion

SCs play important roles in peripheral nerve development, function and repair. However, their development and function are poorly understood in humans due to limitations in obtaining them in workable numbers from primary tissue. Others previously reported Schwann-like cells from hPSCs after long-term maintenance of P75+/HNK1+NC precursors (Lee et al., 2007), however, the these studies have the limitations of low induction efficiency, and months of in vitro culture, protracted differentiation, limited SC maturation and lack of myelination data (Lee et al., 2007; Liu et al., 2012; Ziegler et al., 2011). Attempts to derive human SCs by others also resulted in low yield, limited phenotypic characterization and lack of in vitro or in vivo myelination (Li et al., 2015; Mica et al., 2013). A highly efficient approach for generation of well characterized and pure population of human SCs was established, which sets the stage for future in depth developmental studies and translational applications such as disease modeling, and cell therapy.

An important feature of our hESC-based platform is the scalability and purity of the resulting SCs and the ability to culture cells for extended periods without losing SC properties. In contrast, primary SCs tend to rapidly lose their properties upon extended culture which results in the increasing contamination of Schwann cell cultures with fibroblast-like cells. Important developmental questions that are now accessible using this novel differentiation technology include the mechanisms controlling the transition from a multipotent NC stem cell to committed SCs and the study of human SC plasticity given recent data in the mouse suggesting that both melanocytes and parasympathetic neurons can be derived from early SC-lineages (Adameyko et al., 2009; Espinosa-Medina et al., 2014). The identification of CD98 as a surface marker for the prospective isolation of committed SCs represents a powerful tool for such studies. Based on the data presented here, studies on SC-mediated neuronal maturation and myelination should be other areas of focus. The modeling of PNS pathologies could be of particular interest. A surprising feature of the cultured hESC-derived Schwann cell is their gene expression pattern that not only confirms Schwann cell identity but suggests that pluripotent-derived cells match the expression pattern of adult Schwann cells. This is in contrast to most other in vitro derived hPSC-lineages such as neurons expressing fetal stage markers (Studer et al., 2015). Autologous SCs are currently being tested for applications in regenerative medicine targeting both PNS and CNS disorders (Lavdas et al., 2008; Rodrigues et al., 2012). The transplantation data demonstrate robust engraftment of hESC-SCs in a model of traumatic nerve injury. The results presented herein set a solid foundation for the application of hESC-SCs in regenerative medicine including spinal cord injury.

Access to scalable populations of SCs open up new avenues to investigate long standing questions in human SC development such as the transition from early neurogenic precursors into a committed gliogenic phase and further progression towards a myelinating cell stage. The hPSC-SCs can also be employed to determine the role of glia in regulation of neuronal function and maturation in the PNS. Poor neuronal maturation is a limitation of most current hPSC-based differentiation protocols. The SCs are also being utilized for various applications in regenerative medicine in the PNS and CNS (Lavdas et al., 2008; Rodrigues et al., 2012). Large scale production of human SCs and their ability to engraft in adult injured nerves establishes a foundation for their applications in regenerative medicine.

In conclusion, this study presents an effective framework to access human SC lineages for exploring their biology in health and disease and developing novel therapies for DPN. Directed differentiation of hPSCs represent an effective approach for large scale derivation of human SCs with broad implications in basic and translational research. This framework offers new possibilities for in-depth studies of the role of glia in the PNS biology and disease and contributes to the development of new therapeutics for peripheral neuropathies in future. This work should make human SC-based studies routine for applications in regenerative medicine and human disease modeling.

TABLE 1

Top 200 unregulated genes in hESC-derived Schwann cell precursors (day 25) versus hESC-derived NC (day 11).

| Gene ID | log2FoldChange |
|---|---|
| CALCB | 13.12 |
| GPR116 | 9.29 |
| TSPYL5 | 8.44 |
| ITPKA | 8.33 |
| SLC17A6 | 8.28 |
| SYPL2 | 8.12 |
| LOC100128252 | 7.73 |
| ANGPTL7 | 7.47 |
| LOC728978 | 7.31 |
| ZNF502 | 7.22 |
| ZNF229 | 7.17 |
| XLOC__003498 | 7.12 |

TABLE 1-continued

Top 200 unregulated genes in hESC-derived Schwann cell precursors (day 25) versus hESC-derived NC (day 11).

| Gene ID | log2FoldChange |
|---|---|
| STK32A | 7.08 |
| LOC100507341 | 7.01 |
| EEF1A2 | 6.98 |
| TRIM54 | 6.95 |
| SEZ6L | 6.77 |
| SLC16A6 | 6.66 |
| C20orf26 | 6.64 |
| LPL | 6.58 |
| STMN4 | 6.57 |
| CNGA3 | 6.55 |
| QPCT | 6.54 |
| C12orf69 | 6.42 |
| CACNG5 | 6.33 |
| BAAT | 6.30 |
| AGBL4 | 6.28 |
| COL12A1 | 6.22 |
| SPOCK2 | 6.21 |
| XLOC 000972 | 6.20 |
| ABCB1 | 6.18 |
| ANGPTL1 | 6.14 |
| CHRNA1 | 6.07 |
| DHRS2 | 6.06 |
| MFAP4 | 6.01 |
| ARHGDIG | 5.97 |
| XLOC 003411 | 5.97 |
| ABLIM3 | 5.97 |
| LINC00152 | 5.97 |
| HLA-DOB | 5.95 |
| P2RX3 | 5.93 |
| PLA2G4C | 5.87 |
| CAV1 | 5.86 |
| CD44 | 5.85 |
| FAM26E | 5.82 |
| SRPX2 | 5.81 |
| LUM | 5.80 |
| CRHBP | 5.74 |
| HOXD9 | 5.73 |
| ADAMTS8 | 5.71 |
| SLC30A2 | 5.66 |
| C7orf29 | 5.65 |
| DSCAM | 5.65 |
| PHOX2A | 5.63 |
| KCNK9 | 5.62 |
| GAL | 5.59 |
| SST | 5.58 |
| DMGDH | 5.53 |
| KCNH5 | 5.52 |
| TRIM67 | 5.52 |
| GPR64 | 5.50 |
| GPR115 | 5.49 |
| PTPRN | 5.48 |
| NKX6-2 | 5.48 |
| PNPLA4 | 5.48 |
| NOV | 5.47 |
| ABCG1 | 5.42 |
| NELL1 | 5.39 |
| SPARCL1 | 5.37 |
| LOC375010 | 5.37 |
| APLNR | 5.35 |
| DCN | 5.35 |
| SLC10A4 | 5.35 |
| NCAN | 5.33 |
| PLEK2 | 5.32 |
| HSPB7 | 5.32 |
| CLCA2 | 5.30 |
| FAIM2 | 5.29 |
| CALB1 | 5.28 |
| SLC6A15 | 5.26 |
| LOC100132891 | 5.24 |
| SCG2 | 5.23 |
| NFIB | 5.22 |
| RUNDC3B | 5.21 |
| XLOC 010607 | 5.21 |
| C5AR1 | 5.21 |
| MICAL2 | 5.20 |

TABLE 1-continued

Top 200 unregulated genes in hESC-derived Schwann cell precursors (day 25) versus hESC-derived NC (day 11).

| Gene ID | log2FoldChange |
|---|---|
| SGIP1 | 5.17 |
| GNG3 | 5.14 |
| LOC541471 | 5.14 |
| KCNA2 | 5.14 |
| FOXF2 | 5.11 |
| IFI44L | 5.10 |
| HPCAL4 | 5.10 |
| LOC100507043 | 5.09 |
| TNFAIP6 | 5.09 |
| TMEM132D | 5.07 |
| KLHDC7B | 5.04 |
| GMPR | 5.03 |
| CMKLR1 | 5.02 |
| PPP1R27 | 5.01 |
| REEP1 | 5.01 |
| PALM3 | 5.00 |
| PTPN5 | 4.99 |
| GPRIN3 | 4.99 |
| MGP | 4.97 |
| ATP8A2 | 4.97 |
| SERPINB2 | 4.95 |
| TCN1 | 4.94 |
| IFI44 | 4.94 |
| CLVS2 | 4.94 |
| DGKI | 4.93 |
| FAM20C | 4.91 |
| TPH2 | 4.91 |
| TGFA | 4.90 |
| ACTG2 | 4.89 |
| ULBP2 | 4.89 |
| RMRP | 4.89 |
| XLOC_011087 | 4.88 |
| NPFFR2 | 4.88 |
| GDAP1L1 | 4.86 |
| INHBA | 4.85 |
| CHSY3 | 4.85 |
| PPYR1 | 4.84 |
| CD163L1 | 4.83 |
| MIR7-3HG | 4.82 |
| ZNF542 | 4.79 |
| CDH13 | 4.78 |
| TM4SF1 | 4.77 |
| TYRP1 | 4.77 |
| SYT9 | 4.77 |
| CACNG7 | 4.76 |
| PDLIM3 | 4.76 |
| FAM135B | 4.74 |
| NETO1 | 4.74 |
| CD207 | 4.73 |
| TNC | 4.73 |
| TNFRSF8 | 4.73 |
| XLOC 013083 | 4.73 |
| SYT5 | 4.73 |
| PMP2 | 4.72 |
| PTPRH | 4.72 |
| ZFP28 | 4.71 |
| LHFPL4 | 4.70 |
| TTBK1 | 4.69 |
| HOXB7 | 4.68 |
| HCST | 4.67 |
| SERPINB7 | 4.67 |
| LOC653513 | 4.67 |
| MSC | 4.66 |
| SYNGR3 | 4.65 |
| POPDC3 | 4.65 |
| PENK | 4.62 |
| CFI | 4.59 |
| C3AR1 | 4.59 |
| SERPINE1 | 4.58 |
| NT5E | 4.57 |
| C4orf32 | 4.57 |
| TMEM59L | 4.56 |
| RIPPLY2 | 4.54 |
| STEAP3 | 4.54 |
| SLC1A2 | 4.54 |

TABLE 1-continued

Top 200 unregulated genes in hESC-derived Schwann cell precursors (day 25) versus hESC-derived NC (day 11).

| Gene ID | log2FoldChange |
|---|---|
| HECW1 | 4.54 |
| IL8 | 4.54 |
| FAM65B | 4.53 |
| TLR4 | 4.53 |
| ADAMTS5 | 4.52 |
| CDKN2B | 4.51 |
| LGI2 | 4.51 |
| KCNMA1 | 4.50 |
| ANKRD1 | 4.50 |
| XLOC 009257 | 4.50 |
| MXRA5 | 4.49 |
| HIGD1B | 4.49 |
| ALX4 | 4.47 |
| RUNX3 | 4.46 |
| ETV4 | 4.46 |
| HOXD8 | 4.45 |
| FLNC | 4.45 |
| HRK | 4.45 |
| HRH3 | 4.45 |
| LOC338651 | 4.45 |
| CAV2 | 4.44 |
| HCST | 4.67 |
| SERPINB7 | 4.67 |
| LOC653513 | 4.67 |
| MSC | 4.66 |
| SYNGR3 | 4.65 |
| POPDC3 | 4.65 |
| PENK | 4.62 |
| CFI | 4.59 |
| C3AR1 | 4.59 |
| SERPINE1 | 4.58 |
| NT5E | 4.57 |
| C4orf32 | 4.57 |
| TMEM59L | 4.56 |
| RIPPLY2 | 4.54 |
| STEAP3 | 4.54 |
| SLC1A2 | 4.54 |
| HECW1 | 4.54 |
| IL8 | 4.54 |
| FAM65B | 4.53 |
| TLR4 | 4.53 |
| ADAMTS5 | 4.52 |
| CDKN2B | 4.51 |
| LGI2 | 4.51 |
| KCNMA1 | 4.50 |
| ANKRD1 | 4.50 |
| XLOC_009257 | 4.50 |
| MXRA5 | 4.49 |
| HIGD1B | 4.49 |
| ALX4 | 4.47 |
| RUNX3 | 4.46 |
| ETV4 | 4.46 |
| HOXD8 | 4.45 |
| FLNC | 4.45 |
| HRK | 4.45 |
| HRH3 | 4.45 |
| LOC338651 | 4.45 |
| CAV2 | 4.44 |

TABLE 2

Top 200 unregulated genes in hESC-derived Schwann cells (day 50) versus hESC-derived NC (day 11)

| Gene ID | log2FoldChange |
|---|---|
| STT3B | 11.85 |
| CTAGE5 | 11.30 |
| KBTBD6 | 10.63 |
| B3GALTL | 10.46 |
| PAX9 | 10.07 |
| APOO | 9.45 |

TABLE 2-continued

Top 200 unregulated genes in hESC-derived Schwann cells (day 50) versus hESC-derived NC (day 11)

| Gene ID | log2FoldChange |
|---|---|
| XLOC 011326 | 9.15 |
| HSPE1 | 8.84 |
| TRIM3 | 8.73 |
| RAP2B | 8.53 |
| TRAPPC9 | 8.49 |
| TXNDC15 | 8.35 |
| THBS2 | 8.34 |
| GMPPB | 8.32 |
| PLP2 | 8.20 |
| NCS1 | 8.09 |
| ABL1 | 7.92 |
| FMNL2 | 7.77 |
| NDUFA12 | 7.39 |
| XLOC__009725 | 7.34 |
| PTRH2 | 7.24 |
| CNBD1 | 7.24 |
| XLOC 000576 | 7.21 |
| ZNF224 | 7.19 |
| PDXDC2P | 7.11 |
| GSTM3 | 7.07 |
| CENPM | 7.06 |
| GCLM | 7.04 |
| NCAPH | 6.98 |
| C15orf37 | 6.98 |
| JAK1 | 6.97 |
| STARD3 | 6.87 |
| TRIB3 | 6.80 |
| DOPEY2 | 6.77 |
| APAF1 | 6.72 |
| NCOA4 | 6.71 |
| PSMB6 | 6.68 |
| COX20 | 6.64 |
| PIK3CB | 6.63 |
| HAX1 | 6.58 |
| KITLG | 6.58 |
| CNTD1 | 6.54 |
| ETNK2 | 6.47 |
| LRRC57 | 6.47 |
| CDK2 | 6.43 |
| GOLGA7 | 6.42 |
| CCDC90B | 6.38 |
| GSTP1 | 6.31 |
| PPP1R8 | 6.28 |
| C7orf50 | 6.28 |
| POLR2L | 6.25 |
| ITGB1 | 6.24 |
| TYRP1 | 6.18 |
| DNAJC3 | 6.14 |
| THY1 | 6.14 |
| GOSR2 | 6.12 |
| FAM123B | 6.12 |
| HIGD1A | 6.10 |
| ELMOD3 | 6.10 |
| NME5 | 6.04 |
| TUSC2 | 6.02 |
| C11orf10 | 5.93 |
| SIPA1 | 5.93 |
| JUP | 5.92 |
| NCKAP5 | 5.90 |
| THYN1 | 5.90 |
| RUNX1 | 5.81 |
| FLJ46906 | 5.80 |
| XLOC__004725 | 5.77 |
| MGC57346 | 5.74 |
| RTP4 | 5.72 |
| PLD3 | 5.70 |
| NYAP1 | 5.69 |
| TLN2 | 5.65 |
| XLOC 009577 | 5.62 |
| FBLN5 | 5.57 |
| LRFN5 | 5.56 |
| CDH7 | 5.56 |
| XLOC__003471 | 5.54 |
| BRWD3 | 5.53 |
| RAX2 | 5.49 |

TABLE 2-continued

| Top 200 unregulated genes in hESC-derived Schwann cells (day 50) versus hESC-derived NC (day 11) | |
|---|---|
| Gene ID | log2FoldChange |
| MRPS16 | 5.38 |
| CUL4A | 5.36 |
| EPHA5 | 5.36 |
| SPTBN2 | 5.34 |
| SMYD5 | 5.31 |
| CDKN2AIP | 5.30 |
| ZNF829 | 5.28 |
| OLFM2 | 5.27 |
| PNMA6C | 5.24 |
| DNAJB11 | 5.23 |
| NIPAL2 | 5.20 |
| ZNF622 | 5.19 |
| STRADA | 5.18 |
| CEP57L1 | 5.17 |
| SHISA6 | 5.16 |
| CKAP2 | 5.15 |
| IGFBP7 | 5.14 |
| GRSF1 | 5.14 |
| GRWD1 | 5.13 |
| CD101 | 5.13 |
| PLIN2 | 5.08 |
| LOC100129361 | 5.04 |
| PRKG1 | 5.04 |
| SERF2 | 5.04 |
| RUNX3 | 5.04 |
| FAM91A1 | 5.02 |
| ALDH3B1 | 5.01 |
| CCDC96 | 5.00 |
| NNMT | 4.98 |
| C11orf71 | 4.98 |
| ZNF804A | 4.98 |
| DNAJA1 | 4.94 |
| CHCHD1 | 4.93 |
| SRPX | 4.91 |
| XLOC 007995 | 4.89 |
| C11orf61 | 4.87 |
| TNFAIP8 | 4.86 |
| CSPG4 | 4.86 |
| ALX3 | 4.86 |
| SSR4P1 | 4.85 |
| CES4A | 4.84 |
| IFI44 | 4.84 |
| PLCD3 | 4.84 |
| XLOC 009509 | 4.83 |
| PPP2R5E | 4.82 |
| C19orf53 | 4.81 |
| SPARCL1 | 4.79 |
| UBE3B | 4.78 |
| HPGD | 4.77 |
| ADM2 | 4.74 |
| TLR1 | 4.73 |
| NYNRIN | 4.73 |
| PHF8 | 4.73 |
| IL2RB | 4.72 |
| TEX9 | 4.72 |
| IGFBP1 | 4.71 |
| PLAC8L1 | 4.69 |
| DHX34 | 4.68 |
| TOPBP1 | 4.67 |
| BCAP31 | 4.67 |
| RHBDF2 | 4.66 |
| IP53BP2 | 4.65 |
| DIRAS2 | 4.63 |
| DNMT1 | 4.63 |
| TMEM9B | 4.63 |
| OSGIN1 | 4.63 |
| SWI5 | 4.63 |
| CILP | 4.61 |
| GLTPD2 | 4.60 |
| LSMD1 | 4.58 |
| SAMD11 | 4.58 |
| BCAR1 | 4.58 |
| ENTHD1 | 4.57 |
| PTTG1IP | 4.54 |
| PAFAH1B1 | 4.53 |

TABLE 2-continued

| Top 200 unregulated genes in hESC-derived Schwann cells (day 50) versus hESC-derived NC (day 11) | |
|---|---|
| Gene ID | log2FoldChange |
| SERPINB1 | 4.50 |
| BPI | 4.49 |
| GNL3 | 4.48 |
| APOE | 4.48 |
| DR1 | 4.47 |
| TUBGCP3 | 4.47 |
| C11orf82 | 4.47 |
| ANTXR1 | 4.45 |
| DLG5 | 4.44 |
| PLK1S1 | 4.41 |
| EGLN2 | 4.40 |
| GTF2A1 | 4.40 |
| COL6A2 | 4.40 |
| CAPZA1 | 4.39 |
| PRR24 | 4.38 |
| SMUG1 | 4.36 |
| ZNF626 | 4.36 |
| MAGED2 | 4.36 |
| EHBP1 | 4.35 |
| LAMA5 | 4.35 |
| XLOC 008024 | 4.34 |
| RPS10 | 4.33 |
| THTPA | 4.33 |
| PHF2 | 4.32 |
| CCDC71L | 4.31 |
| KLHL18 | 4.30 |
| FAM49A | 4.29 |
| TIMP4 | 4.29 |
| ANAPC10 | 4.28 |
| C19orf29-AS1 | 4.28 |
| SKIV2L2 | 4.27 |
| C15orf52 | 4.26 |
| ATP6AP2 | 4.25 |
| FASTKD5 | 4.25 |
| WDR45 | 4.24 |
| AP2S1 | 4.24 |
| HS2ST1 | 4.23 |
| G6PC3 | 4.21 |
| ANKRD44 | 4.17 |
| GIT2 | 4.16 |
| MIR22HG | 4.16 |
| SH3TC2 | 4.15 |
| ALPK1 | 4.15 |
| POLE | 4.14 |

TABLE 3

| Top 200 upregulated genes in hESC-derived Schwann cells (day 100) versus hESC-derived NC (day 11) | |
|---|---|
| Gene ID | Log2FoldChange |
| TYRP1 | 15.79 |
| CD44 | 13.21 |
| ENTHD1 | 11.71 |
| NT5E | 11.69 |
| HTR2B | 11.48 |
| NOV | 10.78 |
| IL8 | 10.49 |
| SLC16A6 | 10.35 |
| CDKN2A | 9.92 |
| GPNMB | 9.90 |
| HSPB7 | 9.46 |
| EMP1 | 9.29 |
| RIT2 | 9.29 |
| PAEP | 9.16 |
| TYR | 8.99 |
| SYNC | 8.98 |
| XLOC_008700 | 8.83 |
| NLRC5 | 8.71 |
| FAIM3 | 8.68 |
| RGS20 | 8.64 |

TABLE 3-continued

| Top 200 upregulated genes in hESC-derived Schwann cells (day 100) versus hESC-derived NC (day 11) | |
|---|---|
| Gene ID | Log2FoldChange |
| CBR3 | 8.63 |
| TMEM173 | 8.63 |
| GJA3 | 8.59 |
| SAMD9 | 8.33 |
| EVI2B | 8.30 |
| FBXO32 | 8.26 |
| TSPYL5 | 8.25 |
| TLR4 | 8.09 |
| SERPINE1 | 7.90 |
| HOXD-AS1 | 7.88 |
| CITED1 | 7.87 |
| KCNA5 | 7.81 |
| ATP10A | 7.75 |
| OCA2 | 7.75 |
| IRF4 | 7.73 |
| MMP8 | 7.71 |
| GAL | 7.70 |
| CD109 | 7.68 |
| LGI3 | 7.57 |
| LGALS3 | 7.53 |
| TRIM63 | 7.51 |
| XLOC 003498 | 7.46 |
| LOC285000 | 7.45 |
| KLHL38 | 7.39 |
| HOXB2 | 7.35 |
| PTHLH | 7.30 |
| MBP | 7.29 |
| CARD16 | 7.27 |
| TFF3 | 7.23 |
| IL13RA2 | 7.22 |
| LINC00152 | 7.21 |
| ISM1 | 7.21 |
| MLPH | 7.16 |
| ECM1 | 7.12 |
| CHSY3 | 7.11 |
| CXCL1 | 7.08 |
| KLF2 | 7.08 |
| ASB11 | 7.07 |
| KRTAP19-1 | 7.02 |
| C10orf90 | 7.01 |
| ITGA3 | 6.99 |
| LOC646329 | 6.98 |
| THBD | 6.96 |
| FLJ43663 | 6.95 |
| HR | 6.92 |
| C1orf127 | 6.89 |
| NFIX | 6.88 |
| LY96 | 6.85 |
| LOC100128252 | 6.85 |
| TRIM47 | 6.79 |
| XLOC__002736 | 6.77 |
| COL8A1 | 6.76 |
| RUNX3 | 6.74 |
| ZNF229 | 6.72 |
| C15orf52 | 6.71 |
| CABLES1 | 6.69 |
| FOSL1 | 6.67 |
| RASGRP3 | 6.64 |
| TBX18 | 6.63 |
| SPON2 | 6.58 |
| THBS2 | 6.58 |
| LOC541471 | 6.53 |
| AHRR | 6.52 |
| SGCD | 6.50 |
| ZNF502 | 6.47 |
| CSPG4 | 6.45 |
| BARX2 | 6.44 |
| MYC | 6.44 |
| SLC7A4 | 6.43 |
| MLIP | 6.43 |
| VGF | 6.42 |
| DHRS2 | 6.41 |
| HOXD3 | 6.41 |
| SYPL2 | 6.39 |
| SGK1 | 6.39 |

TABLE 3-continued

| Top 200 upregulated genes in hESC-derived Schwann cells (day 100) versus hESC-derived NC (day 11) | |
|---|---|
| Gene ID | Log2FoldChange |
| MLANA | 6.39 |
| DUSP10 | 6.35 |
| ITGB3 | 6.35 |
| KCNJ13 | 6.32 |
| ST8SIA6 | 6.32 |
| MME | 6.32 |
| PLXNC1 | 6.32 |
| SUSD5 | 6.26 |
| DLX1 | 6.26 |
| MMP1 | 6.22 |
| ANO4 | 6.21 |
| C19orf71 | 6.20 |
| STK32A | 6.19 |
| CAV1 | 6.16 |
| PSMB8 | 6.12 |
| PLP2 | 6.12 |
| BCL2A1 | 6.11 |
| HOXD4 | 6.11 |
| LOC100507463 | 6.10 |
| TFPI2 | 6.07 |
| NFIB | 6.06 |
| TNFRSF14 | 6.05 |
| ANKRD1 | 6.03 |
| IFI16 | 6.01 |
| DDIT4L | 6.01 |
| KCNQ5 | 6.01 |
| NR4A3 | 6.00 |
| IFIT2 | 6.00 |
| XLOC__013026 | 6.00 |
| SH2D4B | 5.99 |
| XLOC__001215 | 5.98 |
| FAM129A | 5.96 |
| GREM1 | 5.96 |
| HSPA6 | 5.92 |
| TM4SF1 | 5.92 |
| HOXB7 | 5.92 |
| MET | 5.91 |
| MFSD12 | 5.90 |
| IL6R | 5.89 |
| RUNX1 | 5.86 |
| CATSPER1 | 5.83 |
| FAM20C | 5.83 |
| GMPR | 5.82 |
| GOLGA7B | 5.80 |
| PHLDA2 | 5.80 |
| MIR612 | 5.77 |
| GALNTL6 | 5.77 |
| MGAT5B | 5.76 |
| HSF4 | 5.75 |
| SLC1A4 | 5.74 |
| CD97 | 5.74 |
| SLC24A5 | 5.74 |
| XLOC 004803 | 5.74 |
| LOC375010 | 5.73 |
| COL12A1 | 5.68 |
| PNPLA4 | 5.66 |
| LOC100133445 | 5.66 |
| TSPAN10 | 5.64 |
| OSGIN1 | 5.63 |
| GIPC3 | 5.62 |
| CPNE7 | 5.59 |
| OAS3 | 5.59 |
| GRIN2B | 5.59 |
| CD300LB | 5.59 |
| KDR | 5.58 |
| UPP1 | 5.58 |
| S100A6 | 5.58 |
| SH3TC2 | 5.55 |
| WFDC1 | 5.54 |
| AQP9 | 5.53 |
| XLOC__001738 | 5.52 |
| XLOC 007040 | 5.51 |
| LYL1 | 5.51 |
| SLC6A15 | 5.49 |
| SYK | 5.49 |

TABLE 3-continued

| Top 200 upregulated genes in hESC-derived Schwann cells (day 100) versus hESC-derived NC (day 11) | |
|---|---|
| Gene ID | Log2FoldChange |
| C7orf29 | 5.46 |
| XLOC 009274 | 5.45 |
| RIPK3 | 5.45 |
| S100A4 | 5.41 |
| NFATC2 | 5.40 |
| CEBPE | 5.39 |
| GEM | 5.37 |
| MYOT | 5.37 |
| ABCG2 | 5.37 |
| XLOC__007085 | 5.35 |
| ERG | 5.33 |
| ARID5B | 5.32 |
| TRPV2 | 5.31 |
| LPL | 5.31 |
| XLOC__008985 | 5.31 |
| SERPINB2 | 5.31 |
| IFI35 | 5.27 |
| MIR221 | 5.27 |
| S100A2 | 5.27 |
| BMPR1B | 5.25 |
| SP100 | 5.24 |
| LOC400643 | 5.24 |
| PDGFB | 5.24 |
| XLOC 001228 | 5.20 |
| HRK | 5.20 |
| BHLHE41 | 5.19 |
| LDHAL6B | 5.18 |
| GPR65 | 5.17 |
| XLOC__006252 | 5.16 |
| LGALS1 | 5.13 |
| XLOC 008985 | 5.31 |
| LGALS1 | 5.13 |

TABLE 4

| Top 200 unregulated genes in human primary Schwann cells versus hESC-derived NC (day 11) | |
|---|---|
| Gene ID | log2FoldChange |
| KBTBD6 | 12.13 |
| FAHD2B | 11.98 |
| CTAGE5 | 11.64 |
| C19orf45 | 11.30 |
| XLOC 003345 | 10.85 |
| WDR90 | 10.83 |
| B3GALTL | 10.55 |
| PAX9 | 9.77 |
| GMPPB | 9.65 |
| HSPE1 | 9.64 |
| XLOC__008617 | 9.53 |
| TRIM3 | 9.32 |
| SPINT2 | 9.08 |
| PLP2 | 9.05 |
| ADAMTS20 | 8.91 |
| CD8A | 8.84 |
| COX20 | 8.84 |
| UNC5CL | 8.75 |
| DIRAS2 | 8.45 |
| THBS2 | 8.41 |
| RIMS3 | 8.20 |
| ZNF273 | 8.20 |
| GCLM | 8.20 |
| CLDN3 | 8.16 |
| CCDC167 | 8.15 |
| RAP2A | 8.10 |
| NCS1 | 8.10 |
| TXNDC15 | 8.08 |
| DSN1 | 8.01 |
| ZNF224 | 7.97 |
| NYAP1 | 7.96 |
| SIPA1 | 7.90 |

TABLE 4-continued

| Top 200 unregulated genes in human primary Schwann cells versus hESC-derived NC (day 11) | |
|---|---|
| Gene ID | log2FoldChange |
| XLOC 009279 | 7.88 |
| JAK1 | 7.83 |
| NDUFA12 | 7.73 |
| XLOC 009509 | 7.70 |
| EFNB3 | 7.69 |
| SHISA6 | 7.66 |
| XLOC__000734 | 7.45 |
| APAF1 | 7.45 |
| HAX1 | 7.42 |
| PTRH2 | 7.41 |
| TLN2 | 7.40 |
| KLF12 | 7.38 |
| STT3B | 7.33 |
| MESP2 | 7.31 |
| RASGRP3 | 7.25 |
| ZNF559 | 7.25 |
| PRR11 | 7.24 |
| FAM123B | 7.22 |
| MBD1 | 7.18 |
| CNTN2 | 7.18 |
| LRFN5 | 7.16 |
| WBP4 | 7.12 |
| CLCN5 | 7.08 |
| ABL1 | 7.05 |
| ORC6 | 7.04 |
| CCL27 | 7.02 |
| KAT7 | 6.96 |
| KITLG | 6.95 |
| MIR4746 | 6.92 |
| ARHGEF38 | 6.92 |
| CCDC90B | 6.90 |
| MIR3176 | 6.89 |
| PPP1R8 | 6.88 |
| MCMBP | 6.84 |
| FAM199X | 6.81 |
| TRIB3 | 6.78 |
| GNL3 | 6.77 |
| BRWD3 | 6.77 |
| IRX2 | 6.76 |
| SPTBN2 | 6.75 |
| CTTNBP2 | 6.74 |
| KIAA1609 | 6.74 |
| ZC3H12B | 6.72 |
| TEX9 | 6.70 |
| THYN1 | 6.68 |
| DCC | 6.66 |
| UG0898H09 | 6.64 |
| STARD3 | 6.61 |
| ZNF804A | 6.61 |
| C11orf71 | 6.60 |
| ITGB1 | 6.57 |
| FLNB | 6.54 |
| NCOA4 | 6.53 |
| INMT | 6.51 |
| CBY3 | 6.51 |
| TAGLN3 | 6.50 |
| ST6GALNAC3 | 6.48 |
| POLR2L | 6.47 |
| XLOC 007995 | 6.43 |
| MAGEE1 | 6.40 |
| LOC400604 | 6.39 |
| GOSR2 | 6.39 |
| LOC285889 | 6.39 |
| MGC57346 | 6.37 |
| TIMP4 | 6.27 |
| CNKSR1 | 6.26 |
| GOLGA7 | 6.26 |
| GLTPD2 | 6.24 |
| XLOC__009224 | 6.23 |
| PSMB6 | 6.22 |
| RTDR1 | 6.18 |
| MTL5 | 6.17 |
| IGLON5 | 6.17 |
| HIGD1A | 6.16 |
| PBK | 6.15 |

TABLE 4-continued

| Top 200 unregulated genes in human primary Schwann cells versus hESC-derived NC (day 11) | |
|---|---|
| Gene ID | log2FoldChange |
| SPATA5L1 | 6.14 |
| XLOC__014081 | 6.14 |
| CUL4A | 6.13 |
| MCM5 | 6.10 |
| SMYD5 | 6.10 |
| LIN28A | 6.06 |
| ANTXR2 | 6.04 |
| LRRC57 | 6.03 |
| RUNX1 | 6.02 |
| XLOC 006828 | 6.01 |
| FAM66C | 5.99 |
| RAX2 | 5.99 |
| ERMN | 5.98 |
| RLBP1 | 5.95 |
| TP73 | 5.93 |
| PPOX | 5.88 |
| BRD9 | 5.88 |
| TTC40 | 5.87 |
| BCL7A | 5.83 |
| PAEP | 5.83 |
| SWI5 | 5.81 |
| SPTBN4 | 5.80 |
| DNAJC3 | 5.79 |
| MACROD2 | 5.79 |
| FBLN5 | 5.78 |
| ALX3 | 5.78 |
| LAMA5 | 5.77 |
| RBM28 | 5.77 |
| GRWD1 | 5.74 |
| XLOC__012069 | 5.71 |
| LOC339874 | 5.70 |
| AGAP8 | 5.70 |
| NIPAL2 | 5.70 |
| NNMT | 5.69 |
| EPHA5 | 5.67 |
| CNTNAP3B | 5.67 |
| XLOC__010236 | 5.64 |
| EHBP1 | 5.64 |
| PLAC8L1 | 5.64 |
| GPR162 | 5.63 |
| MYEF2 | 5.63 |
| CAPZA1 | 5.60 |
| DIRC3 | 5.60 |
| RHBDF2 | 5.59 |
| ZNF610 | 5.59 |
| XLOC__011568 | 5.58 |
| GRHL3 | 5.58 |
| SETDB2 | 5.56 |
| UBE3B | 5.55 |
| CD97 | 5.54 |
| XLOC__012905 | 5.54 |
| XLOC 011507 | 5.54 |
| MOB3B | 5.53 |
| NRARP | 5.53 |
| SRPX | 5.51 |
| LOC100506314 | 5.51 |
| ZNF497 | 5.50 |
| CALM2 | 5.49 |
| XLOC 003249 | 5.49 |
| PCSK9 | 5.48 |
| CSPG4 | 5.48 |
| XLOC 013922 | 5.47 |
| C12orf76 | 5.45 |
| CTAGE10P | 5.45 |
| ZNF622 | 5.44 |
| XLOC__012288 | 5.44 |
| LSMD1 | 5.41 |
| XLOC__003726 | 5.39 |
| ATRNL1 | 5.37 |
| XLOC__007094 | 5.37 |
| LOC100287036 | 5.34 |
| ELMOD3 | 5.34 |
| PLCD3 | 5.34 |
| THY1 | 5.33 |
| KCNH8 | 5.33 |

TABLE 4-continued

| Top 200 unregulated genes in human primary Schwann cells versus hESC-derived NC (day 11) | |
|---|---|
| Gene ID | log2FoldChange |
| XLOC 003433 | 5.33 |
| XLOC__011075 | 5.33 |
| MYEF2 | 5.63 |
| C15orf52 | 5.33 |
| ROBO2 | 5.31 |
| SDK1 | 5.31 |
| TSNARE1 | 5.31 |
| MTRR | 5.30 |
| SDR9C7 | 5.29 |
| GSTM3 | 5.29 |
| ZNF829 | 5.29 |
| IFI44 | 5.28 |
| IRAK3 | 5.28 |
| CHCHD1 | 5.27 |
| LOC100506801 | 5.27 |
| COG1 | 5.25 |
| TMEM200C | 5.25 |
| TBRG1 | 5.24 |
| PPFIA1 | 5.23 |

TABLE 5

| List of primary antibodies and working dilutions | | |
|---|---|---|
| Antibody | Source | Dilution |
| CD49D | Biolegend | 1:800 |
| TUJ1 | Covance | 1:1000 |
| CHAT | Millipore | 1:1000 |
| GFAP | Dako | 1:1000 |
| S100B | Dako | 1:200 |
| MBP | Millipore | 1:200 |
| MAG | Millipore | 1:200 |
| NFH | Encore | 1:1000 |
| PanNa | Joel Black | 1:1000 |
| Kv1.2 | Joel Black | 1:200 |
| CASPR | Joel Black | 1:1000 |
| SC101 | STEM Cell Tech | 1:1000 |
| Antibody | Source | Dilution |

REFERENCES

Arthur-Farraj, P. J., Latouche, M., Wilton, D. K., Quintes, S., Chabrol, E., Banerjee, A., Woodhoo, A., Jenkins, B., Rahman, M., Turmaine, M., et al. (2012). c-Jun reprograms Schwann cells of injured nerves to generate a repair cell essential for regeneration. Neuron 75, 633-647.

Adameyko, I., Lallemend, F., Aquino, J. B., Pereira, J. A., Topilko, P., Muller, T., Fritz, N., Beljajeva, A., Mochii, M., Liste, I., et al. (2009). Schwann cell precursors from nerve innervation are a cellular origin of melanocytes in skin. Cell 139, 366-379.

Bajpai, R., Chen, D. A., Rada-Iglesias, A., Zhang, J., Xiong, Y., Helms, J., Chang, C. P., Zhao, Y., Swigut, T., and Wysocka, J. (2010). CHD7 cooperates with PBAF to control multipotent neural crest formation. Nature 463, 958-962.

Barreto-Chang, O. L., and Dolmetsch, R. E. (2009). Calcium imaging of cortical neurons using Fura-2 AM. Journal of visualized experiments: JoVE.

Bunge, R. P. (1994). The role of the Schwann cell in trophic support and regeneration. J. Neurol. 242, S19-21.

Cai, S., Han, L., Ao, Q., Chan, Y.-S., and Shum, D.K.-Y. (2016). Human Induced Pluripotent Cell-Derived Sensory Neurons for Fate Commitment of Bone Marrow-Derived Schwann Cells: Implications for Remyelination Therapy. Stem Cells Transl. Med. sctm.2015-0424.
Calder, E. L., Tchieu, J., Steinbeck, J. A., Tu, E., Keros, S., Ying, S.-W., Jaiswal, M. K., Cornacchia, D., Goldstein, P. A., Tabar, V., et al. (2015). Retinoic Acid-Mediated Regulation of GLI3 Enables Efficient Motoneuron Derivation from Human ESCs in the Absence of Extrinsic SHH Activation. J. Neurosci. Off. J. Soc. Neurosci. 35, 11462-11481.
Callaghan, B. C., Cheng, H. T., Stables, C. L., Smith, A. L., and Feldman, E. L. (2012). Diabetic neuropathy: clinical manifestations and current treatments. Lancet Neurol. 11, 521-534.
Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nat. Biotechnol. 27, 275-280.
Chambers, S. M., Qi, Y., Mica, Y., Lee, G., Zhang, X.-J., Niu, L., Bilsland, J., Cao, L., Stevens, E., Whiting, P., et al. (2012). Combined small-molecule inhibition accelerates developmental timing and converts human pluripotent stem cells into nociceptors. Nat. Biotechnol. 30, 715-720.
Eckersley, L. (2002). Role of the Schwann cell in diabetic neuropathy. Int. Rev. Neurobiol. 50, 293-321
Espinosa-Medina, I., Outin, E., Picard, C. A., Chettouh, Z., Dymecki, S., Consalez, G. G., Coppola, E., and Brunet, J. F. (2014). Neurodevelopment. Parasympathetic ganglia derive from Schwann cell precursors. Science (New York, NY) 345, 87-90.
Fattahi, F., Steinbeck, J. A., Kriks, S., Tchieu, J., Zimmer, B., Kishinevsky, S., Zeltner, N., Mica, Y., El-Nachef, W., Zhao, H., et al. (2016). Deriving human ENS lineages for cell therapy and drug discovery in Hirschsprung disease. Nature 531, 105-109.
Finzsch, M., Schreiner, S., Kichko, T., Reeh, P., Tamm, E. R., Bosl, M. R., Meijer, D., and Wegner, M. (2010). Sox10 is required for Schwann cell identity and progression beyond the immature Schwann cell stage. The Journal of cell biology 189, 701-712.
Gordois, A., Scuffham, P., Shearer, A., Oglesby, A., and Tobian, J. A. (2003). The health care costs of diabetic peripheral neuropathy in the US. Diabetes care 26, 1790-1795.
Grewal, A. S., Bhardwaj, S., Pandita, D., Lather, V., and Sekhon, B. S. (2016). Updates on Aldose Reductase Inhibitors for Management of Diabetic Complications and Non-diabetic Diseases. Mini Rev. Med. Chem. 16, 120-162.
Guest, J., Santamaria, A. J., and Benavides, F. D. (2013). Clinical translation of autologous Schwann cell transplantation for the treatment of spinal cord injury. Curr. Opin. Organ Transplant. 18, 682-689.
Jessen, K. R., and Mirsky, R. (2016). The repair Schwann cell and its function in regenerating nerves. J. Physiol. 594, 3521-3531.
Jessen, K. R., Mirsky, R., and Lloyd, A. C. (2015). Schwann Cells: Development and Role in Nerve Repair. Cold Spring Harb. Perspect. Biol. 7, a020487.
Kocsis, J. D., and Bunge, M. B. (2014). Transplantationof Schwann cells and olfactory ensheathing cells as a therapeutic strategy in spinal cord injury. In Textbook of Neural Repair and Rehabilitation: M. Selzer, S. Clarke, L. Cohen, G. Kwakkel, and R. Miller, eds. (Cambridge: Cambridge University Press).
Kocsis, J. D., and Waxman, S. G. (2007). Schwann cells and their precursors for repair of central nervous system myelin. Brain 130, 1978-1980.
La Fontaine, J., Bhavan, K., Talal, T. K., and Lavery, L. A. (2014). Current concepts in the surgical management of acute diabetic foot infections. Foot Edinb. Scotl. 24, 123-127.
Lavdas, A. A., Papastefanaki, F., Thomaidou, D., and Matsas, R. (2008). Schwann cell transplantation for CNS repair. Curr. Med. Chem. 15, 151-160.
Lee, G., Kim, H., Elkabetz, Y., Al Shamy, G., Panagiotakos, G., Barberi, T., Tabar, V., and Studer, L. (2007). Isolation and directed differentiation of neural crest stem cells derived from human embryonic stem cells. Nat. Biotechnol. 25, 1468-1475.
Li, R., Liu Huawei, null, Yan, R., and Hu, M. (2015). [RESEARCH ADVANCE OF DIFFERENTIATION OF INDUCED PLURIPOTENT STEM CELLS INTO Schwann CELLS IN VITRO]. Zhongguo Xiu Fu Chong Jian Wai Ke Za Zhi Zhongguo Xiufu Chongjian Waike Zazhi Chin. J. Reparative Reconstr. Surg. 29, 1560-1563.
Liu, Q., Spusta, S. C., Mi, R., Lassiter, R. N., Stark, M. R., Hoke, A., Rao, M. S., and Zeng, X. (2012). Human neural crest stem cells derived from human ESCs and induced pluripotent stem cells: induction, maintenance, and differentiation into functional schwann cells. Stem cells translational medicine 1, 266-278.
Lupski, J. R. (1998). Charcot-Marie-Tooth disease: lessons in genetic mechanisms. Mol. Med. 4, 3-11.
Menendez, L., Yatskievych, T. A., Antin, P. B., and Dalton, S. (2011). Wnt signaling and a Smad pathway blockade direct the differentiation of human pluripotent stem cells to multipotent neural crest cells. Proceedings of the National Academy of Sciences of the United States of America 108, 19240-19245.
Martyn, C. N., and Hughes, R. A. (1997). Epidemiology of peripheral neuropathy. J. Neurol. Neurosurg. Psychiatry 62, 310-318.
Master, Z., McLeod, M., and Mendez, I. (2007). Benefits, risks and ethical considerations in translation of stem cell research to clinical applications in Parkinson's disease. J. Med. Ethics 33, 169-173.
Mica, Y., Lee, G., Chambers, S. M., Tomishima, M. J., and Studer, L. (2013). Modeling neural crest induction, melanocyte specification, and disease-related pigmentation defects in hESCs and patient-specific iPSCs. Cell Rep. 3, 1140-1152.
Mizisin, A. P. (2014). Mechanisms of diabetic neuropathy: Schwann cells. Handb. Clin. Neurol. 126, 401-428.
Mizisin, A. P., and Powell, H. C. (1993). Schwann cell injury is attenuated by aldose reductase inhibition in galactose intoxication. J. Neuropathol. Exp. Neurol. 52, 78-86.
Newbern, J., and Birchmeier, C. (2010). Nrgl/ErbB signaling networks in Schwann cell development and myelination. Seminars in cell & developmental biology 21, 922-928.
Oates, P. J. (2002). Polyol pathway and diabetic peripheral neuropathy. Int. Rev. Neurobiol. 50, 325-392.
Rodrigues, M. C., Rodrigues, A. A., Jr., Glover, L. E., Voltarelli, J., and Borlongan, C. V. (2012). Peripheral nerve repair with cultured schwann cells: getting closer to the clinics. The Scientific World Journal 2012, 413091.
Pareyson, D. (1999). Charcot-marie-tooth disease and related neuropathies: molecular basis for distinction and diagnosis. Muscle Nerve 22, 1498-1509.
Quasthoff, S., and Hartung, H. P. Chemotherapy-induced peripheral neuropathy. J. Neurol. 249, 9-17.

Rodrigues, M. C. O., Rodrigues, A. A., Glover, L. E., Voltarelli, J., and Borlongan, C. V. (2012). Peripheral Nerve Repair with Cultured Schwann Cells: Getting Closer to the Clinics. Sci. World J. 2012, e413091.

Simmons, Z., and Feldman, E. L. (2002). Update on diabetic neuropathy. Current opinion in neurology 15, 595-603.

Studer, L., Vera, E., and Cornacchia, D. (2015). Programming and Reprogramming Cellular Age in the Era of Induced Pluripotency. Cell stem cell 16, 591-600.

Tang, X., Zhou, L., Wagner, A. M., Marchetto, M. C. N., Muotri, A. R., Gage, F. H., and Chen, G. (2013). Astroglial cells regulate the developmental timeline of human neurons differentiated from induced pluripotent stem cells. Stem Cell Res. 11, 743-757.

Thompson, S. W., Davis, L. E., Kornfeld, M., Hilgers, R. D., and Standefer, J. C. (1984). Cisplatin neuropathy. Clinical, electrophysiologic, morphologic, and toxicologic studies. Cancer 54, 1269-1275.

Webber, C. A., Christie, K. J., Cheng, C., Martinez, J. A., Singh, B., Singh, V., Thomas, D., and Zochodne, D. W. (2011). Schwann cells direct peripheral nerve regeneration through the Netrin-1 receptors, DCC and Unc5H2. Glia 59, 1503-1517.

Wiliams, R. R., and Bunge, M. B. (2012). Schwann cell transplantation: a repair strategy for spinal cord injury? Prog. Brain Res. 201, 295-312.

Zochodne, D. W. (2007). Diabetes mellitus and the peripheral nervous system: manifestations and mechanisms. Muscle Nerve 36, 144-166.

Ziegler, L., Grigoryan, S., Yang, I. H., Thakor, N. V., and Goldstein, R. S. (2011). Efficient generation of schwann cells from human embryonic stem cell-derived neurospheres. Stem cell reviews 7, 394-403.

What is claimed is:

1. An in vitro method for inducing differentiation of SOX10-expressing neural crest lineage cells, comprising aggregating the SOX10-expressing neural crest lineage cells into 3D spheroids and concurrently contacting the 3D spheroids with at least one Wnt activator, at least one FGF activator, and at least one Schwann Cell (SC) differentiation inducer to produce a population of differentiated cells that express the Schwann cell precursor marker glial fibrillary acidic protein (GFAP); wherein the at least one Wnt activator lowers glycogen synthase kinase 3B (GSK3B) for activation of Wnt signaling; wherein the at least one FGF activator is selected from the group consisting of FGF1, FGF2, FGF4, FGF8, and mixtures thereof; wherein the at least one SC differentiation inducer comprises a neuregulin.

2. The method of claim 1, comprising contacting the cells expressing at least one neural crest lineage marker with the at least one Wnt activator and the at least one FGF activator for at least about 3 days, or for up to about 30 days, or for between about 5 days and about 15 days, or for between about 10 days and about 15 days, or for about 14 days.

3. The method of claim 1, comprising contacting the cells with the at least one SC differentiation inducer for at least about 3 days, or for up to about 30 days, or for between about 5 days and about 15 days, or for about 14 days.

4. The method of claim 1, wherein the differentiated cells expressing GFAP also express at least one Schwann cell precursor marker selected from the group consisting of SOX10, GAP43, BLBP, MPZ, Dhh, P75NTR, CD49D, TFAP2, CDH19, CD44, ERBB3, POU3F1, CALCB, GRP116, TSPYL5, ITPKA, SLC17A6, SYPL2, LOC100128252, ANGPTL7, LOC728978, ZNF502, SLC16A6, LPL, SLC30A2, and SLC10A4.

5. The method of claim 1, wherein the at least one Wnt activator is a small molecule selected from the group consisting of CHIR99021, Wnt-1, WNT3A, Wnt4, Wnt5a, derivatives thereof, and mixtures thereof.

6. The method of claim 1, wherein the at least one Wnt activator comprises CHIR99021.

7. The method of claim 1, wherein the at least one FGF activator comprises FGF2.

8. The method of claim 1, wherein the at least one SC differentiation inducer comprises Neuregulin 1 (NRG1).

9. The method of claim 1, comprising subjecting the population of differentiated cells expressing GFAP to conditions favoring maturation of the differentiated cells into a population of cells expressing at least one Schwann cell marker; wherein the conditions comprise: contacting the population of differentiated cells expressing GFAP with at least one FGF activator, and at least one SC differentiation enhancer; wherein the at least one FGF activator is selected from the group consisting of FGF1, FGF2, FGF4, FGF8, and mixtures thereof; wherein the at least one SC differentiation enhancer comprises a neuregulin and cyclic adenosine monophosphate (cAMP).

10. The method of claim 9, wherein the at least one Schwann cell marker is selected from the group consisting of LRRTM4, CDH1, FABP7, BDNF, UNC5B, SOSTDC1, OLIG1, PLAT, KCNJ10, SHH, NTN1, GDNF, ERBB3, GAP43, SOX10, S100, POU3F1, PMP22, MBP, AQP4, MPZ, NGFR, NFATC4, MOG, IFNG, MAL, NTF3, TGFB1, CD9, CD81, CD44, CD98, CD49E, CD49D, TYRP1, ENTHD1, NT5E, HTR2B, NOV, IL8, SLC16A6, CDKN2A, PLP2, S100A6, AQP9, and CDH19.

11. The method of claim 9, wherein the contacting of the population of differentiated cells expressing GFAP with the at least one SC differentiation enhancer is for at least about 3 days, for about 10 days, or for about 35 days.

12. The method of claim 9, further comprising culturing the 3D spheroids in an adherent culture.

13. The method of claim 1, wherein the SOX10-expressing neural crest lineage cells further express at least one neural crest lineage marker selected from the group consisting of p75, HNK1, CD49D, ERBB3, TFAP2, SNAIL, and SLUG.

* * * * *